US009657110B2

(12) United States Patent
Collighan et al.

(10) Patent No.: US 9,657,110 B2
(45) Date of Patent: May 23, 2017

(54) POLYPEPTIDES AND USE THEREOF

(75) Inventors: Russell Collighan, Birmingham (GB); Martin Griffin, Birmingham (GB); Kamila Pytel, Birmingham (GB); Zhuo Wang, Birmingham (GB)

(73) Assignee: ASTON UNIVERSITY, Birmingham (GB)

( * ) Notice: Subject to any disclaimer, the term of this patent is extended or adjusted under 35 U.S.C. 154(b) by 143 days.

(21) Appl. No.: 14/113,827

(22) PCT Filed: Apr. 30, 2012

(86) PCT No.: PCT/GB2012/000398
§ 371 (c)(1),
(2), (4) Date: Jan. 13, 2014

(87) PCT Pub. No.: WO2012/146901
PCT Pub. Date: Nov. 1, 2012

(65) Prior Publication Data
US 2014/0199325 A1 Jul. 17, 2014

(30) Foreign Application Priority Data

Apr. 28, 2011 (GB) .................................. 1107147.9

(51) Int. Cl.
| C07K 16/40 | (2006.01) |
| C07K 7/08 | (2006.01) |
| C07K 7/06 | (2006.01) |
| C07K 14/435 | (2006.01) |
| C07K 14/475 | (2006.01) |
| A61K 38/00 | (2006.01) |

(52) U.S. Cl.
CPC ............... *C07K 16/40* (2013.01); *C07K 7/06* (2013.01); *C07K 7/08* (2013.01); *C07K 14/435* (2013.01); *C07K 14/475* (2013.01); *A61K 38/00* (2013.01)

(58) Field of Classification Search
None
See application file for complete search history.

(56) References Cited

U.S. PATENT DOCUMENTS

| 4,440,859 A | 4/1984 | Rutter et al. |
| 4,485,045 A | 11/1984 | Regen |
| 4,530,901 A | 7/1985 | Weissmann |
| 4,544,545 A | 10/1985 | Ryan et al. |
| 4,582,800 A | 4/1986 | Crowl |
| 4,677,063 A | 6/1987 | Mark et al. |
| 4,678,751 A | 7/1987 | Goeddel |
| 4,704,362 A | 11/1987 | Itakura |
| 4,710,463 A | 12/1987 | Murray |
| 4,757,006 A | 7/1988 | Toole |
| 4,766,075 A | 8/1988 | Goeddel et al. |
| 4,810,648 A | 3/1989 | Stalker |
| 4,816,567 A | 3/1989 | Cabilly et al. |
| 5,643,872 A | 7/1997 | Ali et al. |
| 6,008,058 A | 12/1999 | Spatola et al. |
| 6,027,726 A | 2/2000 | Ansell |
| 6,139,869 A | 10/2000 | Hosokawa et al. |
| 6,190,896 B1 * | 2/2001 | Fraij .............................. 435/193 |
| 2008/0305517 A1 * | 12/2008 | Griffin et al. ................ 435/68.1 |

FOREIGN PATENT DOCUMENTS

| KR | 2010 0125079 | 11/2010 |
| WO | WO 01/42277 | 6/2001 |
| WO | WO 0142277 A2 * | 6/2001 |
| WO | WO 01/85224 | 11/2001 |
| WO | WO 03/059973 | 7/2003 |
| WO | WO 2004/039955 | 5/2004 |
| WO | WO 2004/070386 | 8/2004 |
| WO | WO 2005/007197 | 1/2005 |
| WO | WO 2006/044614 | 4/2006 |
| WO | WO 2007/107654 | 9/2007 |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Vajdos et al. (J Mol Biol. Jul. 5, 2002;320(2):415-28 at 416).*
Brown et al. (J Immunol. May 1996;156(9):3285-91 at 3290 and Tables 1 and 2).*
Achyuthan et al., "Identification of a guanosine triphosphate-binding site on guinea pig liver transglutaminase. Role of GTP and calcium ions in modulating activity", *J Biol Chem*, 262: 1901-1906, 1987.
Achyuthan et al., "Immunochemical analyses of human plasma fibronectin-cytosolic transglutaminase interactions", *J Immunol Methods*, 180: 69-79, 1995.
Aeschlimann et al., "Protein crosslinking in assembly and remodelling of extracellular matrices: the role of transglutaminases", *Connective Tissue Research*, 41: 1-27, 2000.
Amendola et al., ""Tissue" transglutaminase in AIDS", *J Immunol Methods*, 265: 145-159, 2002.
Ariëns et al., "Role of factor XIII in fibrin clot formation and effects of genetic polymorphisms", *Blood*, 100: 743-754, 2002.
Balklava et al., "Analysis of tissue transglutaminase function in the migration of Swiss 3T3 fibroblasts: the active-state conformation of the enzyme does not affect cell motility but is important for its secretion", *J. Biol. Chem.*, 277:16567-16575, 2002.

(Continued)

*Primary Examiner* — Brian J Gangle
*Assistant Examiner* — Andrea McCollum
(74) *Attorney, Agent, or Firm* — Parker Highlander PLLC

(57) ABSTRACT

The present invention provides a polypeptides capable of modulating tissue transglutaminase-induced cell behavior wherein the polypeptide comprises or consists of either (a) the amino acid sequence of a heparin-binding site of a tissue transglutaminase, or a functional fragment, variant, fusion or derivative thereof, or a fusion of said fragment, variant or derivative thereof or (b) an antibody capable of binding to a heparin-binding site of a tissue transglutaminase, or an antigen-binding fragment or derivative thereof. In one embodiment, the heparin-binding site of a tissue transglutaminase comprises or consists of an amino acid sequence of SEQ ID NO: 1, The invention further provides medical uses of the polypeptides of the invention and methods of treatment using the same.

10 Claims, 20 Drawing Sheets

(56) References Cited

OTHER PUBLICATIONS

Figure 1D:
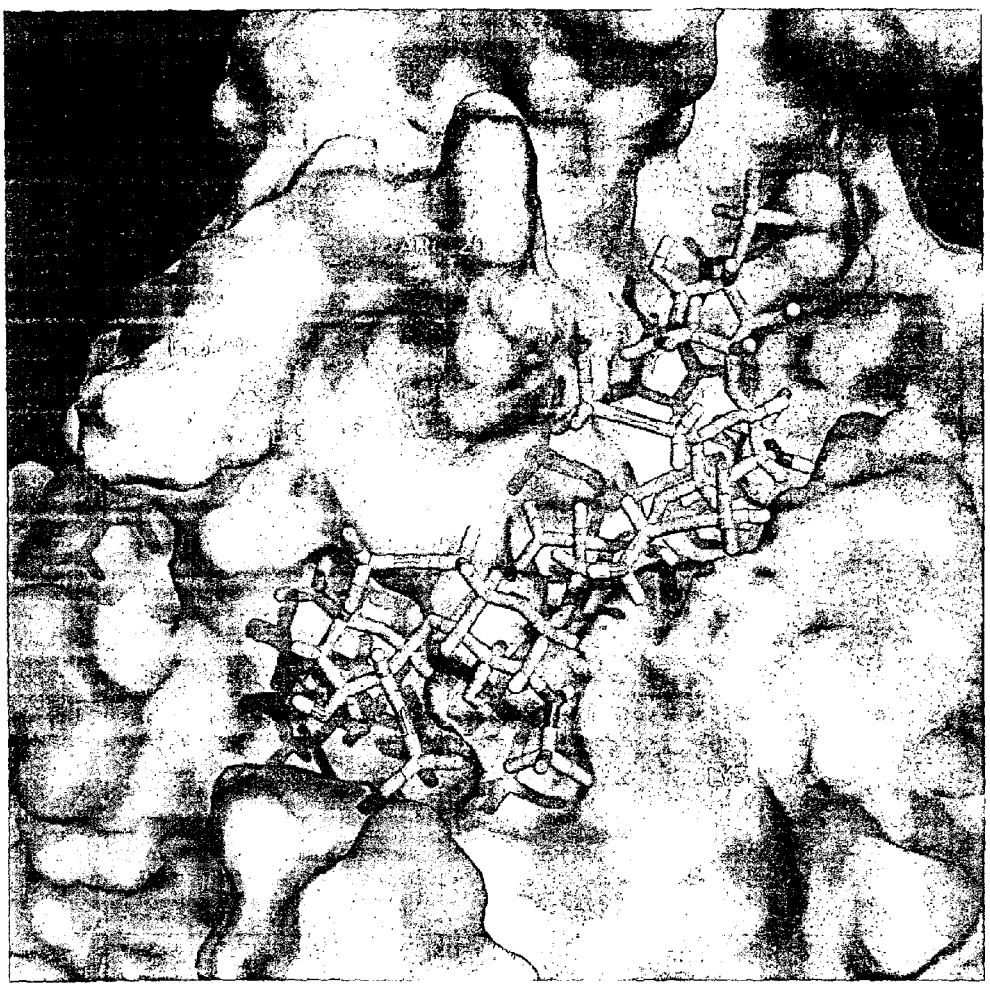

Baudys et al., "Extending insulin action in vivo by conjugation to carboxymethyl dextran", *Bioconjug Chem*, 9:176-83, 1998.
Beggs, "Transformation of yeast by a replicating hybrid plasmid", *Nature*, 275:104-109, 1978.
Behe et al., "Biodistribution, blood half-life, and receptor binding of a somatostatin-dextran conjugate", *Med Oncol*, 18:59-64, 2001.
Bergamini et al., "Inhibition of erythrocyte transglutaminase by GTP", *Biochimica Et Biophysica Acta*, 916:149-151, 1987.
Boerner et al., "Production of antigen-specific human monoclonal antibodies from in vitro-primed human splenocytes", *J Immunol*, 147:86-95, 1991.
Bowen et al., "Relationship between molecular mass and duration of activity of polyethylene glycol conjugated granulocyte colony-stimulating factor mutein", *Exp Hematol*, 27:425-32, 1999.
Bruce & Peters, "The subcellular localization of transglutaminase in normal liver and in glucagon-treated and partial hepatectomized rats", *Biosci Rep*, 3:1085-90, 1983.
Cardin & Weintraub, "Molecular modeling of protein-glycosaminoglycan interactions", *Arteriosclerosis*, 9:21-32, 1989.
Casadio et al., "The structural basis for the regulation of tissue transglutaminase by calcium ions", *European Journal of Biochemistry*, 262:672-679, 1999.
Chan et al., "Lowering of trichosanthin immunogenicity by site-specific coupling to dextran", *Biochem Pharmacol*, 57:927-34, 1999.
Chapman et al., "Therapeutic antibody fragments with prolonged in vivo half-lives", *Nat Biotechnol*, 17:780-3, 1999.
Chapman, "PEGylated antibodies and antibody fragments for improved therapy: a review", *Adv Drug Deliv Rev*, 54:531-45, 2002.
Citron et al., "Intron-exon swapping of transglutaminase mRNA and neuronal Tau aggregation in Alzheimer's disease", *J Biol Chem*, 276: 3295-3301, 2001.
Cohen et al., "Nonchromosomal antibiotic resistance in bacteria: genetic transformation of *Escherichia coli* by R-factor DNA", *PNAS*, 69: 2110-2114, 1972.
Cote et al., "Generation of human monoclonal antibodies reactive with cellular antigens", *PNAS*, 80: 2026-2030, 1983.
Elliott et al., "Enhancement of therapeutic protein in vivo activities through glycoengineering", *Nat Biotechnol*, 21:414-21, 2003.
Eppstein et al., "Biological activity of liposome-encapsulated murine interferon gamma is mediated by a cell membrane receptor", *PNAS*, 82:3688-92, 1985.
Folkman, "Angiogenesis in cancer, vascular, rheumatoid and other disease", *Nat Med*, 1: 27-31, 1995.
Gaudry et al., "Cell surface localization of tissue transglutaminase is dependent on a fibronectin-binding site in its N-terminal beta-sandwich domain", *Journal of Biological Chemistry*, 274:30707-30714, 1999.
Gaudry et al., "Tissue transglutaminase is an important player at the surface of human endothelial cells: evidence for its externalization and its colocalization with the beta(1) integrin", *Experimental Cell Research*, 252:104-113, 1999.
Gentile et al., "Isolation and characterization of cDNA clones to mouse macrophage and human endothelial cell tissue transglutaminases", *Journal of Biological Chemistry*, 266:478-483, 1991.
Goldenberg, "Etanercept, a novel drug for the treatment of patients with severe, active rheumatoid arthritis", *Clin Ther*, 21:75-87; discussion 1-2, 1999.
Greenberg et al., "The transglutaminase in vascular cells and tissues could provide an alternate pathway for fibrin stabilization", *Blood*, 70: 702-709, 1987.
Greenberg et al., "Transglutaminases: multifunctional cross-linking enzymes that stabilize tissues", *FASEB*, 5: 3071-3077, 1991.
Griffin et al., "Synthesis of potent water-soluble tissue transglutaminase inhibitors", *Bioorganic & Medicinal Chemistry Letters*, 18:5559-5562, 2008.
Griffin et al., "Transglutaminases: Nature's biological glues", *Biochemical Journal.*, 368:377-396, 2002.

Hamilton-Wessler et al., "Mechanism of protracted metabolic effects of fatty acid acylated insulin, NN304, in dogs: retention of NN304 by albumin", *Diabetologia*, 42(10):1254-63, 1999.
Hang et al., "Identification of a novel recognition sequence for fibronectin within the NH2-terminal beta-sandwich domain of tissue transglutaminase", *J Biol Chem*, 280:23675-23683, 2005.
Hasegawa et al., "A novel function of tissue-type transglutaminase: protein disulphide isomerase", *Biochemical Journal*, 373:793-803, 2003.
Hileman et al., "Glycosaminoglycan-protein interactions: definition of consensus sites in glycosaminoglycan binding proteins", *Bioessays*, 20:156-167, 1998.
Hoogenboom & Winter, "By-passing immunisation. Human antibodies from synthetic repertoires of germline VH gene segments rearranged in vitro", *J Mol Biol*, 227:381-8, 1992.
Huang & Miller, "A time-efficient, linear-space local similarity algorithm", *Adv Appl Math*, 12:337-357, 1991.
Hwang et al., "Hepatic uptake and degradation of unilamellar sphingomyelin/cholesterol liposomes: a kinetic study", *PNAS*, 77:4030-4, 1980.
Iismaa et al., "Transglutaminases and disease: lessons from genetically engineered mouse models and inherited disorders", *Physiol Rev.*, 89:991-1023, 2009.
International Preliminary Report on Patentability issued in International Application No. PCT/GB2012/000398, mailed Oct. 29, 2013.
International Search Report and Written Opinion issued in International Application No. PCT/GB2012/000398, mailed Sep. 20, 2012.
Jeong et al., "The fibronectin-binding domain of transglutaminase", *J Biol Chem*, 270:5654-8, 1995.
Johnson et al., "External GTP-bound transglutaminase 2 is a molecular switch for chondrocyte hypertrophic differentiation and calcification", *J Biol Chem*, 280:15004-12, 2005.
Johnson et al., "Interleukin-1 induces pro-mineralizing activity of cartilage tissue transglutaminase and factor XIIIa", *Am J Pathol*, 159: 149-163, 2001.
Johnson et al., "Transglutaminase transcription and antigen translocation in experimental renal scarring", *J Am Soc Neph*, 10: 2146-2157, 1999.
Jones et al., "Reduced expression of tissue transglutaminase in a human endothelial cell line leads to changes in cell spreading, cell adhesion and reduced polymerisation of fibronectin", *J Cell Sci*, 110: 2461-2472, 1997.
Jones et al., "Replacing the complementarity-determining regions in a human antibody with those from a mouse", *Nature*, 321: 522-525, 1986.
Kim et al., "Synthesis and properties of dextran-linked ampicillin", *Drug Dev Ind Pharm*, 27:97-101, 2001.
Kinsella et al., "Formation of high molecular weight dermatan sulfate proteoglycan in bovine aortic endothelial cell cultures. Evidence for transglutaminase-catalyzed cross-linking to fibronectin", *JBC*, 265: 17891-17896, 1990.
Kohler et al., "Continuous cultures of fused cells secreting antibody of predefined specificity", *Nature*, 256: 495-497, 1975.
Kotsakis et al., "The role of tissue transglutaminase (TG2) in regulating the tumour progression of the mouse colon carcinoma CT26", *Amino Acids*, 41(4) :909-21, 2011.
Kozbor et al., "Specific immunoglobulin production and enhanced tumorigenicity following ascites growth of human hybridomas", *J Immunol Methods*, 81: 31-42, 1985.
Kurtzhals et al., "Albumin binding of insulins acylated with fatty acids: characterization of the ligand-protein interaction and correlation between binding affinity and timing of the insulin effect in vivo", *Biochem J*, 312:725-31, 1995.
Lai et al., "C-terminal deletion of human tissue transglutaminase enhances magnesium-dependent GTP/ATPase activity", *Journal of Biological Chemistry*, 271: 31191-31195, 1996.
Lee et al., "GTP hydrolysis by guinea pig liver transglutaminase", *Biochem Biophys Res Commun*, 162:1370-5, 1989.
LeMosy et al., "Visualization of purified fibronectin-transglutaminase complexes", *Journal of Biological Chemistry*, 267:7880-7885, 1992.
Lesort et al., "Distinct nuclear localization and activity of tissue transglutaminase", *J Biol chem*, 273: 11991-11994, 1998.

(56) References Cited

OTHER PUBLICATIONS

Lidholt et al., "A single mutation affects both N-acetylglucosaminyltransferase and glucuronosyltransferase activities in a Chinese hamster ovary cell mutant defective in heparan sulfate biosynthesis", *PNAS*, 89:2267-2271, 1992.
Lismaa et al., "Transglutaminases and disease: lessons from genetically engineered mouse models and inherited disorders", *Physical Rev*, 89:991:1023, 2009.
Liu et al., "Structural basis for the guanine nucleotide-binding activity of tissue transglutaminase and its regulation of transamidation activity", *PNAS*, 99:2743-2747, 2002.
Luchansky et al., "Application of electroporation for transfer of plasmid DNA to Lactobacillus, Lactococcus, Leuconostoc, Listeria, Pediococcus, Bacillus, Staphylococcus, Enterococcus and Propionibacterium", *Mol Microbiol*, 2:637-646, 1988.
Margalit et al., "Comparative analysis of structurally defined heparin binding sequences reveals a distinct spatial distribution of basic residues", *Journal of Biological Chemistry*, 268:19228-19231, 1993.
Mariani et al., "Ligand-induced conformational changes in tissue transglutaminase: Monte Carlo analysis of small-angle scattering data", *Biophysical Journal*, 78:3240-3251, 2000.
Marks et al., "By-passing immunization. Human antibodies from V-gene libraries displayed on phage", *J Mol Biol*, 222:581-97, 1991.
Martinez et al., "Transglutaminase-mediated processing of fibronectin by endothelial cell monolayers", *Biochemistry*, 33: 2538-2545, 1994.
Marzari et al., "Molecular dissection of the tissue transglutaminase autoantibody response in celiac disease", *J Immunol*, 166: 4170-4176, 2001.
Mastroberardino et al., ""Tissue" transglutaminase contributes to the formation of disulphide bridges in proteins of mitochondrial respiratory complexes", *Biochimica Et Biophysica Acta-Bioenergetics*, 1757:1357-1365, 2006.
Mehta et al., "High levels of transglutaminase expression in doxorubicin-resistant human breast carcinoma cells", *J Cancer*, 58: 400-406, 1994.
Mehta et al., "Multidrug-resistant MCF-7 cells: an identity crisis?", *J Natl Cancer Inst*, 94: 1652-1654, 2002.
Meziere et al., "In vivo T helper cell response to retro-inverso peptidomimetics", *J Immunol*, 159: 3230-3237, 1997.
Mishra & Murphy, "Tissue transglutaminase has intrinsic kinase activity: identification of transglutaminase 2 as an insulin-like growth factor-binding protein-3 kinase", *Journal of Biological Chemistry*, 279:23863-23868, 2004.
Molineux, "Pegylation: engineering improved pharmaceuticals for enhanced therapy", *Cancer Treat Rev*, 28 Suppl A:13-6, 2002.
Nakashima et al., "In vitro characteristics and in vivo plasma disposition of cisplatin conjugated with oxidized and dicarboxymethylated dextrans", *Biol Pharm Bull*, 22:756-61, 1999.
Orlandi et al., "Cloning immunoglobulin variable domains for expression by the polymerase chain reaction", *PNAS*, 86: 3833-3837, 1989.
Osborn et al., "Albutropin: a growth hormone-albumin fusion with improved pharmacokinetics and pharmacodynamics in rats and monkeys", *Eur J Pharmacol*, 456:149-58, 2002.
Osborn et al., "Pharmacokinetic and pharmacodynamic studies of a human serum albumin-interferon-alpha fusion protein in cynomolgus monkeys", *J Pharmacol Exp Ther*, 303:540-8, 2002.
Parsons et al., "Site-directed perturbation of protein kinase C-integrin interaction blocks carcinoma cell chemotaxis", *Molecular and Cellular Biology*, 22:5897-5911, 2002.
Piacentini et al., "Transglutaminase overexpression sensitizes neuronal cell lines to apoptosis by increasing mitochondrial membrane potential and cellular oxidative stress", *Journal of Neurochemistry*, 81:1061-1072, 2002.
Pinkas et al., "Transglutaminase 2 undergoes a large conformational change upon activation", *PLoS Biology*, 5:e327, 2007.
Pinto et al., "Treatment of YAC128 mice and their wild-type littermates with cystamine does not lead to its accumulation in plasma or brain: implications for the treatment of Huntington disease", *J Neurochemistry*, 94(4): 1087-1101, 2005.
Rich, "Protease Inhibitors", *Research monographs in cell and tissue physiology*, Barrett & Selveson, eds., Elsevier, pp. 153-178, 1986. Print.
Riechmann et al., "Reshaping human antibodies for therapy", *Nature*, 332:323-329, 1988.
Scarpellini et al., "Heparan sulfate proteoglycans are receptors for the cell-surface trafficking and biological activity of transglutaminase-2", *Journal of Biological Chemistry*, 284:18411-18423, 2009.
Southern, "Detection of specific sequences among DNA fragments separated by gel electrophoresis", *J Mol Biol*, 98: 503-517, 1975.
Stamnaes et al., "Redox regulation of transglutaminase 2 activity", *Journal of Biological Chemistry*, 285:25402-25409, 2010.
Syed et al., "Inhibition of thrombin by hirudin genetically fused to wild-type or mutant antithrombin", *Thromb Res*, 84:419-29, 1996.
Takeuchi et al., "Putative nucleotide binding sites of guinea pig liver transglutaminase", *FEBS Letters*, 307:177-180, 1992.
Telci et al., "Fibronectin-tissue transglutaminase matrix rescues RGD-impaired cell adhesion through syndecan-4 and beta1 integrin co-signaling", *J. Biol. Chem.*, 283:20937-20947, 2008.
Telci et al., "Increased TG2 expression can result in induction of transforming growth factor beta 1, causing increased synthesis and deposition of matrix proteins, which can be regulated by nitric oxide", *J. Biol. Chem.*, 284:29547-29558, 2009.
Thorsett et al., "Dipeptide mimics. Conformationally restricted inhibitors of angiotensin-converting enzyme", *Biochem Biophys Res Comm*, 111:166-71, 1983.
Upchurch et al., "Cellular transglutaminase has affinity for extracellular matrix", *In Vitro Cellular & Developmental Biology*, 23:795-800, 1987.
Upchurch et al., "Localization of cellular transglutaminase on the extracellular matrix after wounding: characteristics of the matrix bound enzyme", *Journal of Cellular Physiology* 149:375-382, 1991.
Van Groningen et al., "Expression of tissue-type transglutaminase correlates positively with metastatic properties of human melanoma cell lines", *Int J Cancer*, 60: 383-387, 1995.
Veber et al., "Conformationally restricted bicyclic analogs of somatostatin", *PNAS*, 75: 2636-2640, 1978.
Verderio et al., "A novel RGD-independent cel adhesion pathway mediated by fibronectin-bound tissue transglutaminase rescues cells from anoikis", *J. Biol. Chem.*, 278:42604-42614, 2003.
Verderio et al., "Novel interactions of TG2 with heparan sulfate proteoglycans: reflection on physiological implications", *Amino Acids*, 36:671-677, 2009.
Verderio et al., "Regulated expression of tissue transglutaminase in Swiss 3T3 fibroblasts: effects on the processing of fibronectin, cell attachment, and cell death", *Exp. Cell Res.*, 239:119-138, 1998.
Veronese & Harris, "Introduction and overview of peptide and protein pegylation", *Adv Drug Deliv Rev*, 54:453-6, 2002.
Veronese & Pasut, "PEGylation, successful approach to drug delivery", *Drug Discov Today*, 10:1451-8, 2005.
Wang et al., "Importance of syndecan-4 and syndecan-2 in osteoblast cell adhesion and survival mediated by a tissue transglutaminase-fibronectin complex", *Exp. Cell Res.*, 317(3):367-81, 2011.
Wang et al., "RGD-independent cell adhesion via a tissue transglutaminase-fibronectin matrix promotes fibronectin fibril deposition and requires syndecan-4/2 $\alpha5\beta1$ integrin co-signaling", *J. Biol. Chem.*, 285:40212-40229, 2010.
Wang et al., "Structural and biological characterization of pegylated recombinant interferon alpha-2b and its therapeutic implications", *Adv Drug Deliv Rev*, 54:547-70, 2002.
Winter et al., "Man-made antibodies", *Nature*, 349: 293-299, 1991.
Wulbrand et al., "A novel somatostatin conjugate with a high affinity to all five somatostatin receptor subtypes", *Cancer*, 94:1293-7, 2002.
Yasueda et al., "Purification and characterization of a tissue-type transglutaminase from red sea bream (*Pagrus major*)", *Bioscience Biotechnology and Biochemistry*, 58:2041-2045, 1994.
Yu et al., "Determination of the sites of tyrosine O-sulfation in peptides and proteins", Nature Methods, 4(7):583-588, 2007.

(56) References Cited

OTHER PUBLICATIONS

Yura et al., "Synthesis and pharmacokinetics of a novel macromolecular prodrug of Tacrolimus (FK506), FK506-dextran conjugate", *J Control Release*, 57:87-99, 1999.

Akimov et al., "Tissue transglutaminase is a integrin-binding adhesion co-receptor for fibronectin", *Journal of Cell Biology*, 148:825-838, 2000.

Becker & Guarente, "High-Efficiency Transformation of Yeast by Electroporation", *Methods Enzymol*, 194 182-187, 1990.

Manon-Jensen et al., "Proteoglycans in health and disease: the multiple roles of syndecan shedding", *Febs Journal*, 277:3876-3889, 2010.

Presta, "Antibody Engineering", *Curr Op Struct Biol*, 2: 593-596, 1992.

* cited by examiner

FIGURE 1(A-C)
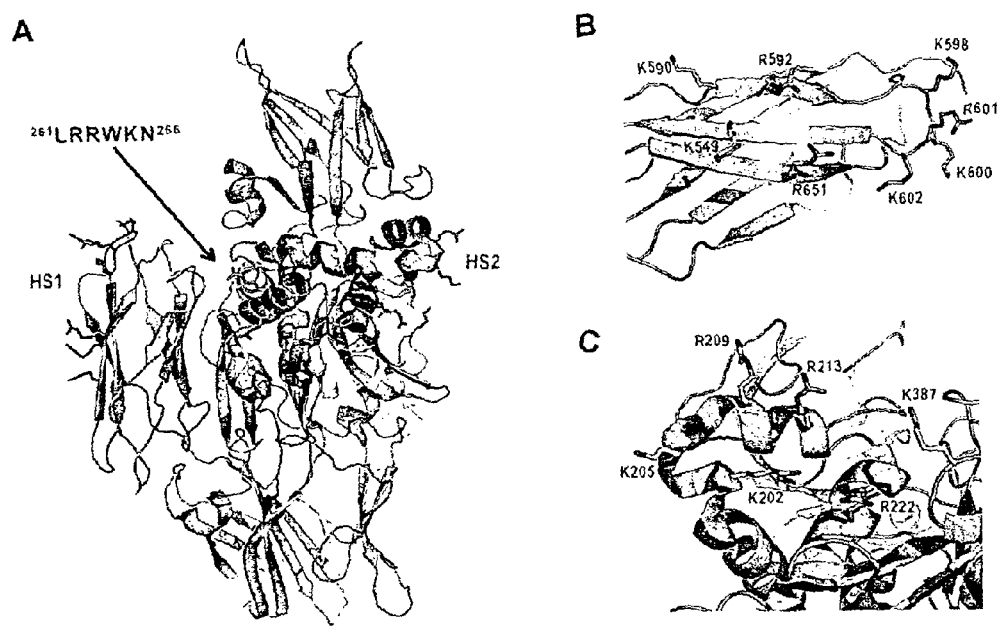

FIGURE 2(A-C)
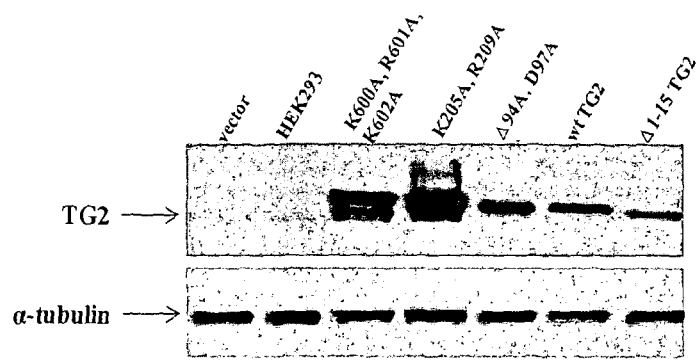
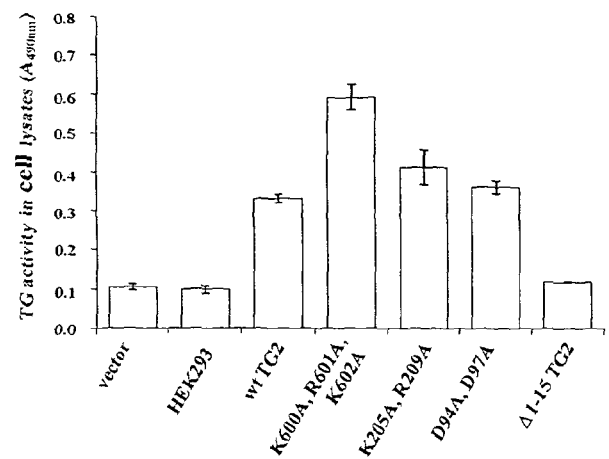
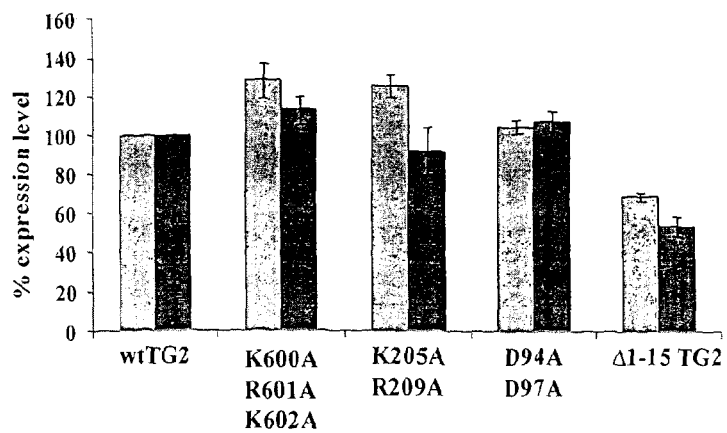
☐ Normalised expression level of wild type and TG2 mutant to tubulin (HEK293)
■ Normalised cell lysate activity of wt and mutant TG2 to the relative expression level (HEK293)

FIGURE 2(D-F)
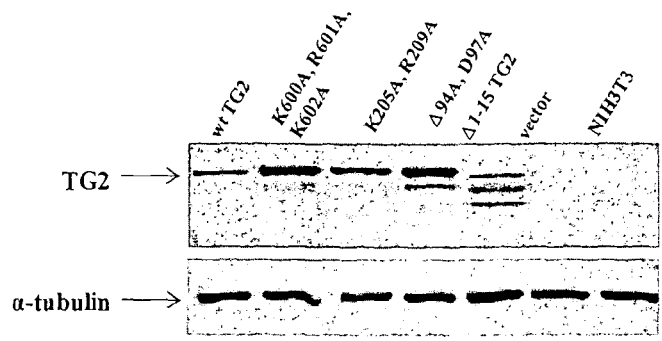
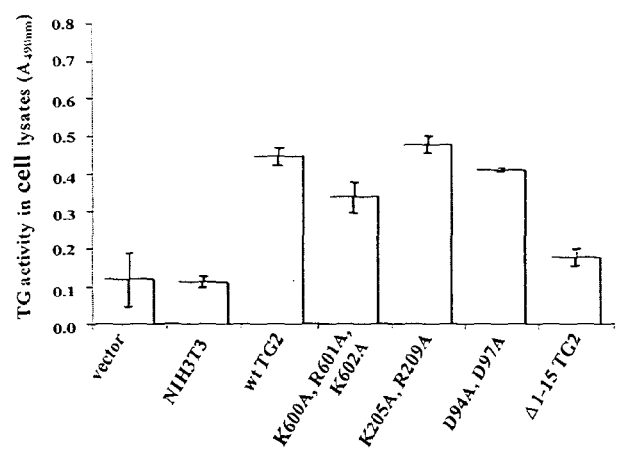
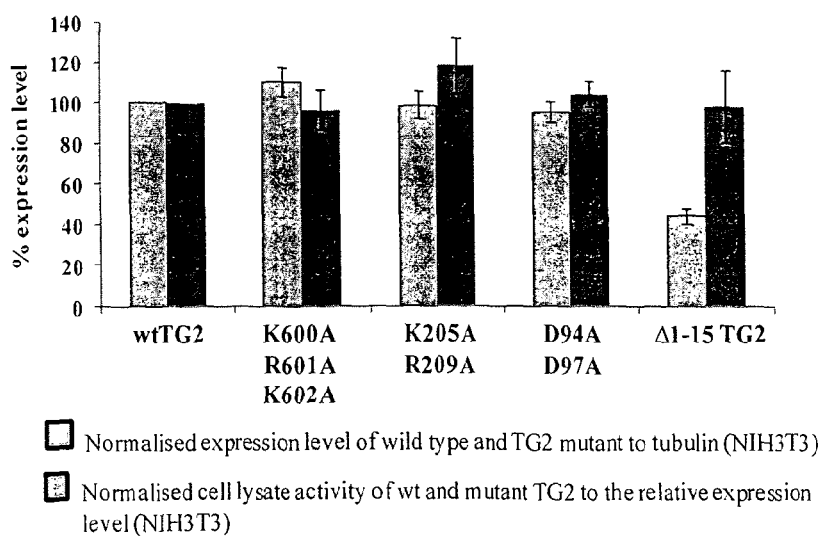
☐ Normalised expression level of wild type and TG2 mutant to tubulin (NIH3T3)
■ Normalised cell lysate activity of wt and mutant TG2 to the relative expression level (NIH3T3)

FIGURE 4(A-C)
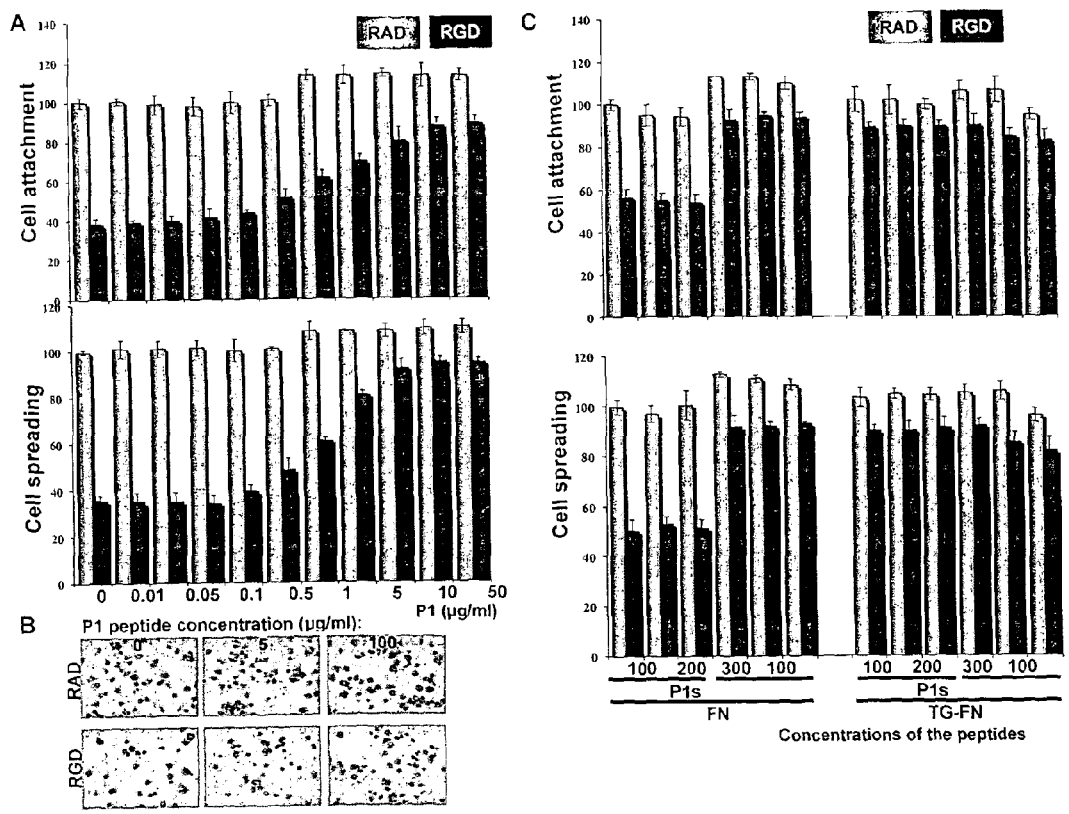

FIGURE 4(D-E)
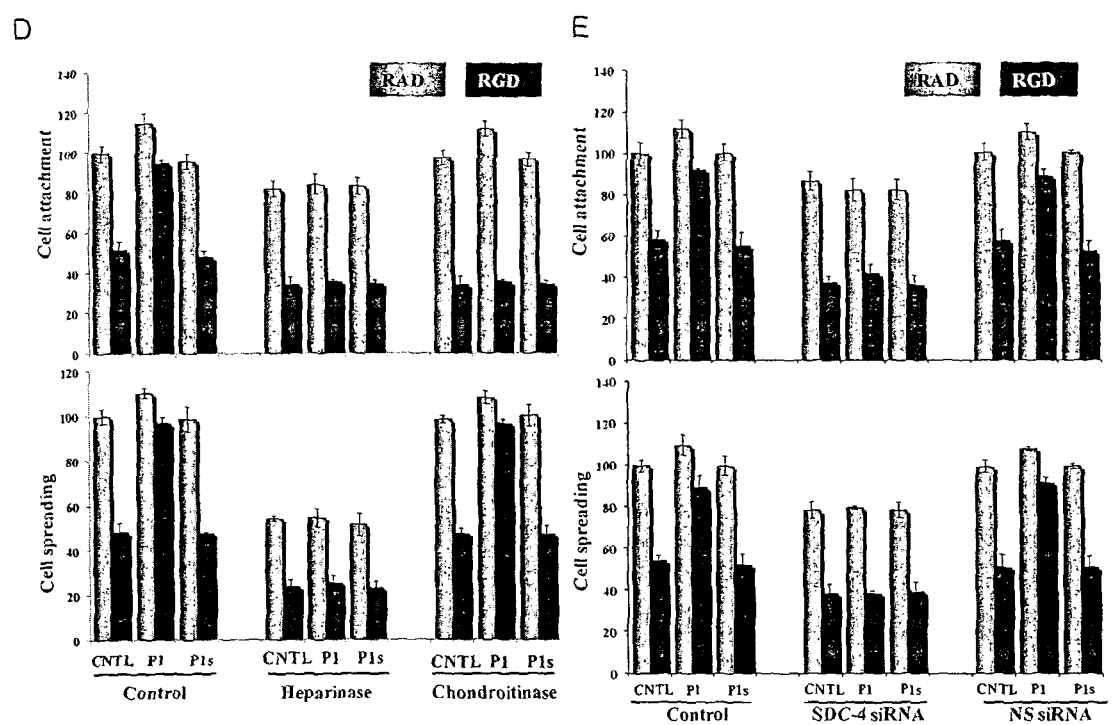

FIGURE 15
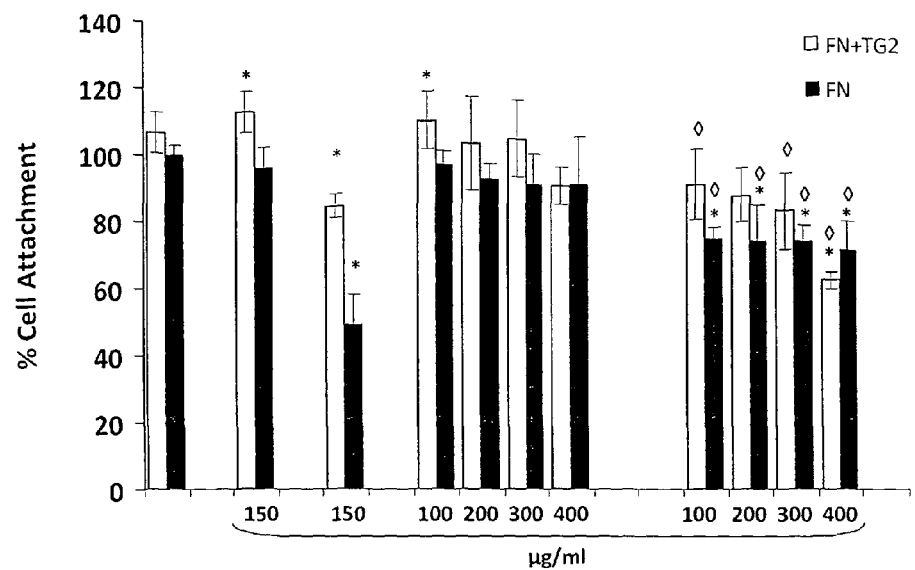
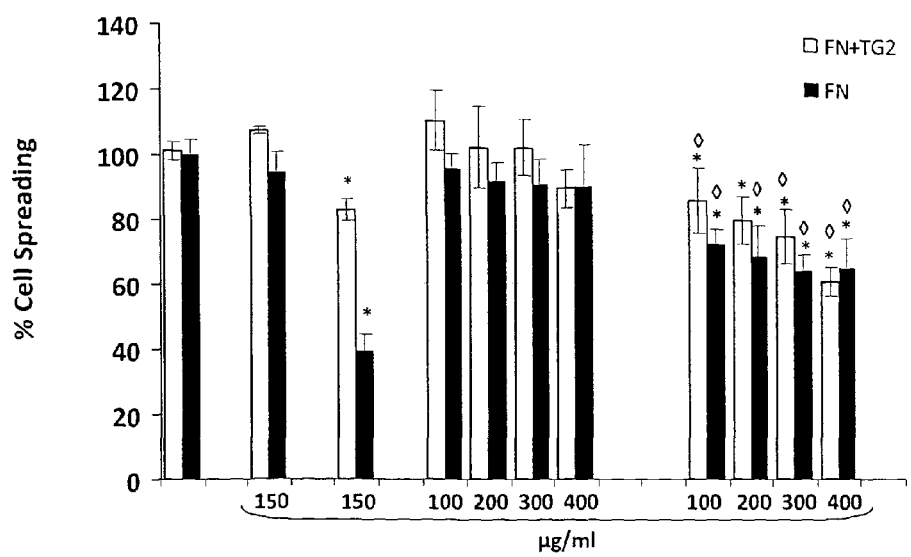

Figure 16A:
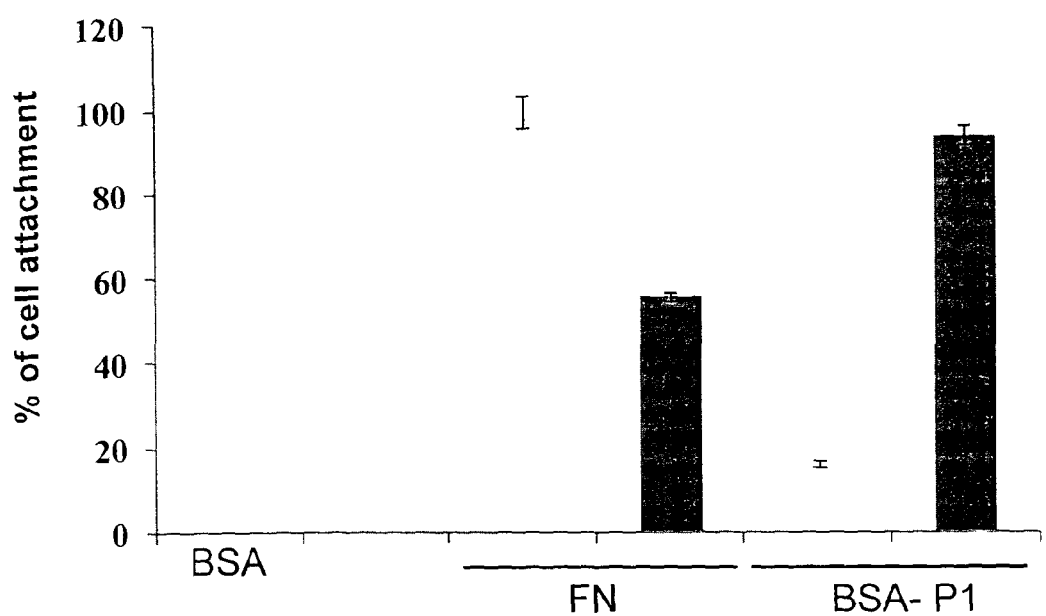

FIGURE 16(B-C)
(B)
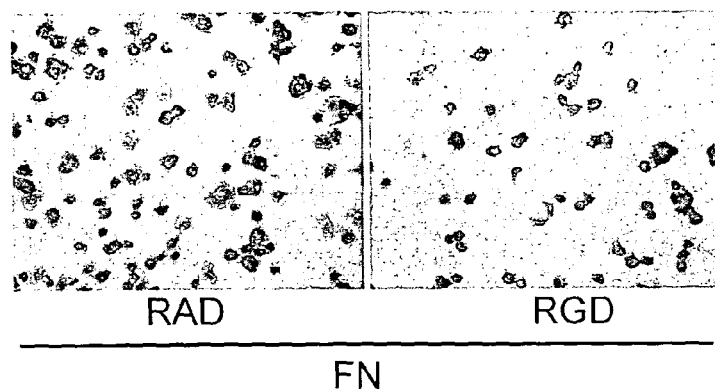
FN
(C)
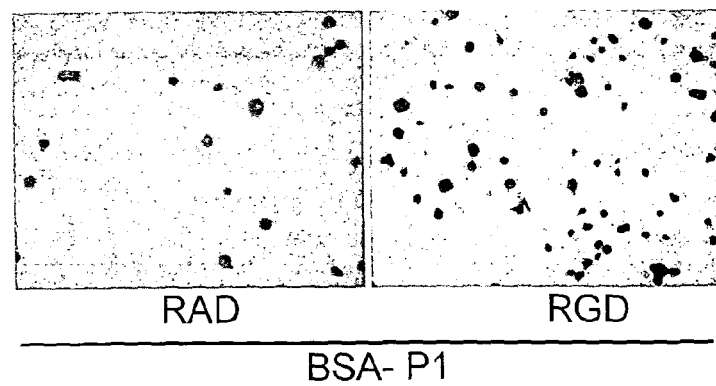
BSA-P1

POLYPEPTIDES AND USE THEREOF

This application is a national phase application under 35 U.S.C. 371 of International Application No. PCT/GB2012/000398, filed Apr. 30, 2012, which claims priority to Great Britain Application No. 1107147.9, filed Apr. 28, 2011. The entire text of each of the above referenced disclosures is specifically incorporated herein by reference.

FIELD OF INVENTION

The present invention relates to novel polypeptides and their use in medicine. In particular, the invention provides polypeptides capable of modulating tissue transglutaminase-induced cell behaviour, which may be used in the treatment and/or prevention of diseases and disorders responsive to mimicking or inhibiting the effects of tissue transglutaminase on cell signalling, adhesion, spreading and/or migration.

INTRODUCTION

Transglutaminases (TGases) are an important class of protein crosslinking enzymes that catalyse protein aggregation reactions in blood coagulation (Greenberg, C. S., et al., 1991, *FASEB J.* 5, 3071-3077), skin maturation (Thacher, S. M. & Rice, R. H., 1985, *Cell* 40, 685-695) and the clotting of seminal secretions (Dubbink, H. J., et al., 1999, *Lab. Invest.* 79, 141-150). The most widespread member of the family is the cellular form of the enzyme, tissue transglutaminase (tTGase or TG2), which is expressed in varying amounts in many cell types. Like the well-characterised plasma TGase (blood coagulation factor XIIIa) (Greenberg, C. S., et al., 1991, *FASEB J.* 5, 3071-3077) and keratinocyte TGase (Thacher, S. M. & Rice, R. H., 1985, *Cell* 40, 685-695), tTGases are calcium-dependent enzymes that catalyse the formation of crosslinks proteins via ε(γ-glutamyl) isopeptide bonds and the incorporation of polyamines at certain glutamine residues (Greenberg, C. S., et al., 1991, *FASEB J.* 5, 3071-3077). However, tTGase is unique in the transglutaminase family of enzymes in that is able to bind and hydrolyze GTP and ATP (Achyuthan, K. E. & Greenberg, C. S., 1987, *J. Biol. Chem.* 262, 1901-1906), and to bind to fibronectin (Achyuthan, K. E., et al., 1995, *J. Immunol. Methods* 180, 67-79).

Tissue TGase (tTGase or TG2) is predominantly located in the cytosol, although tTGase has also been reported to exist in the nucleus (Lesort, M., et al., 1998, *J. Biol. Chem.* 273, 11991-11994), at the cell surface and in the extracellular matrix (Martinez, J., et al, 1994, *Biochemistry* 33, 2538-2545). The enzyme is highly expressed in endothelial cells (Greenberg, C. S., et al., 1987, *Blood* 20, 702-709) and its activity at the surface of such cells is thought to enhance basement membrane stabilisation, cell spreading and cell adhesion (Martinez, J., et al., 1994, *Biochemistry* 33, 2538-2545; Greenberg, C. S., et al., 1987, *Blood* 20, 702-709; Kinsella, M. G. & Wight, T. N., 1990, *J. Biol. Chem.* 265, 17891-17896; Jones, R. A., et al., 1997, *J. Cell Sci.* 110, 2461-2472; Gaudry C. A., et al., 1999, *Exp. Cell Res.* 252, 104-113). However, the overall significance of the high amount of enzyme in this cell type and its biological function is poorly understood.

Protein modification mediated by tissue transglutaminases has been implicated in the pathology and aetiology of numerous diseases and processes (see review by Aeschlimann & Thomazy, 2000, *Connective Tissue Research* 41(1): 1-27). For example, tGase-mediated protein modification has been shown in occur in fibrosis and scarring (Johnson et al., 1999, *J. Am. Soc. Neph.* 10:2146-2157), neurodegenerative diseases including Huntingdon's disease and Alzheimer's disease (Citron et al., 1999, *J. Biol. Chem.* 276:3295-3301), coeliac disease (Marzari et al., 2001, *J. Immunol.* 166:4170-4176), thrombosis (Ariens et al. 2002, *Blood* 100, 743-754), cancer (Van Groningen et al., 1995, *Int. J. Cancer* 60:383-387; Mehta, 1994, *J. Cancer* 58:400-406; Mehta et al., 2002, *J. Natl. Cancer Inst.* 94:1652-1654), AIDS (Amendola at al., 2002, *J. Immunol. Methods* 265:149-159), psoriasis and inflammatory diseases of the joints (Johnson et al., 2001, *Am. J. Pathol.* 159:149-163). Tissue TGase has also been implicated in a number of diseases involving angiogenesis, such as the development of solid tumours and rheumatoid arthritis (Folkman, J., 1995, *Nat. Med* 1, 27-31).

Hence, tissue transglutaminases represent a potential target in the development of new treatments of such diseases and disorders.

The present invention thus seeks to provide novel polypeptides capable of inhibiting the function of tissue transglutaminases for use as therapeutic agents.

SUMMARY OF INVENTION

A first aspect of the invention provides an isolated polypeptide capable of modulating tissue transglutaminase-induced cell behaviour, wherein the polypeptide comprises or consists of:
(a) an amino acid sequence of a heparin-binding site of a tissue transglutaminase, or a functional fragment, variant, fusion or derivative thereof, or a fusion of said fragment, variant or derivative thereof; or
(b) an antibody capable of binding to a heparin-binding site of a tissue transglutaminase, or an antigen-binding fragment or derivative thereof By "modulating" tissue transglutaminase-induced cell behaviour we mean that the polypeptide of the invention is capable of mimicking, inducing or inhibiting (in whole or in part) an effect on cell behaviour attributed to endogenous tissue transglutaminase (preferably in vivo).

By "tissue transglutaminase" we include tissue transglutaminase members of the group of enzymes identified by Enzyme Commission System of Classification No. 2.3.2.13

By "tissue transglutaminase-induced cell behaviour" we include effects on cell signalling, adhesion, spreading and/or migration induced by tissue transglutaminase (optionally when present as a heterocomplex with fibronectin). In particular, we include one or more of the following effects induced by human tissue transglutaminase:
(a) Restored RGD-independent cell adhesion
(b) Enhanced RGD-dependent cell adhesion
(c) Binding of the polypeptide to syndecan-4;
(d) Activation of α5β1 integrin and syndecan-2;
(e) Activation of PKCα, phosphorylated FAK-397, FAK-861 and/or ERK1/2; and/or
(f) Activation of Rho and Src-related cell migration pathway(s) and activation of NF-κB.

The effects of tissue transglutaminase on cell behaviour, and methods of assaying the same, are described in detail in the scientific literature (for example, see Examples below and Wang et al., 2011, *Experimental Cell Research.* 317: 367-381; Wang et al., 2010, *J. Biol. Chem.* 285:40212-40229; Verderio et al., 2003, *J. Biol. Chem.* 278:42604-42614; Balklava et al., 2002, *J. Biol. Chem.* 277:16567-16575; Verderio et al., 1998, *Exp. Cell Res.* 239:119-138; Wang et a, 2010, *Exp. Cell Res.* 317:119-138; Kotsakis et al., 2010, *Amino acids November* 3 [epublication]; Telci et al., 2008, *J. Biol. Chem.* 283:20937-20947; Telci et al., 2009, *J. Biol. Chem.* 284:29547-29558, the disclosures of which are incorporated by reference).

By "heparin-binding site of a tissue transglutaminase" we include the heparan sulfate-binding site of human tissue transglutaminase (see Example A below).

In one embodiment, the heparin-binding site of a tissue transglutaminase comprises or consists of an amino acid sequence of SEQ ID NO: 1:

```
                                              (SEQ ID NO: 1)
LDVNPKFLKNAGRDCSRRSSPVYVGR
```

The term 'amino acid' as used herein includes the standard twenty genetically-encoded amino acids and their corresponding stereoisomers in the 'D' form (as compared to the natural form), omega-amino acids other naturally-occurring amino acids, unconventional amino acids (e.g. α,α-disubstituted amino acids, N-alkyl amino acids, etc.) and chemically derivatised amino acids (see below).

When an amino acid is being specifically enumerated, such as 'alanine' or 'Ala' or 'A', the term refers to both L-alanine and D-alanine unless explicitly stated otherwise. Other unconventional amino acids may also be suitable components for polypeptides of the present invention, as long as the desired functional property is retained by the polypeptide. For the polypeptides shown, each encoded amino acid residue, where appropriate, is represented by a single letter designation, corresponding to the trivial name of the conventional amino acid. In accordance with convention, amino acid sequences are shown in the amino-terminal to carboxy terminal direction.

By "isolated" polypeptide we mean a polypeptide in a form in which it is not found in nature. For example, the polypeptide may be a substantially pure polypeptide produced by recombinant means.

In one embodiment, the polypeptide of the invention is capable of inhibiting the binding of a heparan sulfate proteoglycan to a tissue transglutaminase, in whole or in part. For example, the polypeptides may inhibit the binding by at least 10%, for example at least 20%, 30%, 40%, 50%, 60%, 70%, 80%, 90%, 95% and preferably by 100%.

Methods and assays for determining whether a polypeptide is capable of inhibiting the binding of a heparan sulfate proteoglycan to a transglutaminase are well known in the art (see Examples below).

Advantageously, the polypeptides of the invention are capable of inhibiting the binding of a heparan sulfate proteoglycan to a transglutaminase in vivo.

In another embodiment, the polypeptides of the invention are capable of binding to a heparan sulfate proteoglycan.

In a further embodiment the heparan sulfate proteoglycan is a human heparan sulfate proteoglycan. For example, the heparan sulfate proteoglycan may be a syndecan, such as syndecan-4.

Thus, in one embodiment of the invention, the polypeptide is capable of inhibiting in vivo the binding human syndecan-4 to a human tissue transglutaminase.

In one embodiment, the tissue transglutaminase is a human tissue transglutaminase.

The polypeptides of the invention may be broadly categorised into two subtypes; polypeptides which mimic or otherwise enhance tissue transglutaminase-induced cell behaviour and polypeptides which inhibit or block tissue transglutaminase-induced cell behaviour. By "mimic", in this context, we mean that the polypeptide is capable of inducing one or more of the above changes in cell behaviour induced by tissue transglutaminase (thus, replacing or augmenting the effects induced by endogenous tissue transglutaminase).

In a first subgroup of the polypeptides of the invention, the polypeptide of the invention comprises or consists of an amino acid sequence of SEQ ID NO:1, or a functional fragment, variant, fusion or derivative thereof, or a fusion of said fragment, variant or derivative thereof.

By "functional" in this context we mean that the fragment, variant, fusion or derivative retains, in whole or in part, the ability of the polypeptide of SEQ ID NO:1 to mimic or otherwise enhance tissue transglutaminase-induced cell behaviour. Thus, the polypeptides are capable of binding to the heparan sulfate proteoglycans (such as syndecan-4). Unexpectedly, the inventors found that such polypeptides of the invention are capable of inducing the above stimulatory effects of tissue transglutaminase on cell behaviour.

In addition, the polypeptides may also be capable of blocking the binding of endogenous tissue transglutaminase to heparan sulfate proteoglycans (by competing for the binding moieties on the proteoglycan molecules, thus preventing the binding of endogenous tissue transglutaminase). A possible consequence of such blockade is the inhibition of translocation of tissue transglutaminase across the cell membrane and its deposition into the extracellular matrix (see Examples below).

The polypeptide defined by SEQ ID NO: 1 contains twenty-six amino acids. However, it will be appreciated by persons skilled in the art that the polypeptides of the invention may be of greater or shorter length. For example, the polypeptide may be fewer than 100 amino acids in length, for example fewer than 95, 90, 85, 80, 75, 70, 65, 60, 55, 50, 45, 40, 35, 30, 25, 24, 23, 22, 21, 20, 19, 18, 17, 16, 15, 14, 13, 12, 11, 10 or fewer amino acids in length. Likewise, the polypeptide may be greater than 10 amino acids in length, for example greater than 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or greater amino acids in length. For example, the polypeptide may be between 10 and 50 amino acids in length, for example between 15 and 30 amino acids in length, e.g. 15, 16, 17, 18, 19, 20, 21, 22, 23, 24, 25, 26, 27, 28, 29 or 30 amino acids in length.

Thus, in one embodiment of the first aspect of the invention, the polypeptide comprises or consists of a fragment of the amino acid sequence of SEQ ID NO: 1, or a functional variant, fusion or derivative thereof, or a fusion of said variant or derivative thereof. For example, the polypeptide may comprise or consist of a fragment of the amino acid sequence of SEQ ID NO: 1.

By "fragment" we include at least 5 contiguous amino acids of the amino acid sequence of SEQ ID NO: 1, for example at least 6, 7, 8, 9, 10, 11, 12, 13, 14, 15, 16, 17, 18, 19, 20, 21, 22, 23, 24, 25 or 26 contiguous amino acids thereof.

In one embodiment, the polypeptide comprises or consists of the amino acid sequence of SEQ ID NO: 2, or a functional variant, fusion or derivative thereof, or a fusion of said variant or derivative thereof:

```
                                              (SEQ ID NO: 2)
NPKFLKNAGRDCSRRSS
```

For example, the polypeptide may consist of the amino acid sequence of SEQ ID NO: 2.

This polypeptide is derived from that of SEQ ID NO.1 but omits several of the terminal hydrophobic amino acids, in order to optimise its folding and solubility properties.

In another embodiment, the polypeptide comprises or consists of the amino acid sequence of SEQ ID NO:27 or 29, or a functional variant, fusion or derivative thereof, or a fusion of said variant or derivative thereof (see Examples below).

In a further embodiment, the polypeptide comprises or consists of the amino acid sequence of SEQ ID NO: 3, or a functional variant, fusion or derivative thereof, or a fusion of said variant or derivative thereof

GRDCSRRSS. (SEQ ID NO: 3)

In a further embodiment, the polypeptide comprises or consists of a variant of the amino acid sequence of SEQ ID NO: 1 or 2 or of a functional fragment, fusion or derivative thereof, or a fusion of said fragment or derivative thereof. Thus, the polypeptide may comprise or consist of a variant of the amino acid sequence of SEQ ID NO: 1 or 2.

By "variant" we mean that the polypeptide does not share 100% amino acid sequence identity with SEQ ID NO: 1 or 2, i.e. the polypeptide may comprise or consist of an amino acid sequence in which one or more amino acids is mutated, deleted, added and/or otherwise modified relative to the amino acid sequence of SEQ ID NO: 1 or 2. By "modified" we include that the amino acid at a specified position is altered compared to the corresponding amino acid in the polypeptide according to SEQ ID NO: 1 or 2. For example, the amino acid at the specified position may be non-natural, deleted, substituted or may be the site of an insertion/addition of one or more amino acids. It will be appreciated by persons skilled in the art that the substitutions may be conservative or non-conservative. By "conservatively substituted" we mean a substitution of one amino acid with another with similar properties (size, hydrophobicity, etc), such that the function of the polypeptide is not significantly altered. Thus, by "conservative substitutions" is intended combinations such as Gly, Ala; Val, Ile, Leu; Asp, Glu; Asn, Gln; Ser, Thr; Lys, Arg; and Phe, Tyr.

In one embodiment, the polypeptide comprises or consists of an amino acid sequence with at least 60% identity to the amino acid sequence of SEQ ID NO: 1 or 2, more preferably at least 70% or 80% or 85% or 90% identity to said sequence, and most preferably at least 95%, 96%, 97%, 98% or 99% identity to said amino acid sequence.

Percent identity can be determined by methods well known in the art, for example using the LALIGN program (Huang and Miller, *Adv. Appl. Math.* (1991) 12:337-357) at the Expasy facility site
(world-wide-web at ch.embnet.org/software/LALIGN form.html)
using as parameters the global alignment option, scoring matrix BLOSUM62, opening gap penalty −14, extending gap penalty −4.

Alternatively, the percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally.

Variant forms of a known polypeptide can be produced using techniques well known in the art (see Sambrook & Russell, 2000, *Molecular Cloning, A Laboratory Manual*, Third Edition, Cold Spring Harbor, N.Y., which is incorporated herein by reference). For example, point mutations may be introduced at specific amino acid residues by site-directed mutagenesis (see Sambrook & Russell, supra, Chapter 13). Additional methods for generating variants of a parent polynucleotide include DNA shuffling and other methods of directed evolution.

In a further embodiment of the first aspect of the invention, the polypeptide comprises or consists of a fusion of the amino acid sequence of SEQ ID NO: 1 or 2, or of a functional fragment or derivative thereof. For example, the polypeptide may comprise or consist of a fusion of the amino acid sequence of SEQ ID NO: 1 or 2.

By 'fusion' we include a polypeptide as defined above fused to any other polypeptide. For example, the said polypeptide may be fused to a polypeptide such as glutathione-S-transferase (GST) or protein A in order to facilitate purification of said polypeptide. Examples of such fusions are well known to those skilled in the art. Similarly, the said polypeptide may be fused to an oligo-histidine tag such as His6 or to an epitope recognised by an antibody such as the well-known Myc tag epitope. Fusions to any fragment, variant or derivative of said polypeptide are also included in the scope of the invention. It will be appreciated that fusions (or variants or derivatives thereof) which retain desirable properties, namely anticancer activity are preferred. It is also particularly preferred if the fusions are ones which are suitable for use in the methods described herein.

Alternatively, or in addition, the fusion may comprise a further portion which confers a desirable feature on the said polypeptide of the invention; for example, the portion may be useful in detecting or isolating the polypeptide, or promoting cellular uptake of the polypeptide. The portion may be, for example, a biotin moiety, a radioactive moiety, a fluorescent moiety, for example a small fluorophore or a green fluorescent protein (GFP) fluorophore, as well known to those skilled in the art. The moiety may be an immunogenic tag, for example a Myc tag, as known to those skilled in the art or may be a lipophilic molecule or polypeptide domain that is capable of promoting cellular uptake of the polypeptide, as known to those skilled in the art.

In one embodiment of the first aspect of the invention, the polypeptides comprise or consist of natural L-amino acids. However, in a further embodiment, the polypeptide comprises or consists of a derivative of the amino acid sequence of SEQ ID NO: 1 or 2 or of a functional fragment, variant or fusion thereof, or a fusion of said fragment or variant thereof. For example, the polypeptide may comprise or consist of a derivative of the amino acid sequence of SEQ ID NO: 1 or 2.

Chemical derivatives of one or more amino acids may be achieved by reaction with a functional side group. Such derivatised molecules include, for example, those molecules in which free amino groups have been derivatised to form amine hydrochlorides, p-toluene sulphonyl groups, carboxybenzoxy groups, t-butyloxycarbonyl groups, chloroacetyl groups or formyl groups. Free carboxyl groups may be derivatised to form salts, methyl and ethyl esters or other types of esters and hydrazides. Free hydroxyl groups may be derivatised to form O-acyl or O-alkyl derivatives. Also included as chemical derivatives are those peptides which contain naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine and ornithine for lysine. Derivatives also include peptides containing one or more additions or deletions as long as the requisite activity is maintained. Other included modifications are amidation, amino terminal acylation (e.g. acetylation or thioglycolic acid amidation), terminal carboxylamidation (e.g. with ammonia or methylamine), and the like terminal modifications.

It will be further appreciated by persons skilled in the art that peptidomimetic compounds may also be useful. Thus, by 'polypeptide' we include peptidomimetic compounds which exhibit anti-cancer activity. The term 'peptidomimetic' refers to a compound that mimics the conformation and desirable features of a particular polypeptide as a therapeutic agent.

For example, the polypeptides described herein include not only molecules in which amino acid residues are joined by peptide (—CO—NH—) linkages but also molecules in which the peptide bond is reversed. Such retro-inverso peptidomimetics may be made using methods known in the art, for example such as those described in Meziere et al. (1997) *J. Immunol.* 159, 3230-3237, the relevant disclosures in which document are hereby incorporated by reference. This approach involves making pseudopeptides containing changes involving the backbone, and not the orientation of side chains. Retro-inverse peptides, which contain NH—CO bonds instead of CO—NH peptide bonds, are much more resistant to proteolysis. Alternatively, the polypeptide of the invention may be a peptidomimetic compound wherein one or more of the amino acid residues are linked by a -y(CH$_2$NH)— bond in place of the conventional amide linkage.

In a further alternative, the peptide bond may be dispensed with altogether provided that an appropriate linker moiety which retains the spacing between the carbon atoms of the amino acid residues is used; it is particularly preferred if the linker moiety has substantially the same charge distribution and substantially the same planarity as a peptide bond.

It will be appreciated that the polypeptide may conveniently be blocked at its N- or C-terminus so as to help reduce susceptibility to exoproteolytic digestion, e.g. by amidation. A variety of encoded or modified amino acids such as D-amino acids and N-methyl amino acids have also been used to modify mammalian peptides. In addition, a presumed bioactive conformation may be stabilised by a covalent modification, such as cyclisation or by incorporation of lactam or other types of bridges, for example see Veber et al., 1978, *Proc. Natl. Acad. Sci*, USA 75:2636 and Thursell et al., 1983, *Biochem. Biophys. Res. Comm.* 111: 166, the relevant disclosures in which documents are hereby incorporated by reference.

A common theme among many of the synthetic strategies has been the introduction of some cyclic moiety into a peptide-based framework. The cyclic moiety restricts the conformational space of the peptide structure and this frequently results in an increased affinity of the peptide for a particular biological receptor. An added advantage of this strategy is that the introduction of a cyclic moiety into a peptide may also result in the peptide having a diminished sensitivity to cellular peptidases.

Thus, preferred polypeptides comprise terminal cysteine amino acids. Such a polypeptide may exist in a heterodetic cyclic form by disulphide bond formation of the mercaptide groups in the terminal cysteine amino acids or in a homodetic form by amide peptide bond formation between the terminal amino acids. As indicated above, cyclising small peptides through disulphide or amide bonds between the N- and C-terminus cysteines may circumvent problems of affinity and half-life sometime observed with linear peptides, by decreasing proteolysis and also increasing the rigidity of the structure, which may yield higher affinity compounds. Polypeptides cyclised by disulphide bonds have free amino and carboxy-termini which still may be susceptible to proteolytic degradation, while peptides cyclised by formation of an amide bond between the N-terminal amine and C-terminal carboxyl and hence no longer contain free amino or carboxy termini. Thus, the peptides of the present invention can be linked either by a C—N linkage or a disulphide linkage.

The present invention is not limited in any way by the method of cyclisation of peptides, but encompasses peptides whose cyclic structure may be achieved by any suitable method of synthesis. Thus, heterodetic linkages may include, but are not limited to formation via disulphide, alkylene or sulphide bridges. Methods of synthesis of cyclic homodetic peptides and cyclic heterodetic peptides, including disulphide, sulphide and alkylene bridges, are disclosed in U.S. Pat. No. 5,643,872. Other examples of cyclisation methods are discussed and disclosed in U.S. Pat. No. 6,008, 058, the relevant disclosures in which documents are hereby incorporated by reference.

A further approach to the synthesis of cyclic stabilised peptidomimetic compounds is ring-closing metathesis (RCM). This method involves steps of synthesising a peptide precursor and contacting it with an RCM catalyst to yield a conformationally restricted peptide. Suitable peptide precursors may contain two or more unsaturated C—C bonds. The method may be carried out using solid-phase-peptide-synthesis techniques. In this embodiment, the precursor, which is anchored to a solid support, is contacted with a RCM catalyst and the product is then cleaved from the solid support to yield a conformationally restricted peptide.

Another approach, disclosed by D. H. Rich in *Protease Inhibitors*, Barrett and Selveson, eds., Elsevier (1986; the relevant disclosures in which document are hereby incorporated by reference), has been to design peptide mimics through the application of the transition state analogue concept in enzyme inhibitor design. For example, it is known that the secondary alcohol of staline mimics the tetrahedral transition state of the scissile amide bond of the pepsin substrate.

In summary, terminal modifications are useful, as is well known, to reduce susceptibility by proteinase digestion and therefore to prolong the half-life of the peptides in solutions, particularly in biological fluids where proteases may be present. Polypeptide cyclisation is also a useful modification and is preferred because of the stable structures formed by cyclisation and in view of the biological activities observed for cyclic peptides.

Thus, in one embodiment the polypeptide, or fragment, variant, fusion or derivative thereof, is cyclic.

However, in an alternative embodiment, the polypeptide, or fragment, variant, fusion or derivative thereof, is linear.

In the second subgroup of the polypeptides of the invention, the polypeptide of the invention comprises or consists of an antibody capable of binding to the heparin-binding domain of a tissue transglutaminase, or an antigen-binding fragment thereof.

In one embodiment, the heparin-binding site of a tissue transglutaminase comprises or consists of an amino acid sequence of SEQ ID NO: 1.

Such polypeptides may interfere with the binding of heparan sulfate chains to the heparin-binding domain of the tissue transglutaminase by attaching to and blocking the function of the heparin-binding domain of the tissue tr glutaminase (which contains an amino acid sequence of SEQ ID NO:1). Thus, the polypeptides may bind to the tissue transglutaminase and, in so doing, block its ability to bind to the heparan sulfate proteoglycan.

In one embodiment, the antibody of antigen-binding fragment thereof is capable of binding to the heparin-binding domain of a tissue transglutaminase (e.g. SEQ ID NO:1) in vivo.

In one embodiment, the polypeptide comprises or consists of an antibody capable of binding to the heparin-binding domain of a tissue transglutaminase (e.g. SEQ ID NO:1).

In an alternative embodiment, the polypeptide comprises or consists of an antigen-binding fragment of an antibody capable of binding to the heparin-binding domain of a tissue transglutaminase (e.g. SEQ ID NO:1).

It will be appreciated by persons skilled in the art that the antibody-related polypeptides of the invention may also serve to inhibit translocation of the tissue transglutaminase across the cell membrane and into the matrix (by competing for the binding sites on the endogenous tissue transglutaminase molecules, thus preventing them from binding to heparan sulfate proteoglycans such as syndecan-4).

By "antibody" we include substantially intact antibody molecules, as well as chimaeric antibodies, humanised antibodies, human antibodies (wherein at least one amino acid is mutated relative to the naturally occurring human antibodies), single chain antibodies, bispecific antibodies, antibody heavy chains, antibody light chains, homodimers and heterodimers of antibody heavy and/or light chains, and antigen binding fragments and derivatives of the same.

By "antigen-binding fragment" we mean a functional fragment of an antibody that is capable of binding to an amino acid sequence of SEQ ID NO:1.

Preferably, the antigen-binding fragment is selected from the group consisting of Fv fragments (e.g. single chain Fv and disulphide-bonded Fv), Fab-like fragments (e.g. Fab fragments, Fab' fragments and F(ab)$_2$ fragments), single variable domains (e.g. V$_H$ and V$_L$ domains) and domain antibodies (dAbs, including single and dual formats [i.e. dAb-linker-dAb]).

The potential advantages of using antibody fragments, rather than whole antibodies, are several-fold. The smaller size of the fragments may lead to improved pharmacological properties, such as better penetration of solid tissue. Moreover, antigen-binding fragments such as Fab, Fv, ScFv and dAb antibody fragments can be expressed in and secreted from E. coli, thus allowing the facile production of large amounts of the said fragments.

Also included within the scope of the invention are modified versions of antibodies and antigen-binding fragments thereof, e.g. modified by the covalent attachment of polyethylene glycol or other suitable polymer.

Methods of generating antibodies and antibody fragments are well known in the art. For example, antibodies may be generated via any one of several methods which employ induction of in vivo production of antibody molecules, screening of immunoglobulin libraries (Orlandi. et al, 1989. Proc. Natl. Acad. Sci. U.S.A. 86:3833-3837; Winter et at, 1991, Nature 349:293-299) or generation of monoclonal antibody molecules by cell lines in culture. These include, but are not limited to, the hybridoma technique, the human B-cell hybridoma technique, and the Epstein-Barr virus (EBV)-hybridoma technique (Kohler et at, 1975. Nature 256:4950497; Kozbor et al., 1985. J. Immunol. Methods 81:31-42; Cote et al., 1983. Proc. Natl. Acad. Sci. USA 80:2026-2030; Cole et al., 1984. Mol. Cell. Biol. 62:109-120).

Suitable monoclonal antibodies to selected antigens may be prepared by known techniques, for example those disclosed in "*Monoclonal Antibodies: A manual of techniques*", H Zola (CRC Press, 1988) and in "*Monoclonal Hybridoma Antibodies: Techniques and Applications*", J G R Hurrell (CRC Press, 1982).

Antibody fragments can be obtained using methods well known in the art (see, for example, Harlow & Lane, 1988, "*Antibodies: A Laboratory Manual*", Cold Spring Harbor Laboratory, New York). For example, antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Alternatively, antibody fragments can be obtained by pepsin or papain digestion of whole antibodies by conventional methods.

It will be appreciated by persons skilled in the art that for human therapy or diagnostics, human or humanised antibodies are preferably used. Humanised forms of non-human (e.g. murine) antibodies are genetically engineered chimaeric antibodies or antibody fragments having preferably minimal-portions derived from non-human antibodies. Humanised antibodies include antibodies in which complementary determining regions of a human antibody (recipient antibody) are replaced by residues from a complementary determining region of a non human species (donor antibody) such as mouse, rat of rabbit having the desired functionality. In some instances, Fv framework residues of the human antibody are replaced by corresponding non-human residues. Humanised antibodies may also comprise residues which are found neither in the recipient antibody nor in the imported complementarity determining region or framework sequences. In general, the humanised antibody will comprise substantially all of at least one, and typically two, variable domains, in which all or substantially all of the complementarity determining regions correspond to those of a non human antibody and all, or substantially all, of the framework regions correspond to those of a relevant human consensus sequence. Humanised antibodies optimally also include at least a portion of an antibody constant region, such as an Fc region, typically derived from a human antibody (see, for example, Jones et al., 1986. Nature 321:522-525; Riechmann et al., 1988, Nature 332:323-329; Presta, 1992, Curr. Op. Struct. Biol. 2:593-596).

Methods for humanising non-human antibodies are well known in the art. Generally, the humanised antibody has one or more amino acid residues introduced into it from a source which is non-human. These non-human amino acid residues, often referred to as imported residues, are typically taken from an imported variable domain. Humanisation can be essentially performed as described (see, for example, Jones et al., 1986, Nature 321:522-525; Reichmann et al., 1988. Nature 332:323-327; Verhoeyen et al., 1988, Science 239: 1534-15361; U.S. Pat. No. 4,816,567) by substituting human complementarity determining regions with corresponding rodent complementarity determining regions. Accordingly, such humanised antibodies are chimaeric antibodies, wherein substantially less than an intact human variable domain has been substituted by the corresponding sequence from a non-human species. In practice, humanised antibodies may be typically human antibodies in which some complementarity determining region residues and possibly some framework residues are substituted by residues from analogous sites in rodent antibodies.

Human antibodies can also be identified using various techniques known in the art, including phage display libraries (see, for example, Hoogenboom & Winter, 1991, *J. Mol. Biol.* 227:381; Marks et al., 1991, *J. Mol. Biol.* 222:581; Cole et al., 1985, In: *Monoclonal antibodies and Cancer Therapy*, Alan R. Liss, pp. 77; Boerner et al., 1991. *J. Immunol.* 147:86-95).

Once suitable antibodies are obtained, they may be tested for activity, for example by ELISA.

In one embodiment of the first aspect of the invention, the polypeptide is modified to prolong its half-life in vivo. Any one or more of the following known methods of improving the half-life of proteins may be used for this purpose:

(a) PEGylation

A widely used method for improving the half-life of proteins is the covalent linking of polyethylene glycol (PEG) moieties to the protein. PEGs are water-soluble polymers that due to their large hydrodynamic volume create a shield around the pegylated drug [Molineux, G., *Pegylation: engineering improved pharmaceuticals for enhanced therapy*. Cancer Treat Rev, 2002. 28 Suppl A: p. 13-6]. Pegylated proteins exhibit a decreased renal clearance and proteolysis, reduced toxicity, reduced immunogenicity and an increased solubility [Veronese, F. M. and J. M. Harris, *Introduction and overview of peptide and protein pegylation*. Adv Drug Deliv Rev, 2002. 54(4): p. 453-6., Chapman, A. P., *PEGylated antibodies and antibody fragments for improved therapy: a review*. Adv Drug Deliv Rev, 2002. 54(4): p. 531-45.]. Pegylation has been employed for several protein-based drugs including the first pegylated molecules asparaginase and adenosine deaminase [Veronese, F. M. and J. M. Harris, *Introduction and overview of peptide and protein pegylation*. Adv Drug Deliv Rev, 2002. 54(4): p. 453-6., Veronese, F. M. and G. Pasut, *PEGylation, successful approach to drug delivery*. Drug Discov Today, 2005. 10(21): p. 1451-8.].

In order to obtain a successfully pegylated protein, with a maximally increased half-life and retained biological activity, several parameters that may affect the outcome are of importance and should be taken into consideration. The PEG molecules may differ, and PEG variants that have been used for pegylation of proteins include PEG and monomethoxy-PEG. In addition, they can be either linear or branched [Wang, Y. S., et al., *Structural and biological characterization of pegylated recombinant interferon alpha-2b and its therapeutic implications*. Adv Drug Deliv Rev, 2002. 54(4): p. 547-70]. The size of the PEG molecules used may vary and PEG moieties ranging in size between 1 and 40 kDa have been linked to proteins [Wang, Y. S., et al., *Structural and biological characterization of pegylated recombinant interferon alpha-2b and its therapeutic implications*. Adv Drug Deliv Rev, 2002. 54(4): p. 547-70., Sato, H., *Enzymatic procedure for site-specific pegylation of proteins*. Adv Drug Deliv Rev, 2002. 54(4): p. 487-504, Bowen, S., et al., *Relationship between molecular mass and duration of activity of polyethylene glycol conjugated granulocyte colony-stimulating factor mutein*. Exp Hematol, 1999. 27(3): p. 425-32, Chapman, A. P., et al., *Therapeutic antibody fragments with prolonged in vivo half-lives*. Nat Biotechnol, 1999. 17(8): p. 780-3]. In addition, the number of PEG moieties attached to the protein may vary, and examples of between one and six PEG units being attached to proteins have been reported [Wang, Y. S., et al., *Structural and biological characterization of pegylated recombinant interferon alpha-2b and its therapeutic implications*. Adv Drug Deliv Rev, 2002. 54(4): p. 547-70., Bowen, S., at al., *Relationship between molecular mass and duration of activity of polyethylene glycol conjugated granulocyte colony-stimulating factor mutein*. Exp Hematol, 1999. 27(3): p. 425-32]. Furthermore, the presence or absence of a linker between PEG as well as various reactive groups for conjugation have been utilised. Thus, PEG may be linked to N-terminal amino groups, or to amino acid residues with reactive amino or hydroxyl groups (Lys, His, Ser, Thr and Tyr) directly or by using γ-amino butyric acid as a linker. In addition, PEG may be coupled to carboxyl (Asp, Glu, C-terminal) or sulfhydryl (Cys) groups. Finally, Gln residues may be specifically pegylated using the enzyme transglutaminase and alkylamine derivatives of PEG has been described [Sato, H., *Enzymatic procedure for site-specific pegylation of proteins*. Adv Drug Deliv Rev, 2002. 54(4): p. 487-504].

It has been shown that increasing the extent of pegylation results in an increased in vivo half-life. However, it will be appreciated by persons skilled in the art that the pegylation process will need to be optimised for a particular protein on an individual basis.

PEG may be coupled at naturally occurring disulphide bonds as described in WO 2005/007197. Disulfide bonds can be stabilised through the addition of a chemical bridge which does not compromise the tertiary structure of the protein. This allows the conjugating thiol selectivity of the two sulphurs comprising a disulfide bond to be utilised to create a bridge for the site-specific attachment of PEG. Thereby, the need to engineer residues into a peptide for attachment of to target molecules is circumvented.

A variety of alternative block copolymers may also be covalently conjugated as described in WO 2003/059973. Therapeutic polymeric conjugates can exhibit improved thermal properties, crystallisation, adhesion, swelling, coating, pH dependent conformation and biodistribution. Furthermore, they can achieve prolonged circulation, release of the bioactive in the proteolytic and acidic environment of the secondary lysosome after cellular uptake of the conjugate by pinocytosis and more favourable physicochemical properties due to the characteristics of large molecules (e.g. increased drug solubility in biological fluids), Co-block copolymers, comprising hydrophilic and hydrophobic blocks, form polymeric micelles in solution. Upon micelle disassociation, the individual block copolymer molecules are safely excreted.

(b) Fusion Proteins

IgG Fusion Proteins

Human immunoglobulin G (IgG) molecules have circulating half-lives of approximately 20 days. The Fc portion of IgG molecules have been extensively used for the creation of fusion proteins consisting of an Fc part and a protein with a therapeutic use. Such fusion proteins exhibit a prolonged half-life compared to their Fc-lacking counterparts. For example, this strategy was used for the development of etanercept, an anti-rheumatic drug composed of a fusion protein between the soluble human p75 tumour necrosis factor receptor and the Fc portion of human IgG [Goldenberg, M. M., *Etanercept, a novel drug for the treatment of patients with severe, active rheumatoid arthritis*. Clin Ther, 1999. 21(1): p. 75-87; discussion 1-2].

Fc-linked proteins are produced by creating fusion proteins between Fc and the protein of interest by standard genetic engineering protocols. The Fc group is fused to the C-terminus of the protein of interest. Due to the presence of cysteine residues in the hinge region of IgG, Fc fusion proteins are expressed as disulfide-linked homodimers. This further increases their effective size and circulating half-lives. In addition, homodimeric constructs may have an increased functional activity due to improved avidity for its receptor/ligand compared to the corresponding monomeric form.

Human Serum Albumin Fusion Proteins

Human serum albumin (HSA) is the most abundant naturally occurring blood protein in the circulation and has a half-life of 19 days [Osborn, B. L., et al., *Pharmacokinetic and pharmacodynamic studies of a human serum albumin-interferon-alpha fusion protein in cynomolgus monkeys*. J Pharmacol Exp Ther, 2002. 303(2): p. 540-8]. Thus, HSA is a suitable fusion partner for the creation of fusion proteins with improved half-life. HSA fusion proteins exhibit a prolonged half-life due to the capability of HSA to stabilize the protein towards proteolysis and increasing the residence time in the body [Veronese, F. M. and J. M. Harris, *Introduction and overview of peptide and protein pegylation*. Adv Drug Deliv Rev, 2002. 54(4): p. 453-6]. HSA fusion proteins, including IL-2, IFN-α and -β and growth hormone (GH), have been produced and shown to have improved pharmacokinetic properties. Albuferon (HSA-IFN-α) and albutropin (HSA-GH) exhibit half-lives that are 18 and 6 times longer in cynomolgus monkeys, respectively, than the respective counterparts lacking an HSA group [Osborn, B. L., et al., *Pharmacokinetic and pharmacodynamic studies of a human serum albumin-interferon-alpha fusion protein in cynomolgus monkeys*. J Pharmacol Exp Ther, 2002. 303(2): p. 540-8, Osborn, B. L., et al., *Albutropin: a growth hormone-albumin fusion with improved pharmacokinetics and pharmacodynamics in rats and monkeys*. Eur J Pharmacol, 2002. 456(1-3): p. 149-58].

HSA-linked proteins are produced by creating fusion proteins between HSA and the protein of interest by standard genetic engineering protocols. The HSA group may be added at either the N- or the C-terminus. Since the modification is added to the terminus of the protein, the risk of interfering with the structure of the protein and thus with its function is considerably less compared to modifications such as pegylation in the interior of the protein. In addition, the chance of avoiding interference with the active site of the protein is increased by the fact that the HSA group may be added at either the N- or C-terminus of the protein of interest [Osborn, B. L., et al., *Pharmacokinetic and pharmacodynamic studies of a human serum albumin-interferon-alpha fusion protein in cynomolgus monkeys*. J Pharmacol Exp Ther, 2002. 303(2): p. 540-8, Osborn, B. L., et al., *Albutropin: a growth hormone-albumin fusion with improved pharmacokinetics and pharmacodynamics in rats and monkeys*. Eur J Pharmacol, 2002. 456(1-3): p. 149-58, Syed, S., K. E. Kelly, and W. P. Sheffield, *Inhibition of thrombin by hirudin genetically fused to wild-type or mutant antithrombin*. Thromb Res, 1996. 84(6): p. 419-29], depending on which is more likely to result in a fusion protein with maintained biological activity. Thus, in the case of albuferon and albutropin, the C-terminus of the HSA was fused with the N-terminus of IFN-α or GH, respectively, creation of a functionally active hirudin-HSA fusion protein, the HSA group had to be fused to the C-terminus of hirudin. These results indicate that the properties of the target protein determine whether fusion at the N- or C-terminus is optimal.

(c) Glycosylation

The introduction of new sialic acid-containing carbohydrates into a protein (glycoengineering) has been shown to improve in vivo half-life. This method may be used for naturally glycosylated proteins or for proteins that normally lack glycosylation [Elliott, S., et al., *Enhancement of therapeutic protein in vivo activities through glycoengineering*. Nat Biotechnol, 2003. 21(4): p. 414-21].

Glycosylation of proteins may be in the form of N-linked or O-linked carbohydrates. N-linked carbohydrates are typically attached to consensus sequences (Asn-X-Ser/Thr) where X is any amino acid except proline. 0-glycosylation occurs at Ser/Thr residues.

For the production of glycosylated proteins, the introduction of novel glycosylation sites may be required. For glycosylation to occur, expression may be performed in yeast, insect or mammalian cell systems. However, the glycosylation pattern in yeast cells is different than mammalian cells, generating hyper-glycosylated proteins, associated with a risk of increased immunogenicity. In contrast, insect cells may be preferred since the glycosylation pattern is similar to that in mammalian cells whereas cell cycles are shorter and therefore expression process faster. Darbepoetin-α is an example of a modified human erythropoetin expressed in CHO cells. It contains two extra N-glycosylation sites, resulting in a three times improved in vivo half-life [Elliott, S., et al., *Enhancement of therapeutic protein in vivo activities through glycoengineering*. Nat Biotechnol, 2003. 21(4): p. 414-21].

An alternative method of glycosylation is the chemical addition of carbohydrate groups to proteins. In this method, the protein is expressed naked, e.g. in *E. coli*. Following expression and purification, the protein is glycosylated in a fully synthetic cell-free process. The method offers great flexibility in terms of number, size and type of carbohydrate to be added.

(d) Fatty Acid Acylation/Myristoylation

Fatty acids have a high affinity and high capacity of HSA binding. This characteristic can be utilized for improving the half-life of proteins. Thus, fatty acyl can be attached to amino acids of proteins, thus generating fatty acyl acylated proteins. Upon reaching the circulation, the fatty acyl group is capable of binding to circulating HSA, resulting in an improved in vivo half-life of the protein.

This method was used for the development of Insulin detemir, which was fatty acyl acylated with myristate at $Lys^{B29}$ by treatment of insulin with fatty acid hydroxyl-succinimide esters in dimethyl formamide/DMSO [Kurtzhals, P., et al., *Albumin binding of insulins acylated with fatty acids: characterization of the ligand-protein interaction and correlation between binding affinity and timing of the insulin effect in vivo*. Biochem J, 1995. 312 (Pt 3): p. 725-31, Hamilton-Wessler, M., et al., *Mechanism of protracted metabolic effects of fatty acid acylated insulin, NN304, in dogs: retention of NN304 by albumin*. Diabetologia, 1999. 42(10): p. 1254-63]. This generated an insulin analogue with increased in vivo half-life due to binding of HSA.

(e) Dextran

Dextran results in an immobilization of the protein, resulting in a slow release and thereby improves the half-life of the protein. Dextran-streptokinase, has been marketed in Russia for thrombolytic therapy. In addition, insulin, somatostatin (which is used for therapy and diagnosis of tumours expressing somatostatin receptors) and the ribosome-inactivating drug trichosantin conjugated to dextran, had a significantly improved half-lives [Baudys, M., et al., *Extending insulin action in vivo by conjugation to carboxymethyl dextran*. Bioconjug Chem, 1998. 9(2): p. 176-83, Chan, W. L., et al., *Lowering of trichosanthin immunogenicity by site-specific coupling to dextran*. Biochem Pharmacol, 1999. 57(8): p. 927-34, Wulbrand, U., et al., *A novel somatostatin conjugate with a high affinity to all five somatostatin receptor subtypes*. Cancer, 2002. 94(4 Supply p. 1293-7].

In addition to protein-based pharmaceuticals, dextran has been used for improving the half-life of antibiotics and cytotoxic drugs [Yura, H., et al., *Synthesis and pharmacokinetics of a novel macromolecular prodrug of Tacrolimus (FK506), FK506-dextran conjugate*. J Control Release, 1999. 57(1): p. 87-99, Nakashima, M., et al., *In vitro characteristics and in vivo plasma disposition of cisplatin conjugated with oxidized and dicarboxymethylated dextrans*. Biol Pharm Bull, 1999. 22(7): p. 756-61, Kim, D. S., Y. J. Jung, and Y. M. Kim, *Synthesis and properties of dextran-linked ampicillin*. Drug Dev Ind Pharm, 2001. 27(1): p. 97-101].

Dextran conjugation is carried out by reductive amination using periodate-activated dextran or by the use of cyanogens bromide [Wulbrand, U., et al., *A novel somatostatin conjugate with a high affinity to all five somatostatin receptor subtypes*. Cancer, 2002. 94(4 Suppl): p. 1293-7, Kim, D. S., Y. J. Jung, and Y. M. Kim, *Synthesis and properties of dextran-linked ampicillin*. Drug Dev Ind Pharm, 2001. 27(1): p. 97-101]. The dextran used may vary in size, and dextran ranging from 9 to 82 kDa have been used [Kim, D. S., Y. J. Jung, and Y. M. Kim, *Synthesis and properties of dextran-linked ampicillin*. Drug Dev Ind Pharm, 2001. 27(1): p. 97-101, Behe, M., et al., *Biodistribution, blood half-life, and receptor binding of a somatostatin-dextran conjugate*. Med Oncol, 2001. 18(1): p. 59-64].

In addition to improving the half-life of drugs, dextran conjugation may also reduce immunogenicity [Chan, W. L., et al., *Lowering of trichosanthin immunogenicity by site-specific coupling to dextran*. Biochem Pharmacol, 1999. 57(8): p. 927-34].

The polypeptides of the first aspect of the invention may be made by methods well known to persons skilled in the art (for example, see Sambrook & Russell, 2000, *Molecular Cloning, A Laboratory Manual*, Third Edition, Cold Spring Harbor, N.Y., which is incorporated herein by reference).

In brief, expression vectors may be constructed comprising a nucleic acid molecule which is capable, in an appropriate host, of expressing the polypeptide encoded by the nucleic acid molecule.

A variety of methods have been developed to operably link nucleic acid molecules, especially DNA, to vectors, for example, via complementary cohesive termini. For instance, complementary homopolymer tracts can be added to the DNA segment to be inserted into the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, e.g. generated by endonuclease restriction digestion, is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerising activities.

The combination of these activities therefore generates blunt-ended DNA segments. The blunt-ended segments are then incubated with a larger molar excess of linker molecules in the presence of an enzyme that is able to catalyse the ligation of blunt-ended DNA molecules, such as bacteriophage T4 DNA ligase, Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease site are commercially available from a number of sources including International Biotechnologies Inc., New Haven, Conn., USA.

A desirable way to modify the DNA encoding the polypeptide of the invention is to use PCR. This method may be used for introducing the DNA into a suitable vector, for example by engineering in suitable restriction sites, or it may be used to modify the DNA in other useful ways as is known in the art.

In this method the DNA to be enzymatically amplified is flanked by two specific primers which themselves become incorporated into the amplified DNA. The said specific primers may contain restriction endonuclease recognition sites which can be used for cloning into expression vectors using methods known in the art.

The DNA (or in the case of retroviral vectors, RNA) is then expressed in a suitable host to produce a polypeptide comprising the compound of the invention. Thus, the DNA encoding the polypeptide may be used in accordance with known techniques, appropriately modified in view of the teachings contained herein, to construct an expression vector, which is then used to transform an appropriate host cell for the expression and production of the compound of the invention. Such techniques include those disclosed in U.S. Pat. No. 4,440,859 issued 3 Apr. 1984 to Rutter et al, U.S. Pat. No. 4,530,901 issued 23 Jul. 1985 to Weissman, U.S. Pat. No. 4,582,800 issued 15 Apr. 1986 to Crowl, U.S. Pat. No. 4,677,063 issued 30 Jun. 1987 to Mark et al, U.S. Pat. No. 4,678,751 issued 7 Jul. 1987 to Goeddel, U.S. Pat. No. 4,704,362 issued 3 Nov. 1987 to Itakura et al, U.S. Pat. No. 4,710,463 issued 1 Dec. 1987 to Murray, U.S. Pat. No. 4,757,006 issued 12 Jul. 1988 to Toole, Jr. et al, U.S. Pat. No. 4,766,075 issued 23 Aug. 1988 to Goeddel et al and U.S. Pat. No. 4,810,648 issued 7 Mar. 1989 to Stalker (which is incorporated herein by reference).

The DNA (or in the case or retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the expression vector of the invention are then cultured for a sufficient time and under appropriate conditions known to those skilled in the art in view of the teachings disclosed herein to permit the expression of the polypeptide, which can then be recovered.

Many expression systems are known, including bacteria (for example, *E. coli* and *Bacillus subtilis*), yeasts (for example *Saccharomyces cerevisiae*), filamentous fungi (for example *Aspergillus*), plant cells, animal cells and insect cells.

The vectors typically include a prokaryotic replicon, such as the ColE1 ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA. Particularly preferred prokaryotic vector plasmids include the pET system (Novagene), pRSET and pHIP (Invitrogen, California, USA).

A typical mammalian cell vector plasmid is pSVL. This vector uses the SV40 late promoter to drive expression of cloned genes, the highest level of expression being found in T antigen-producing cells, such as COS-1 cells.

An example of an inducible mammalian expression vector is pMSG. This vector uses the glucocorticoid-inducible promoter of the mouse mammary tumour virus long terminal repeat to drive expression of the cloned gene.

Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (Yips) and incorporate the yeast selectable markers HIS3, TRP1, LEU2 and URA3. Plasmids pRS413-416 are Yeast Centromere plasmids (Ycps).

Other vectors and expression systems are well known in the art for use with a variety of host cells.

The host cell can be either prokaryotic or eukaryotic. Bacterial cells are preferred prokaryotic host cells and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No. ATCC 31343). Preferred eukaryotic host cells include yeast, insect and mammalian cells, preferably vertebrate cells such as those from a mouse, rat, monkey or human fibroblastic and kidney cell lines. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CRL 1658, 293 cells which are human embryonic kidney cells, and NS0 cells. Preferred insect cells are Sf9 cells which can be transfected with baculovirus expression vectors.

Transformation of appropriate cell hosts with a DNA construct of the present invention is accomplished by well known methods that typically depend on the type of vector used. With regard to transformation of prokaryotic host cells, see, for example, Cohen et al (1972) *Proc. Natl. Acad. Sci. USA* 69, 2110 and Sambrook et at (1989) *Molecular Cloning*, A Laboratory Manual, Cold Spring Harbor Laboratory, Cold Spring Harbor, N.Y. Transformation of yeast cells is described in Sherman et al (1986) *Methods In Yeast Genetics, A Laboratory Manual*, Cold Spring Harbor, N.Y. The method of Beggs (1978) *Nature* 275, 104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming and/or transfecting cells and is well known in the art for transforming yeast cells, bacterial cells, insect cells and vertebrate cells.

For example, many bacterial species may be transformed by the methods described in Luchansky et al (1988) *Mol. Microbiol.* 2, 637-646 incorporated herein by reference. The greatest number of transformants is consistently recovered following electroporation of the DNA-cell mixture suspended in 2.5 PEB using 6250V per cm at 25 µFD.

Methods for transformation of yeast by electroporation are disclosed in Becker & Guarente (1990) *Methods Enzymol.* 194, 182.

Successfully transformed cells, i.e. cells that contain a DNA construct of the present invention, can be identified by well-known techniques. For example, cells resulting from the introduction of an expression construct of the present invention can be grown to produce the polypeptide of the invention. Cells can be harvested and lysed and their DNA content examined for the presence of the DNA using a method such as that described by Southern (1975) *J. Mol. Biol.* 98, 503 or Berent et al (1985) *Biotech.* 3, 208. Alternatively, the presence of the protein in the supernatant can be detected using antibodies as described below.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity.

Samples of cells suspected of being transformed are harvested and assayed for the protein using suitable antibodies.

The host cell may be a host cell within a non-human animal body. Thus, transgenic non-human animals which express a polypeptide according to the first aspect of the invention by virtue of the presence of the transgene are included. Preferably, the transgenic non-human animal is a rodent such as a mouse. Transgenic non-human animals can be made using methods well known in the art.

Methods of cultivating host cells and isolating recombinant proteins are well known in the art. It will be appreciated that, depending on the host cell, the polypeptides of the invention produced may differ. For example, certain host cells, such as yeast or bacterial cells, either do not have, or have different, post-translational modification systems which may result in the production of forms of polypeptides which may be post-translationally modified in a different way.

It is preferred that polypeptides of the invention are produced in a eukaryotic system, such as a mammalian cell.

According to a less preferred embodiment, the polypeptides of the invention can be produced in vitro using a commercially available in vitro translation system, such as rabbit reticulocyte lysate or wheatgerm lysate (available from Promega). Preferably, the translation system is rabbit reticulocyte lysate. Conveniently, the translation system may be coupled to a transcription system, such as the TNT® transcription-translation system (Promega). This system has the advantage of producing suitable mRNA transcript from an encoding DNA polynucleotide in the same reaction as the translation.

Thus, a second aspect of the invention provides an isolated nucleic acid molecule encoding a polypeptide according to the first aspect of the invention. In one embodiment, the nucleic acid molecule is a DNA molecule. Advantageously, the nucleic acid molecule further comprises a signal peptide recognisable by the host cell in which the polypeptide of the invention is expressed.

A third aspect of the invention provides a vector comprising a nucleic acid molecule according to the second aspect of the invention. In one embodiment, the vector is an expression vector (such as any vector from the pET-system, pRSET or pHIP).

A fourth aspect of the invention provides a host cell comprising a nucleic acid molecule according to the second aspect of the invention or a vector according to the third aspect of the invention.

In one embodiment, the host cell is an *E. coli* cell.

A fifth aspect of the invention provides a method for producing a polypeptide according to the first aspect of the invention comprising culturing a population of host cells comprising a nucleic acid molecule according to the second aspect of the invention or a vector according to the third aspect of the invention under conditions in which the polypeptide is expressed, and isolating the polypeptide therefrom. By "isolating" the expressed polypeptide we include removing some or all impurities from the culture medium, such as cell debris. In one embodiment, the polypeptide is substantially pure.

Alternatively, the polypeptides according to the first aspect of the invention may be produced by chemical synthesis (for example using Fmoc or t-Boc solid state synthesis methods).

It will be appreciated by persons skilled in the art that the polypeptides of the first aspect of the invention are preferably provided in the form of a pharmaceutical composition comprising the compound and a pharmaceutically acceptable carrier. Thus, a sixth aspect of the invention provides a pharmacological composition comprising a polypeptide according to the first aspect of the invention.

By "pharmaceutically acceptable" is included that the formulation is sterile and pyrogen free. Suitable pharmaceutical carriers are well known in the art of pharmacy. The carrier(s) must be "acceptable" in the sense of being compatible with the compound of the invention and not deleterious to the recipients thereof. Typically, the carriers will be water or saline which will be sterile and pyrogen free; however, other acceptable carriers may be used. Thus, "pharmaceutically acceptable carrier" and "pharmaceutically acceptable excipient" includes any compound(s) used in forming a part of the formulation that is intended to act merely as a carrier, i.e., not intended to have biological activity itself. The pharmaceutically acceptable carrier or excipient is generally safe, non-toxic, and neither biologically nor otherwise undesirable. A pharmaceutically acceptable carrier or excipient as used herein includes both one and more than one such carrier or excipient.

The polypeptides of the invention can be formulated at various concentrations, depending on the efficacy/toxicity of the compound being used. Preferably, the formulation comprises the agent of the invention at a concentration of between 0.1 µM and 1 mM, more preferably between 1 µM and 100 µM, between 5 µM and 50 µM, between 10 µM and 50 µM, between 20 µM and 40 µM and most preferably about 30 µM. For in vitro applications, formulations may comprise a lower concentration of a compound of the invention, for example between 0.0025 µM and 1 µM.

It will be appreciated by persons skilled in the art that the polypeptides of the invention will generally be administered in admixture with a suitable pharmaceutical excipient diluent or carrier selected with regard to the intended route of administration and standard pharmaceutical practice (for example, see *Remington: The Science and Practice of Pharmacy*, 19$^{th}$ edition, 1995, Ed. Alfonso Gennaro, Mack Publishing Company, Pennsylvania, USA, which is incorporated herein by reference).

For example, the polypeptides of the invention can be administered orally, buccally or sublingually in the form of tablets, capsules, ovules, elixirs, solutions or suspensions, which may contain flavouring or colouring agents, for immediate-, delayed- or controlled-release applications. The medicaments and agents may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The polypeptides of the invention can also be administered parenterally, for example, intravenously, intra-articularly, intra-arterially, intraperitoneally, intra-thecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of the medicaments and agents will usually be from 1 to 1000 mg per adult (i.e. from about 0.015 to 15 mg/kg), administered in single or divided doses.

The polypeptides of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoro-methane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or 'puff' contains at least 1 mg of a compound of the invention for delivery to the patient. It will be appreciated that the overall daily dose with an aerosol will vary from patient to patient, and may be administered in a single dose or, more usually, in divided doses throughout the day.

Alternatively, the polypeptides of the invention can be administered in the form of a suppository or pessary, or they may be applied topically in the form of a lotion, solution, cream, ointment or dusting powder. The compounds of the invention may also be transdermally administered, for example, by the use of a skin patch. They may also be administered by the ocular route.

For application topically to the skin, the polypeptides of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

In the case of polypeptide-based medicaments, it may be preferable to use a sustained-release drug delivery system, such as a microsphere. These are designed specifically to reduce the frequency of injections. An example of such a system is Nutropin Depot which encapsulates recombinant human growth hormone (rhGH) in biodegradable microspheres that, once injected, release rhGH slowly over a sustained period.

Sustained-release immunoglobulin compositions also include liposomally entrapped immunoglobulin. Liposomes containing the immunoglobulin are prepared by methods known per se. See, for example Epstein et al., *Proc. Natl. Acad. Sci. USA* 82: 3688-92 (1985); Hwang et al., *Proc. Natl. Acad. Sci. USA* 77: 4030-4 (1980); U.S. Pat. Nos. 4,485,045; 4,544,545; 6,139,869; and 6,027,726. Ordinarily, the liposomes are of the small (about 200 to about 800 Angstroms), unilamellar type in which the lipid content is greater than about 30 mole percent (mol. %) cholesterol; the selected proportion being adjusted for the optimal immunoglobulin therapy.

Alternatively, the polypeptides of the invention can be administered by a surgically implanted device that releases the drug directly to the required site.

Electroporation therapy (EPT) systems can also be employed for the administration of proteins and polypeptides. A device which delivers a pulsed electric field to cells increases the permeability of the cell membranes to the drug, resulting in a significant enhancement of intracellular drug delivery.

Proteins and polypeptides can also be delivered by electroincorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with drugs or genes or can simply act as "bullets" that generate pores in the skin through which the drugs can enter.

An alternative method of protein and polypeptide delivery is the thermo-sensitive ReGel injectable. Below body temperature, ReGel is an injectable liquid while at body temperature it immediately forms a gel reservoir that slowly erodes and dissolves into known, safe, biodegradable polymers. The active drug is delivered over time as the biopolymers dissolve.

Protein and polypeptide pharmaceuticals can also be delivered orally. One such system employs a natural process for oral uptake of vitamin B12 in the body to co-deliver proteins and polypeptides. By riding the vitamin B12 uptake system, the protein or polypeptide can move through the intestinal wall. Complexes are produced between vitamin B12 analogues and the drug that retain both significant affinity for intrinsic factor (IF) in the vitamin B12 portion of the complex and significant bioactivity of the drug portion of the complex.

In a further aspect of the invention, there are provided medical implant materials comprising a polypeptide of the invention, as well as medical devices made of such materials.

By 'medical implant material' we include a material for implantation into the human or animal body, such as a material for use as an artificial tissue (e.g. bone, teeth and skin), prosthetic devices (e.g. joints, heart valves, blood vessels) and drug delivery devices.

It will be appreciated by those skilled in the art that the medical implant materials of the invention may comprise naturally-occurring polymers, synthetic polymers, co-polymers of such polymers, and blends thereof (which are coated, impregnated or otherwise admixed with a polypeptide of the invention).

In one embodiment, the polymer is a naturally-occurring polymer. More preferably, the polymer is a naturally-occurring extracellular matrix molecule such as collagen, fibronectin, fibrin, fibrillin, glycosoaminoglycans, and hyaluronic acid.

Alternatively, the polymer may be a synthetic polymer. For example, the polymer is a synthetic polymer selected from the group consisting of poly(ε-caprolactone) (PCL), poly(L-lactide) (PLA), poly(glycolide) (PGA), poly(DL-lactide co-glycolide) (PLG) and co-polymers and blends thereof. Other synthetic polymers include methacrylates poly(ethylmethacrylate), ethylacrylate, tetrahydrofurfuryl-methacrylate, hydroxyethyl-methacrylate, silastic, poly(tetrafluoroethylene), medpore (porous polyethylene), poly(orthoester), and poly(dioxane).

Most preferably, the medical implant material comprises poly-(ε-caprolactone).

It will be appreciated that the polymers may be biodegradable or non-biodegradable. Preferably, the polymer is biodegradable. More preferably, the polymer is a biodegradable polymer which has a biodegradation rate that is the same as or slower than the rate of regeneration of the tissue for which the medical implant acts as a temporary replacement. Thus, the biodegradable polymer should be resorbed only after it has served its purpose as a scaffold for regeneration of new tissue. It will be further appreciated that the polymer and its degradation product(s) should be substantially non-toxic and non-inflammatory.

Methods of making such polypeptide-polymer medical implant materials and devices thereof are well known in the art (for example, see WO 01/85224, the disclosures of which are incorporated by reference).

A key aspect of the invention provides a polypeptide according to the first aspect of the invention for use in medicine.

Thus, polypeptides capable of inhibiting the binding of a heparan sulfate proteoglycan to a tissue transglutaminase may be used in medicine to modulate (either by enhancing, e.g. mimicking, or by inhibiting) one or more functions of an endogenous tissue transglutaminase.

In one embodiment, the invention provides polypeptides capable of inhibiting the translocation of a tissue transglutaminase into the extracellular matrix. As shown schematically in FIG. 10, inhibition of the binding of heparan sulfate proteoglycans to tissue transglutaminase disrupts translocation of the transglutaminase across the cell membrane, preventing its localisation on the cell surface and (subsequently) within the extracellular matrix Consequently, the polypeptides of the invention may be used for treating and/or preventing a disease, disorder or condition which would benefit from treatment with an inhibitor of an extracellular tissue transglutaminase.

For example, the polypeptides may be for use in inhibiting angiogenesis (in a subject).

Alternatively, the polypeptides may be for treating and/or preventing a disease, disorder or condition selected from the group consisting of fibrosis (including cystic fibrosis), scarring, neurodegenerative diseases, autoimmune diseases, thrombosis, proliferative disorders (such as cancer), AIDS, psoriasis, inflammation (including chronic inflammatory diseases, such as coeliac disease) and organ transplant rejection.

In a further embodiment, the invention provides polypeptides (derived from the heparin-binding site of capable of tissue transglutaminase) that are capable of mimicking the effect of tissue transglutaminase on cell behaviour (see above).

Consequently, the polypeptides of the invention may be used for treating and/or preventing a disease, disorder or condition which would benefit from treatment with a tissue transglutaminase.

For example, the polypeptides may be for use in wound healing, such as in the treatment of pressure sores, burns or bone disorders and fractures.

A related aspect of the invention provides the use of a polypeptide of the first aspect of the invention in the preparation of a medicament for modulating (either by enhancing, e.g. mimicking, or by inhibiting) one or more functions of an endogenous tissue transglutaminase.

In one embodiment, the medicament is for inhibiting the translocation of a tissue transglutaminase into the extracellular matrix.

In one embodiment, the medicament is for treating and/or preventing a disease, disorder or condition which would benefit from treatment with an inhibitor of an extracellular tissue transglutaminase.

For example, the medicament may be for inhibiting angiogenesis (in a subject).

The medicament may also be for treating and/or preventing a disease, disorder or condition selected from the group consisting of fibrosis (including cystic fibrosis), scarring, neurodegenerative diseases, autoimmune diseases, thrombosis, proliferative disorders (such as cancer), AIDS, psoriasis, inflammation (including chronic inflammatory diseases, such as coeliac disease) and organ transplant rejection.

In a further embodiment, the medicament is capable of mimicking the effect of tissue transglutaminase on cell behaviour (see above).

Consequently, the medicament may be for treating and/or preventing a disease, disorder or condition which would benefit from treatment with a tissue transglutaminase.

For example, the medicament may be for use in wound healing, such as in the treatment of pressure sores, burns or bone disorders and fractures.

A further related aspect of the invention provides a method for treating and/or preventing in a subject a disease, disorder or condition which would benefit from treatment with a modulator of a tissue transglutaminase, the method comprising administering to the subject a polypeptide of the first aspect of the invention.

The terms "treating", and "treatment", and the like are used herein to generally mean obtaining a desired pharmacological and physiological effect. Further, it refers to any process, action, application, therapy, or the like, wherein a mammal, including a human being, is subject to medical aid with the object of improving the mammal's condition, directly or indirectly. Thus, treatment includes both therapeutic and prophylactic use.

The polypeptide or pharmaceutical composition of the invention is administered to the patient in an effective amount. A 'therapeutically effective amount', or 'effective amount', or 'therapeutically effective', as used herein, refers to that amount which provides inhibition of the binding of a heparan sulfate proteoglycan to a tissue transglutaminase. This is a predetermined quantity of the polypeptide calculated to produce the desired therapeutic effect. Further, it is intended to mean an amount sufficient to reduce and most preferably to prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art.

In one embodiment, the method is for inhibiting the translocation of a tissue transglutaminase into the extracellular matrix.

In one embodiment, the method is for treating and/or preventing a disease, disorder or condition which would benefit from treatment with an inhibitor of an extracellular tissue transglutaminase.

For example, the method may be for inhibiting angiogenesis (in a subject).

The method may also be for treating and/or preventing a disease, disorder or condition selected from the group consisting of fibrosis (including cystic fibrosis), scarring, neurodegenerative diseases, autoimmune diseases, thrombosis, proliferative disorders (such as cancer), AIDS, psoriasis, inflammation (including chronic inflammatory diseases, such as coeliac disease) and organ transplant rejection.

In a further embodiment, the method is for treating and/or preventing a disease, disorder or condition which would benefit from treatment with a tissue transglutaminase.

For example, the method may be for wound healing, such as the treatment of pressure sores, burns or bone disorders and fractures It will be appreciated by those skilled in the art that the polypeptides of the invention may be administered by any route known or developed in the art. Thus, the polypeptide or formulation thereof may be administered by parenteral injection (e.g. intravenous, subcutaneous or intramuscular), by topical application, by inhalation or nasal administration, or orally.

In one embodiment, the polypeptide is administered systemically, for example intravenously. Alternatively, the polypeptide or formulation may be administered topically, e.g. at or near a target site where angiogenesis is to be inhibited.

Treatment with a polypeptide of the invention may consist of a single dose or a plurality of doses over a period of time. Advantageously, the polypeptide may be administered repeatedly.

Polypeptides of the invention may also be administered by a surgically implanted device that releases the compound directly to the required site, for example at or near a site of tissue transglutaminase-mediated protein modification.

It will be appreciated by persons skilled in the art that a subject treated using the polypeptides of the invention may be any mammal. Preferably, the subject is human. Alternatively, the subject may be a dog, cat, horse, or other domestic or farm mammalian animal.

Exemplary embodiments of the invention are described in the following non-limiting examples, with reference to the following figures:

FIG. 1. 3D Structure of TG2 and Predicted Heparin Binding Site (A) Ribbon representation of the crystal structure of TG2 (derived from 1KV3.pdb) showing the four domains with putative HSPG binding sites denoted. (B) Detailed view of the HS1 site, showing the juxtaposition of basic residues potentially involved in HSPG binding. (C) Detailed view of the HS2 site, showing the juxtaposition of basic residues potentially involved in HSPG binding. (D) Predicted binding site of a heparin-derived pentasaccharide into the HS2 site of TG2.

FIG. 2. Expression and Activity of TG2 and Site-Directed TG2 Mutants in HEK 293/117 and NIH 3T3 Cells. (A) Illustration of expression level of wt TG2 and TG2 mutants in HEK 293/T17 cells and (D) NIH 3T3 cells after 48 hours post-transfection detected with anti-TG2 antibody by Western blot analysis. (B, E) Measurement of TG2 and mutant activity in HEK 293/T17 cells and NIH 313 cells, respectively, by biotin-X-cadaverine incorporation into N,N'-dimethylcasein as described in the Materials and Methods. Normalisation of TG2 and mutant expression using tubulin for equal loading and normalisation. TG2 and mutant activity in cell lysates of HEK 293/T17 cells (C) and NIH 3T3 cells (F) using normalised TG2 and mutant expression values.

Figure 3:
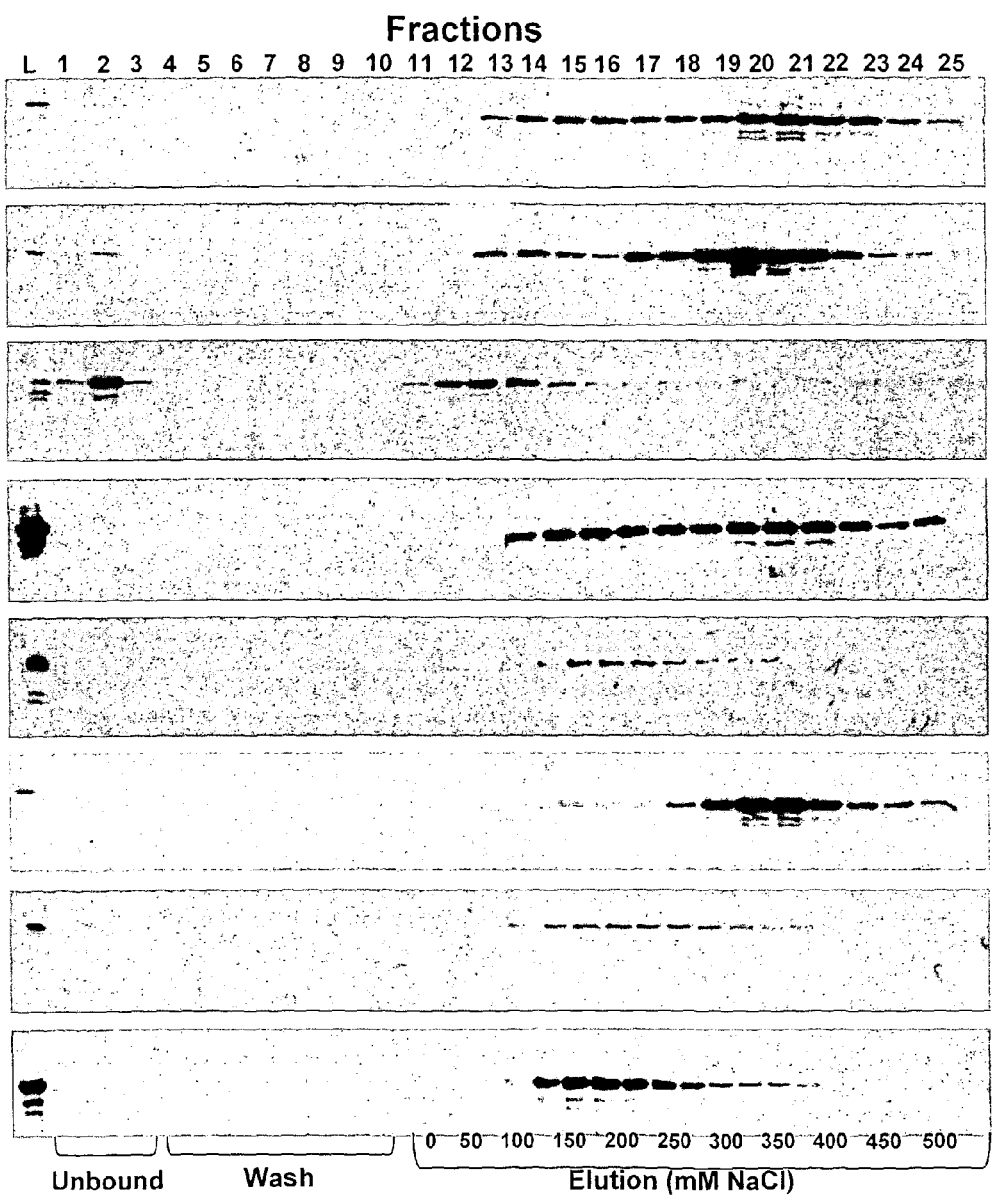

FIG. 3. Differences in the binding strength of TG2 and TG2 mutants on a heparin SEPHAROSE® affinity column. Clarified cell lysates from HEK293/T17 cells transfected with wtTG2, and TG2 mutants, were applied to a 5 ml bed volume heparin SEPHAROSE® column, equilibrated in 50 mM Tris-Cl, 1 mM EDTA, 1 mM DTT pH 7.5 buffer and eluted as described in the Materials and Methods with a linear (0-1M) NaCl gradient with the elution concentration pattern for NaCl shown. Both flow-through and resulting fractions (1-25 as shown) were assayed for TG2 activity and verified for presence of TG2 by Western blotting using anti-TG2 monoclonal antibody (CUB 7402) as described in the Materials and Methods.

FIG. 4. The Effect of P1 Peptide (SEQ ID NO:2) on the RGD-Induced Loss of Cell Adhesion on FN or TG-FN. (A) The dose-dependent compensatory effect of P1 peptide on the RGD-induced loss of cell adhesion. HOB cells were treated with P1 peptide from the concentrations of 0.01 to 200 μg/ml in the presence of RAD or RGD peptides as described in the Materials and Methods. RAD-treated HOB cells seeded on FN matrix were used as the control group (the 0 groups). (B) HOB cells plated on FN incubated with RAD or RGD peptide in the presence of P1 peptide at the concentrations shown, (C) The effect of P1 peptide on the RGD-induced loss of cell attachment and spreading. P1 peptide, at the concentrations of 100-300 μg/ml, was applied in the cell adhesion assay using TG-FN matrix in the presence of RAD or RGD peptide, while the RAD-treated HOB cells on FN matrix was used as the control group (CNTL) as described in Materials and Methods and the scrambled peptide (P1s) was used as the control treatment for the P1 peptide. (D and E) Involvement of the cell surface heparan sulfate chains of Syndecan 4 in the P1 peptide-regulated cell adhesion. (D) The importance of heparan sulfate chains. 15 mU/ml of Heparanase was used to digest the HS on the HOB cell surface, while chondroitinase at the concentration of 15 mU/ml was used as the control treatment. After one-hour incubation, the cell adhesion assay on FN was performed as described in Materials and Methods. The non-treated HOB cells were used as the control group (CNTL), while the scrambled P1 peptide (P1s) is the control treatment for the P1 peptide. (E) The requirement of syndecan-4 by P1 peptide to compensate the effect of RGD induced loss of cell adhesion. Syndecan-4 targetting siRNA was used to silence the expression of the receptors as described in the Materials and Methods. The data shown in each experiment are mean values+/−SD from 3 separate experiments.

Figure 5:
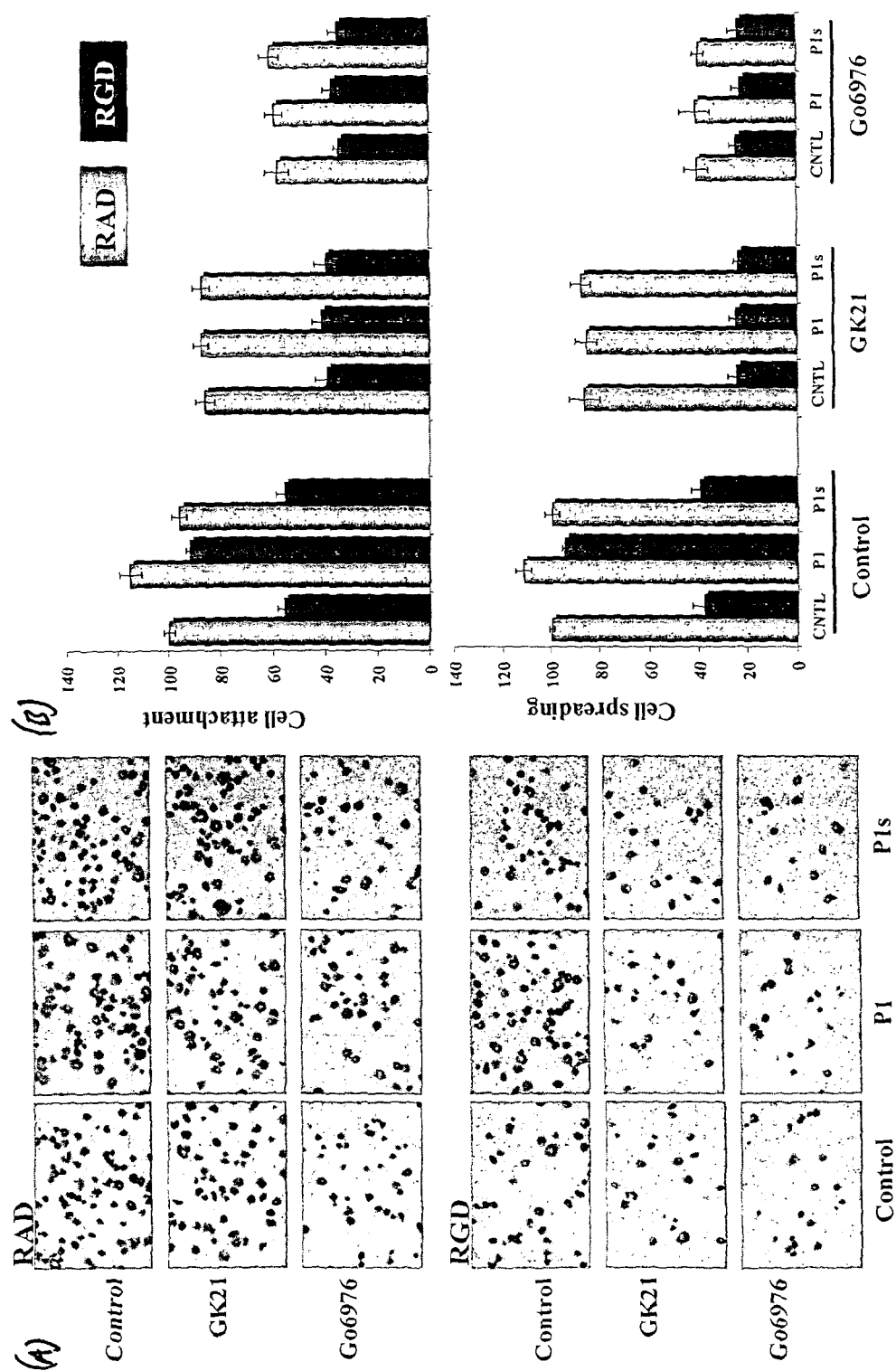

FIG. 5. The Importance of PKCα in P1 Peptide-Mediated Cell Adhesion. (A) and (B), the cell adhesion assay on FN in the presence of RGD or RAD was performed in the presence of PKCα inhibitor Go6976 (5 μM) or the GK21 peptide (8 μM) (which blocks the interaction between PKCα and the intracellular domain of (31 integrins) as described in Materials and Methods. Incubations were undertaken in the presence of 100 ug/ml P1 or P1s peptide. The data shown are mean values+/−SD from 3 separate experiments.

Figure 6:
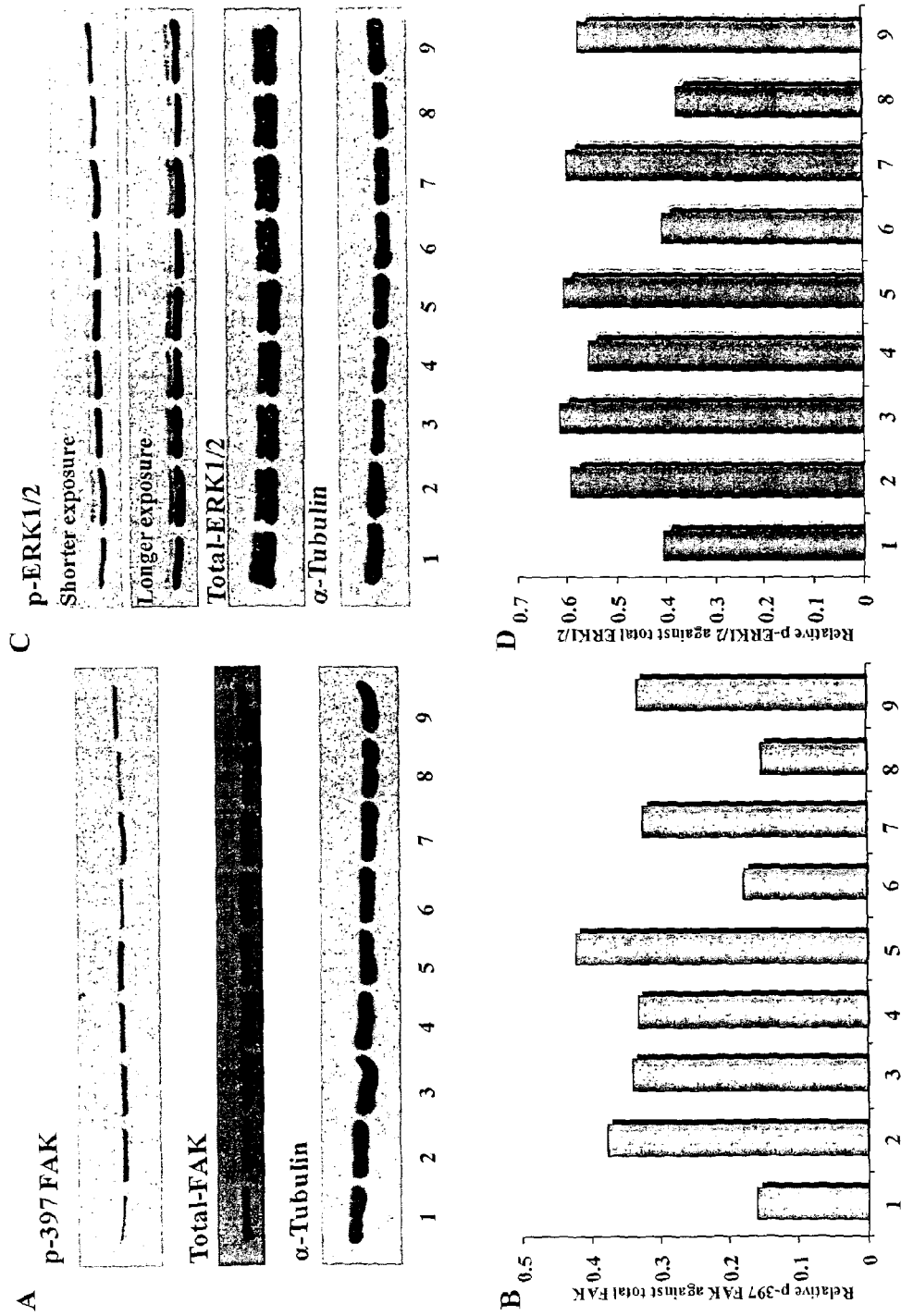

FIG. 6. Identification of the intracellular signalling molecules in P1 peptide-mediated signalling transduction. (A) The importance of FAK in P1 mediated cell adhesion on FN in the presence of RGD or RAD peptide (150 μg/ml) was performed in the presence of 100 μg/ml P1 or P1s peptide. Cell lysates were used to detect by Western blotting the presence of p-397 FAK by using mouse anti-human p-397 FAK antibody and HRP-conjugated anti-mouse secondary as described in Materials and Methods. The membranes were reprobed to detect the total FAK, while α-tubulin was used as the standard for equal loading. The RAD-treated HOB cells seeded on BSA-coated plates was used as the negative control group, while the TG-FN matrix was used as the positive control. Lane 1, the RAD-treated HOB cells on BSA; Lane 2, the RAD-treated HOB seeded on FN; Lane 3, RAD-treated HOB seeded on TG-FN; Lane 4, the P1 s-treated cells on FN in the presence of the RAD peptide; Lane 5, the P1 and RAD-treated HOB cells on FN; Lane 6, the RGD-treated HOB on FN; Lane 7, the RGD-treated HOB on TG-FN; Lane 8, the RGD and P1s peptides-treated HOB on FN; Lane 7, the RGD and P1 peptides-treated HOB on FN matrix. The histogram (B) shows the relative amounts (mean from two experiments) of p-397 FAK compared to total FAK measured by densitometry after normalisation to tubulin for equal loading. (C) The requirement of the phosphorylation of ERK1/2 for P1 peptide to function. Cell lysate samples from a comparable assay introduced above in (A) were used in Western blotting to detect the presence of p-ERK1/2 by using specific anti-p-ERK1/2 antibody, while total ERK1/2 and α-tubulin were also detected by using the specific antibodies to the reprobed membranes. The RAD-treated HOB cells seeded on BSA and TG-FN-coated plates were used as the negative and positive control matrices, respectively. The orders of the lanes follow the ones in FIG. 6A. The histogram (D) shows the relative amounts (mean from two experiments) of p-ERK1/2 compared to total ERK1/2 measured by densitometry after normalisation to tubulin for equal loading.

Figure 7:
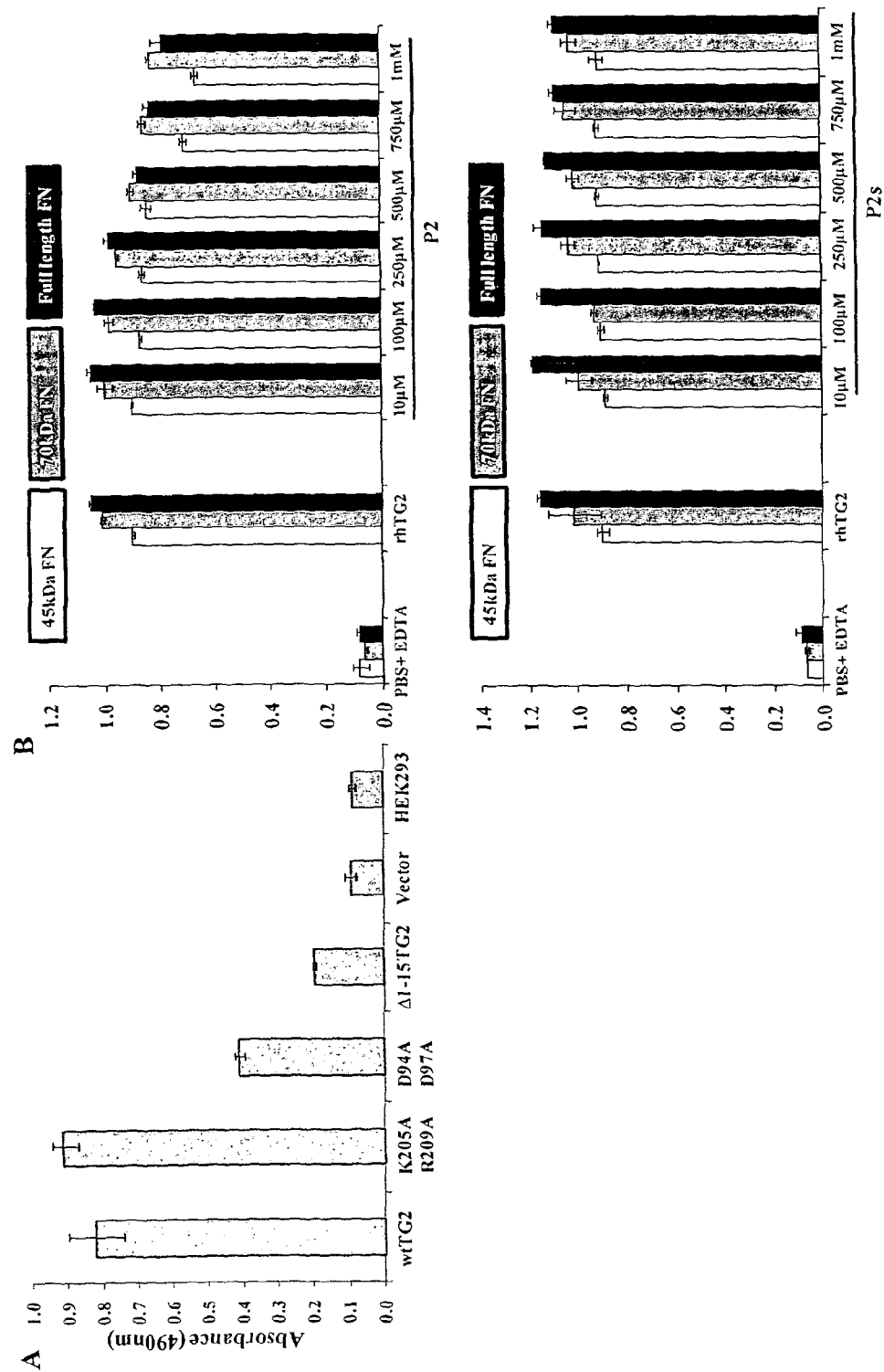

FIG. 7. Affinity of TG2 and the Binding Site Mutant (D94A,D97A), the N-Terminal Deletion Product of TG2 (Δ1-15) and the HS2 Mutant (K205A, R209A) for Binding to FN. (A) Clarified cell lysates (60 μg protein) from transiently transfected cells were added to FN-coated plates, incubated for 1 h at 37 C, washed and the TG2 proteins then detected as described in the Materials and Methods. The data shown have been normalised for the expression of TG2 and its mutants in the different cell lysates using densitometry values from Western blots. Equal protein loadings were normalised to tubulin. The values represent the mean values+/−SD from 3 separate experiments. (B) Human recombinant TG2 (2 μg/ml) was added to microtitre plates previously coated with FN, 70 kDa or the 45 kDa FN fragments. Prior to addition of the TG2, wells were blocked, washed and then incubated with either the P2 peptide or the scrambled P2 peptide (P2S) as described in the Materials and Methods. After incubation of the TG2 for 2 h in the presence of the P1 or P1s peptides at the concentrations shown, plates were washed and TG2 detected as described in the Materials and Methods. Data show the mean values+/−SD from 3 separate experiments.

Figure 8:
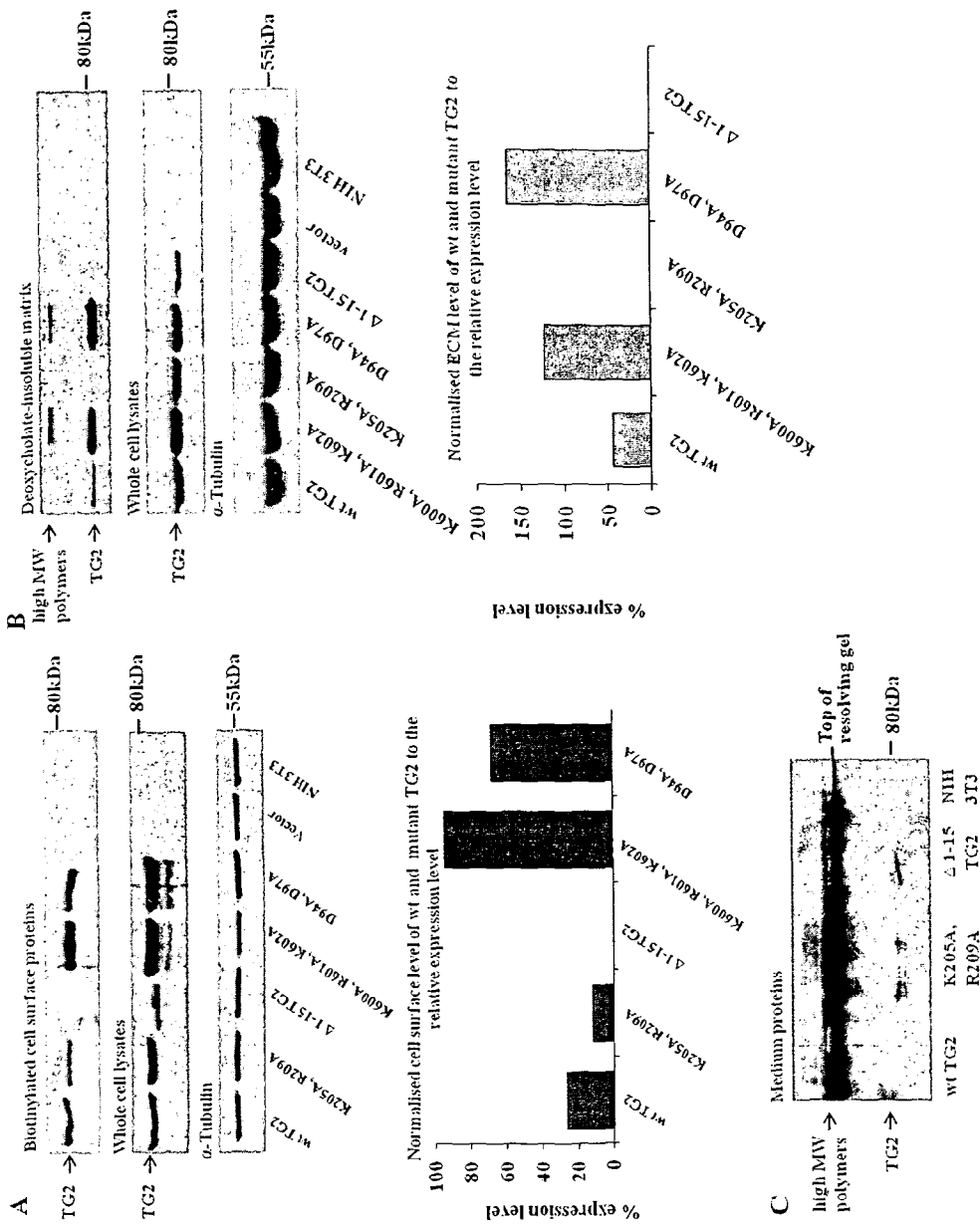

FIG. 8. Detection of extracellular TG2 in NIH 3T3 cells transfected with wild type TG2 and TG2 mutants. (A) For cell surface TG2, cells transiently transfected with the wild type enzyme and TG2 constructs were treated with sulfo-NHS-LC-biotin, lysed and incubated with NEUTRAVIDIN® avidin protein-Agarose resin as described in the Methods and Materials. The TG2 antigen bound to the resin was then detected by Western blotting using anti-TG2 antibody CUB 7402. The histogram shown in (A) gives the densitometry values (mean values from 2 experiments) for the different TGs after correcting for loading using tubulin and then normalising to the expression levels of the different TGs calculated from parallel Western blotting experiments of the different cell lysates as previously described in Figure legend 2. For the presence of TG2 and TG2 mutants in the extracellular matrix (B) and cell culture medium (C), NIH 3T3 cells transfected with wild type TG2 and TG2 mutants were grown for 24 h post transfection in DMEM supplemented with 10% (v/v) serum and then for a further 48 h in medium containing 1% (v/v) serum. The presence of TG2 antigen in the ECM and in the culture medium was then detected by Western blotting using anti-TG2 antibody CUB 7402 as described in the Materials and Methods. The histogram in (B) represents the densitometric values for matrix TG2 and its mutants after normalising for the relative expression of TG2 in the cell lysates measured by Western blotting. Tubulin was used to normalise for equal loadings to the gel for TG2 present in the cell lysates.

Figure 9:
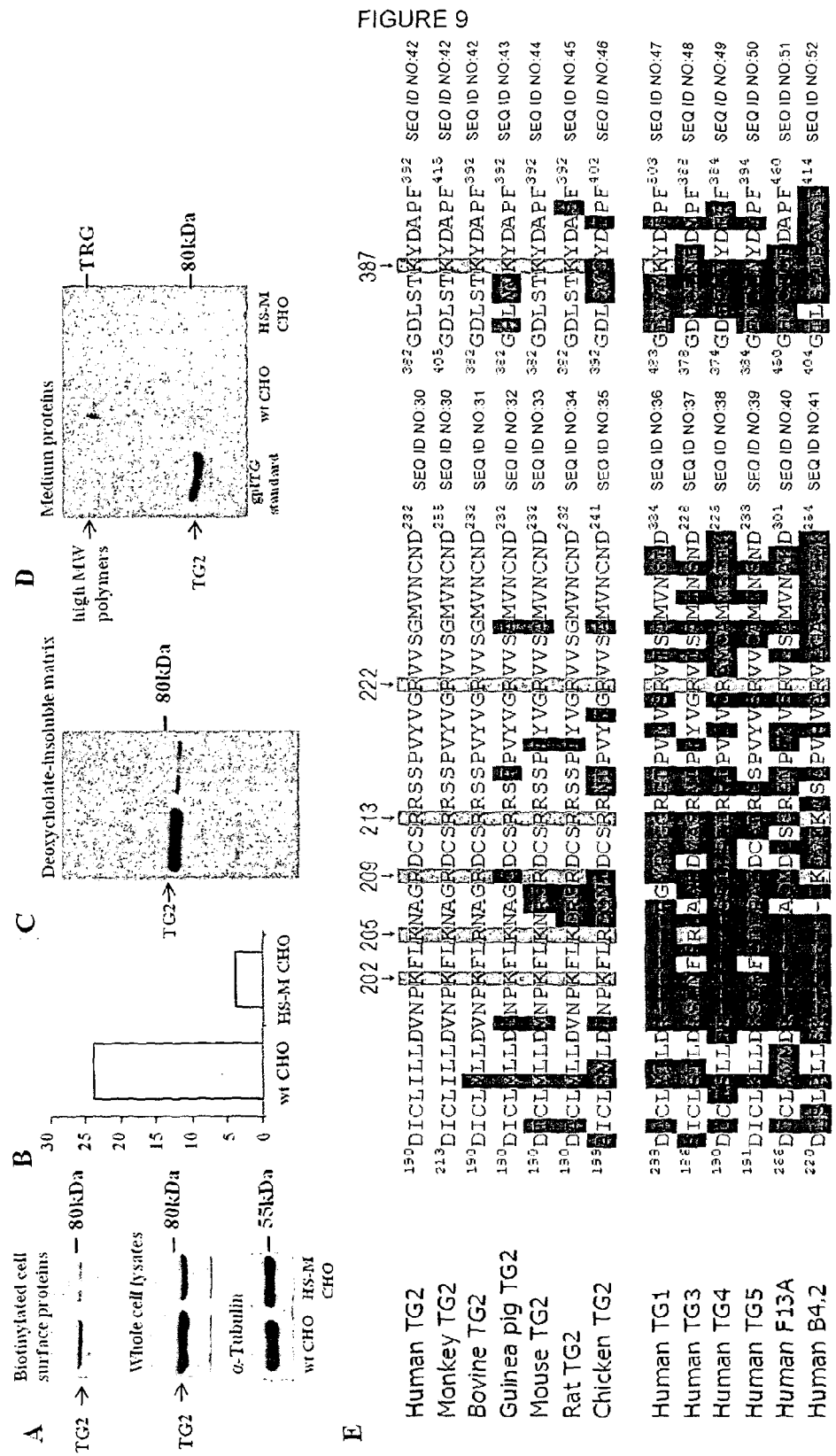

FIG. 9. Presence of extracellular TG2 in CHO K1 cells and the HS deficient CHO-K1 derivative pgsD-677 (A-D) and (E) a multiple alignment of TG peptide sequences, including TG2 from different species and human TG isoforms. (A) shows the Western blots for cell surface TG2 which was obtained by biotinylation of cell surfaces and then the cell lysates purified using NEUTRAVIDIN® avidin protein-Agarose resin as described in the legend to FIG. 8. The histogram (B) shows the relative amounts of TG2 measured by densitometry on the cell surface (mean values from 2 experiments) after normalising for the expression levels of TG2 in cell lysates as determined by Western blotting. Tubulin was used to normalise for equal loadings for the TG2 present in the cell lysates. For the presence of TG2 in the extracellular matrix (C) and cell culture medium (D), CHO-K1 and HS-mutant CHO cells were cultured in mixture F-12 (Ham) medium (Sigma-Aldrich, UK) supplemented with 10% (v/v) FBS for 24 h and then for a further 48 h in medium containing 1% (v/v) serum. The presence of TG2 antigen in the ECM (C) and in the culture medium (D) was then detected by Western blotting using anti-TG2 antibody CUB 7402 as described in the Materials and Methods. (E) shows the multiple alignment of TG peptide sequences, including TG2 from different species and human TG isoforms. The residues corresponding to human TG2 positions 202, 205, 213 and 222 are conserved as basic residues amongst all the TG2 sequences analysed showing the heparin binding domain is conserved amongst TG2 enzymes, but is absent from other isoforms.

Figure 10:
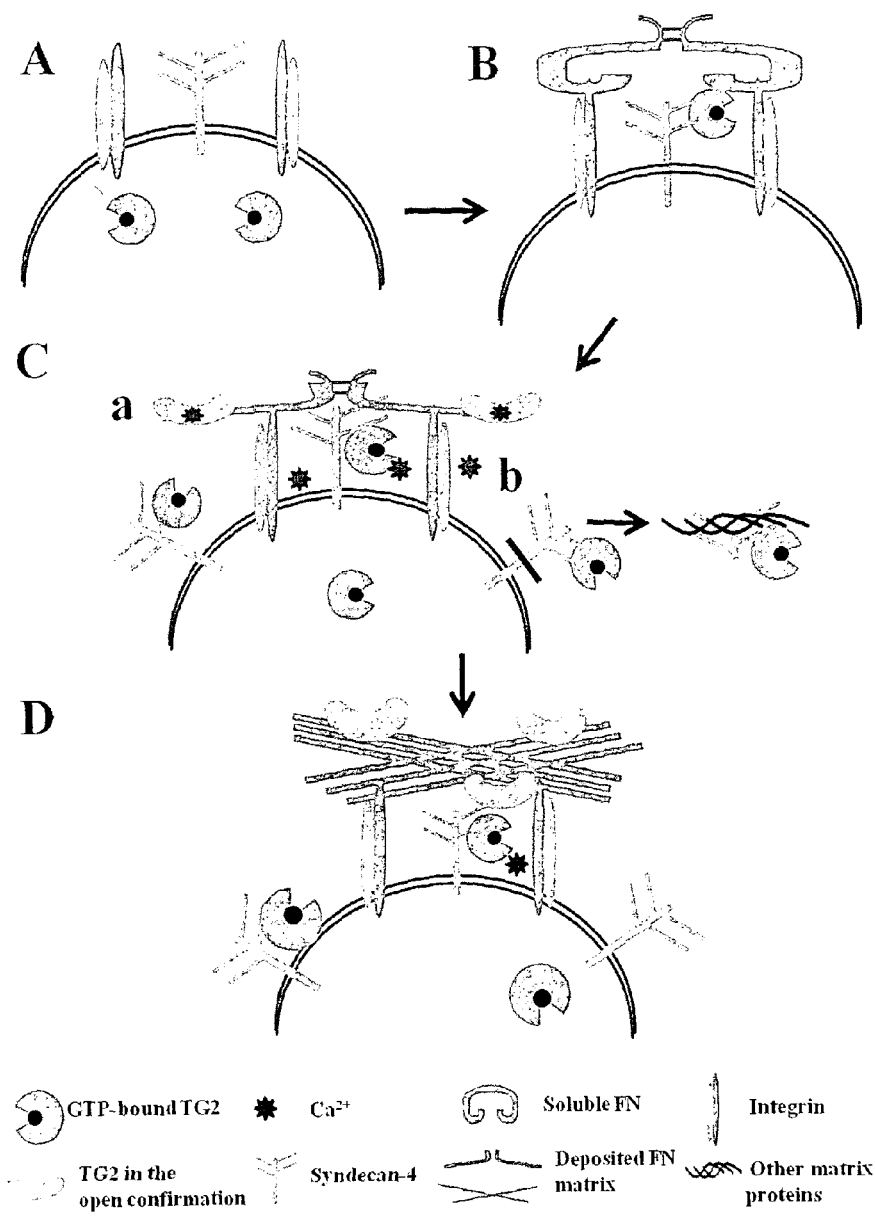

FIG. 10. Shows a Schematic Representation of a Potential Mechanism for Translocation of TG2 into the Extracellular Matrix. (A-B) TG2 appears on the cell surface in its GTP-bound compact conformation and immediately binds to cell surface HSPGs with high affinity. Following binding to extracellular $Ca^{2+}$, GTP/GDP is released from TG2 and the enzyme adopts an extended conformation facilitating its release from the HSPGs and the binding to FN (C) during fibril assembly (a). TG2 may also bind to other ECM proteins or to Beta integrins present at the cell surface at this stage. To facilitate increased TG2 present in the matrix e.g. during wound healing, TG2 may also be shed into the matrix by the shedding of cell surface HS (b). Once released from the cell surface HS the process starts again (D)

Figure 11:
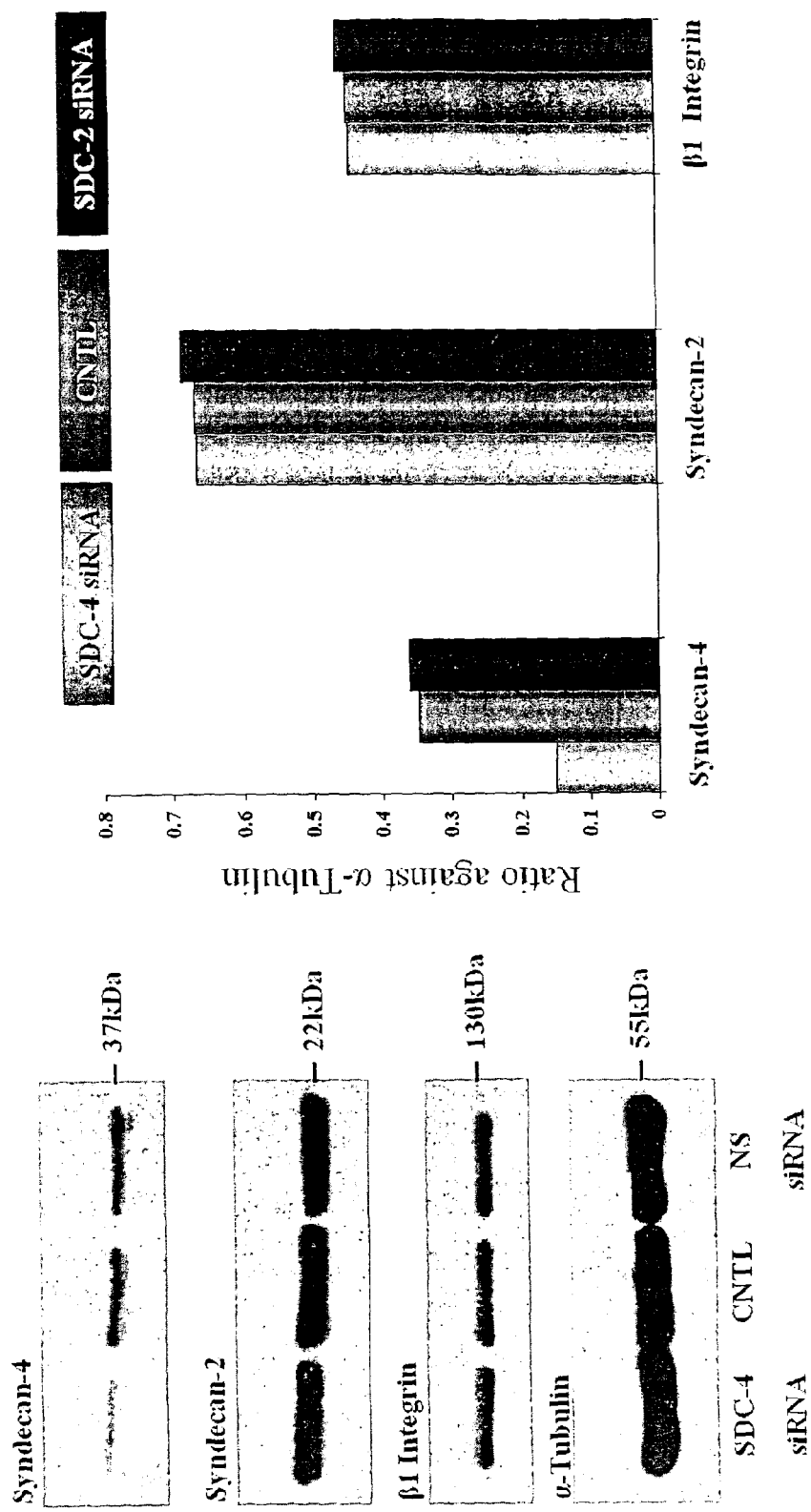

FIG. 11. The presence of syndecan-4, β1 integrin and syndecan-2 in the syndecan-4 siRNA treated HOB cells. The HOB cells seeded into 6-well plates were transfected with syndecan-4 targeting siRNA or non-silencing siRNA via HIPERFECT® transfection method as introduced in Material and Methods. The cell lysates were collected after 30-h incubation and Western blotting was performed to detect the presence of syndecan-4, β1 integrin and syndecan-2 by using specific antibodies as listed in the Materials and Methods.

Figure 12:
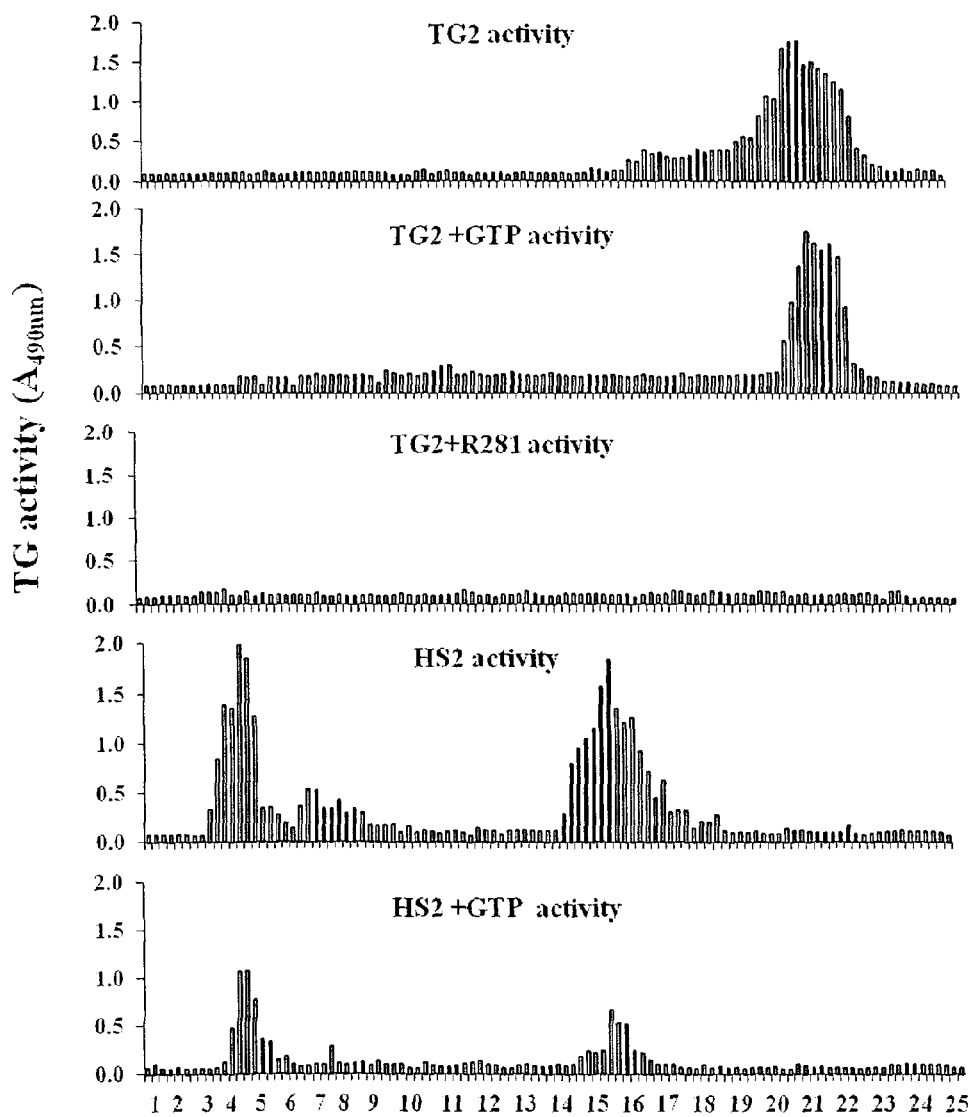

FIG. 12. Measurement of TG2 activity in fractions eluted from the heparin SEPHAROSE® column. Collected fractions were assayed for TG2 activity using the Biotin-X-cadaverine incorporation into N,N-dimethylcasein assay as described in the Materials and Methods.

Figure 13:
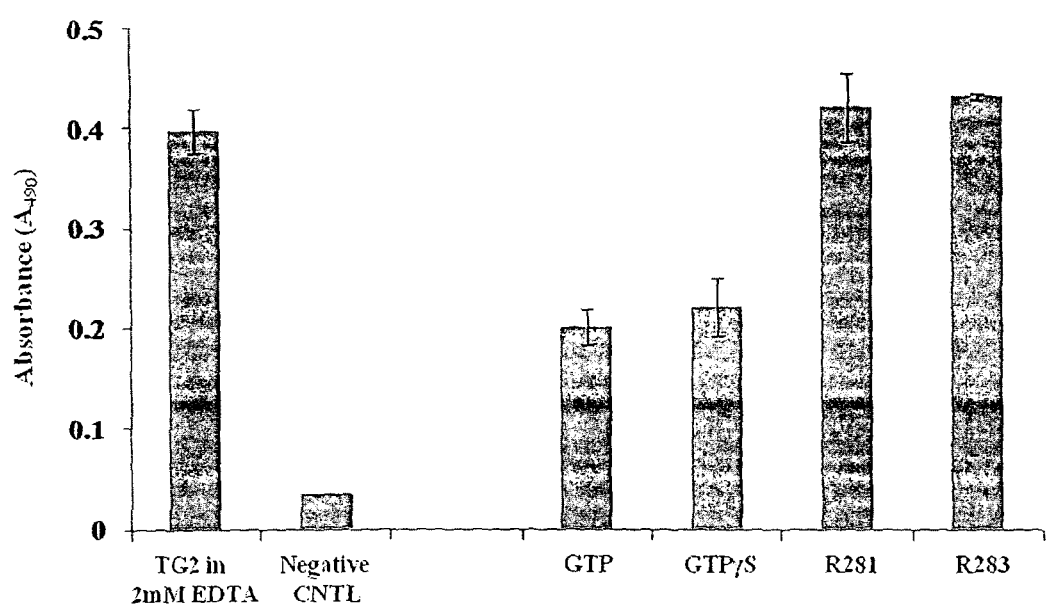

FIG. 13. Binding of Extended and Compact Forms of TG2 to Fibronectin. GPLTG (2 mg/ml) was reduced by pre-incubation with 1 mM DTT and then diluted in PBS, pH 7.4. The reduced gplTG 20 µg/ml was pre-incubated with 1 mM GTP or GTPyS(closed conformation) or TG2 site directed irreversible inhibitors R281 or R283(extended conformation) at the concentration of 500 µM (in the presence of 10 mM $Ca^{2+}$) at room temperature for 30 min. The treated enzymes were then incubated with the FN-coated wells (precoated at 5 µg/ml, at 4° C. overnight) at 37° C. for 1 h as described in the Materials and Methods. 20 µg/ml gplTG in 2 mM EDTA in PBS, pH 7.4 was used as the positive control and 2 mM EDTA in PBS, pH 7.4 was used as the negative control. The presence of TG2 bound to FN was detected via ELISA using anti-TG2 monoclonal antibody Cub 7402 as described in the Materials and Methods. Values represent the mean±S.D absorbance at 450 nm from 3 separate experiments.

Figure 14:
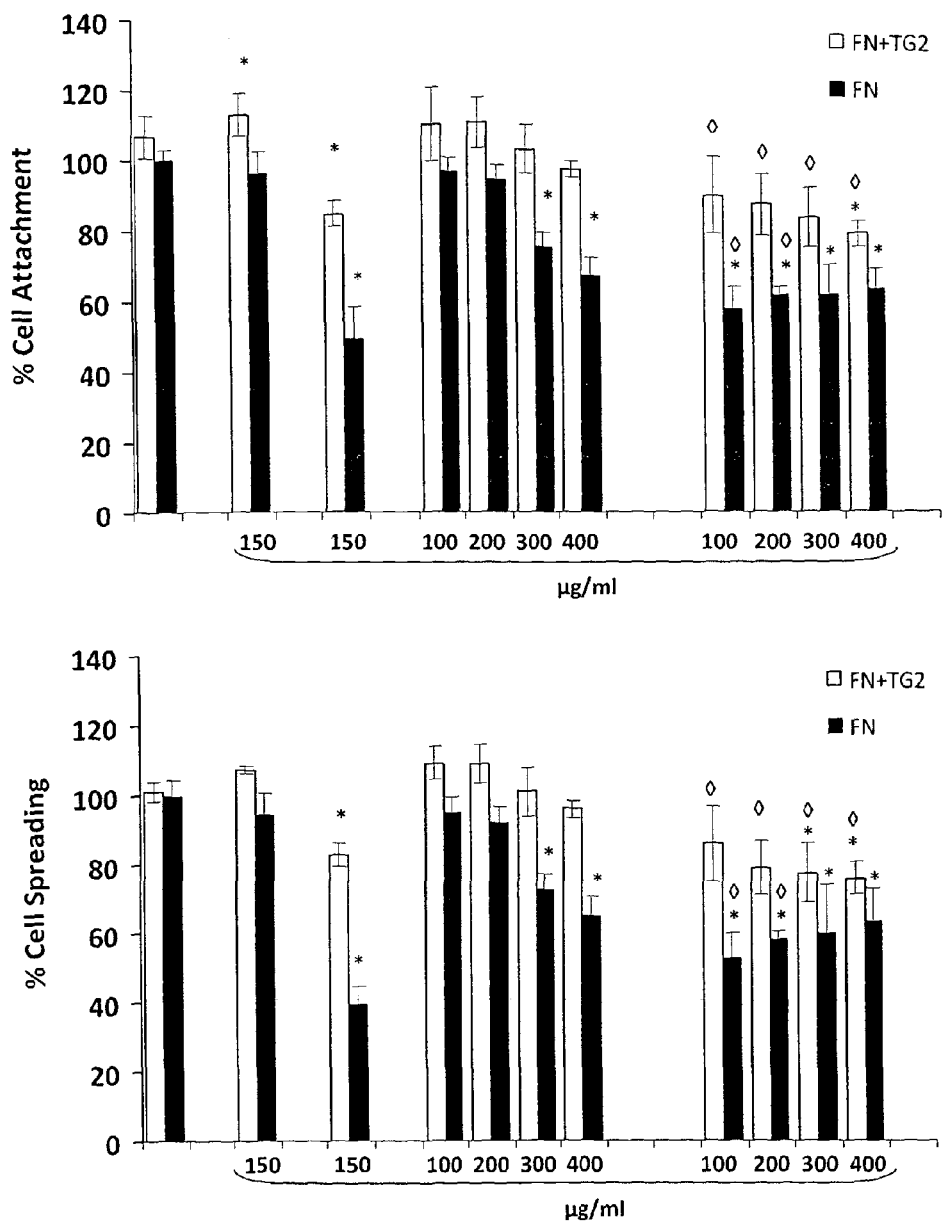

FIG. 14. Effect of Exemplary Peptide (NPKFLKNA; SEQ ID NO:4) in the Absence or Presence of RGD Peptide on the Attachment and Spreading of HOB Cells. Prior to the cell adhesion, cells were pre-incubated for 20 min with 150 µg/ml RGD peptide and/or 100 µg/ml to 400 µg/ml of the peptide respectively and the assay was performed in the absence of serum using FN and FN-TG2 matrices as stated in the Materials and Methods Each data points corresponds to the mean percentage of attached cells (cell attachment) or the mean percentage of spread cells (cell spreading). Mean values presented as the percentage of control (attached or spread cells on FN)+/−SD of triplicate measurements were taken as 100%. The mean percentage attachment value+/−SD normalised to 100% was 129.47+/−2.95 while the mean percentage spreading value+/−SD was 126.86+/−4.2. The statistically significant difference was shown as * ($p<0.05$) in the presence or absence of the RGD peptide in the test conditions. The ◇ symbol indicates the statistically different cell adhesion values ($p<0.05$) of points representing exemplary peptide treated cells with or without RGD peptide on FN-TG2 and FN matrices.

FIG. 15. Effect of Exemplary Peptide (GRDCSRRSS; SEQ ID NO:3) on TG2 Mediated RGD-Independent HOB Cell Adhesion on FN and FN-TG2 Matrices. HOB Cells were analyzed for attachment and spreading to FN and TG2 immobilised FN matrices as indicated under Materials and Methods Where indicated, cells were pre-treated with 100 µg/ml to 400 µg/ml of the peptide alone or in addition with 150 µg/ml RGD peptide for 20-25 min and then plated in the presence of these peptides. Each data point representing attached or spread cells on FN or FN-TG2 matrices is shown as a mean percentage+/−SD of two separate experiments performed in triplicate. The points in the upper and lower graphs representing different variables were expressed as percentage of control attachment or control spreading to FN+/−SD, respectively which stands for 100%. The mean value for cell attachment on FN was calculated as 129.47+/−2.95 while the mean number of cells spreading on FN+/−SD was 126.86+/−4.2 and considered as 100%. To show any statistical differences between obtained data points when compared to the control point they were calculated by t-test and shown as * ($p<0.05$) including both the presence and absence of RGD peptide on cell adhesion mediated by the exemplary peptide. In addition to indicate significant differences between the single data points symbol 0 ($p<0.05$) was applied.

FIG. 16. Effect of Exemplary Peptide Conjugate (BSA-Extended P1) on RGD-Dependent Cell Attachment. (A) HOB cells when plated onto BSA coated plates show no attachment. (C) When the same cells are plated onto the extended P1 peptide conjugated BSA, a small amount of attachment is observed in the presence of the RAD-containing control peptide, which is dramatically increased in the presence of soluble RGD containing peptide. (B) In contrast, when cells are plated onto fibronectin in the presence of soluble RGD peptide cell attachment is reduced (compared to the cell attachment in the presence of RAD control peptide).

EXAMPLE A

Abstract

Tissue transglutaminase (TG2) is a multifunctional protein crosslinking enzyme found in the intracellular and extracellular compartments. It is involved in stress related wound healing and implicated in metastatic cancer, celiac disease, and fibrosis. The multifunctional role of TG2 also extends to cell adhesion through a non transamidating mechanism through its high affinity for fibronectin (FN) and heparan sulfate proteoglycans (HSPG) and its integrin association. Only the fibronectin binding site of TG2 has been described, although its extent remains unknown. Here through both molecular modelling and mutagenesis we have identified the HS binding site of TG2 and demonstrate its importance for TG2 deposition into the ECM. We show how a mimic peptide corresponding to the heparan sulfate binding site can independently stimulate RGD-independent cell adhesion via binding to Syndecan-4 leading to activation of PKCα, pFAK-397 and ERK12. We demonstrate a novel regulatory mechanism for TG2 translocation and function in the extracellular compartment that depends upon TG2 conformation and coordinated binding of HS and FN.

Introduction

Transglutaminases are a family of enzymes which are characterised by their ability to generate ϵ(γ-glutamplysine cross-links between glutamine and lysine amino acid residues of peptides and proteins (Pisano et al., 1968). The resultant isopeptide bond is resistant to proteolytic cleavage and confers stability to the cross-linked product. Tissue transglutaminase (TG2) is found in a variety of cell types and has been ascribed a wide variety of functions (Griffin et al., 2002). It is important in the pathology of a number of diseases, such as celiac disease, metastatic cancer, kidney fibrosis and neurodegenerative disorders (Iismaa et al., 2009). Apart from its transglutaminase activity, TG2 also binds and hydrolyses GTP (Achyuthan and Greenberg, 1987; Bergamini et al., 1987; Lee et al., 1989) and ATP (Kawashima, 1991; Lai et al., 1996; Takeuchi et al., 1992), has protein disulphide isomerase (Hasegawa et al., 2003;

Mastroberardino et al., 2006) and serine/threonine kinase activities (Mishra and Murphy, 2004), although not all of these have been fully characterised. TG2 is found mainly in the cytosol and also in the nucleus and mitochondria (Krasnikov et al., 2005; Piacentini et al., 2002), with a small amount on the cell surface (Bruce and Peters, 1983) from where it is deposited into the ECM (Gaudry et al., 1999b; Upchurch et al., 1987; Upchurch et al., 1991). In its GTP-bound form associated with the inner surface of the plasma membrane, TG2 acts as a G-protein, resulting in the activation of PLC in response to α-adrenergic receptor binding (Nakaoka et al., 1994). Under stress conditions such as those found during tissue injury and wound healing, TG2 is translocated onto the cell surface or into the ECM where it can act as a matrix stabiliser via its protein cross-linking activity and also as a cell adhesion protein via its ability to bind to FN, heparan sulfate proteoglycans and integrins. Of these, only the FN binding site of TG2 has been described. The FN binding site of TG2 has been located to the N-terminal domain, and removal of the first seven N-terminal amino acid residues has been reported to abolish binding to FN (Gaudry et al., 1999a; Jeong et al., 1995). However, a later study disputed this and reported the FN binding site to be located between residues 81-140, with the peptide $^{88}$WTATVVDQQDCTLSLQLTT$^{106}$ (SEQ ID NO:5) able to inhibit the interaction between TG2 and a 42 kDa gelatin-binding proteolytic fragment of FN that is proposed to contain the TG2 binding site (Hang et al., 2005). Although this latter report did not repeat the initial experiment with a Δ1-7 TG2 deletion mutant, a Δ1-15 TG2 deletion mutant was demonstrated to not bind to the 42 kDa gelatin-binding fragment of FN.

Extracellular TG2 bound to matrix FN, namely TG-FN complex, can compensate for the loss of integrin-mediated cell adhesion induced by the RGD peptide treatment in a process requiring cell surface heparan sulfate (HS) chains, but independent of its transglutaminase enzymatic activity (Verderio et al., 2003a). Later reports demonstrated the involvement of an important member of the HSPG family, Syndecan-4, in this process leading to subsequent activation of PKCα, which in turn binds to β1 integrin and its intracellular signalling transduction mediated by FAK and ERK1/2, a process required for the cell adhesion, associated cytoskeletal changes and the FN fibril formation (Telci et al., 2008; Wang et al., 2010). TG2 binds with high affinity to heparin and this can be used for its purification (Yasueda et al., 1994). Although there are some proposed models for the interaction of TG2, Syndecan-4, FN and integrins in this process, the exact nature of the extracellular interaction is still not known.

The known heparin-binding sites of other proteins seem to share certain common features that have been used to identify the heparin-binding sites of uncharacterised proteins. For instance, many linear HS-binding motifs are composed of a particular organisation of basic amino acid residues, such as XBBXBX (SEQ ID NO:6) or XBBBXXBX (SEQ ID NO:7), where B is a basic amino acid whose side chain is exposed on the protein surface and X is a neutral or hydrophobic amino acid whose side chain is directed towards the protein interior (Cardin and Weintraub, 1989). Other motifs are composed of a 3D organisation of basic amino acid residues that are not necessarily adjacent to each other in the primary sequence (Hileman et al., 1998). Consequently, a combination of both sequence and structure analysis is required for the identification of novel HS binding motifs. The aim of this study was to identify the HS-binding site on TG2 using a combination of molecular modelling and site-directed mutagenesis. By demonstrating the importance of the HS binding site in TG2-mediated RGD-independent cell adhesion and by using both FN-binding defective TG2 mutants and the heparin binding mutant, we have been able to clarify the importance of these binding sites in the translocation of TG2 into the extracellular matrix.

Materials & Methods

Mammalian Cell Culture

Cell lines used in this study include human kidney epithelial cells HEK 293T/17 (ATCC CRL-11268) and mouse embryo fibroblasts NIH/3T3 (ATCC CRL-11268), Chinese hamster ovary cells CHO K1 (ATCC CCL-61) and the heparin sulfate deficient CHO-K1 derivative pgsD-677 (ATCC CRL-2244) (HS-mutant CHO), which were obtained from the American Type Culture Collection (ATCC, USA). Additionally, human osteoblasts (HOB) were kindly provided by Prof. S. Downes (University of Nottingham, Nottingham, UK). HEK 293T/17 cells, NIH/3T3 cells and HOB cells were cultured in Dulbecco's modified Eagle's medium (DMEM) containing 10% (v/v) heat-inactivated foetal bovine serum (FBS), 2 mM L-glutamine, nonessential amino acids, 100 U/ml of penicillin and 100 μg/ml of streptomycin. CHO-K1 and HS-mutant CHO cells were cultured in mixture F-12 (Ham) medium (Sigma-Aldrich, UK) supplemented with 10% (v/v) FBS. Above cells were all maintained at 37° C. in a 5% $CO_2$ humidified atmosphere.

Vector, Antibodies, Kits and Reagents

The pcDNA3.1 vector and the DH5α strain of *Escherichia coli* were purchased from Invitrogen (Paisley, UK). All restriction enzymes were obtained from New England Biolabs (Knowl Piece, UK). WIZARD® plus SV Minipreps DNA Purification system and WIZARD® SV gel and PCR Clean-up system were obtained from Promega (Southampton, UK). The endotoxin-free plasmid DNA maxi purification kit and the syndecan-4 targeting siRNA and its universal negative control siRNA were obtained from Qiagen (Crawley, UK). KOD HOT START DNA POLYMERASE® was obtained from Merck Chemical Ltd. (Nottingham, UK), QUIKCHANGE® II site directed mutagenesis kit was from Stratagene (Cheshire, UK). Cell transfection kits and reagents including NUCLEOFECTOR™ kit R used for transfection of NIH 3T3 cells was from Lonza Ltd. (Wokingham, Berkshire, UK). Mouse anti-TG2 monoclonal antibody Cub7402 was purchased from Thermo-Scientific (UK). Mouse anti-human p-397 FAK was purchased from Millipore (UK), anti-human p-ERK1/2, anti-ERK1/2 and anti-total FAK were from Santa Cruz (UK). The mouse anti-α-tubulin primary antibody and rabbit anti-mouse IgG-HRP conjugate secondary antibody were from Sigma-Aldrich (Dorset, UK). Guinea pig liver TG2 was purchased from Zedira (Darmstadt, Germany). The synthetic peptides GRGDTP (SEQ ID NO:8), GRADSP (SEQ ID NO:9) and the PKCα specific inhibitor Go6976 were obtained from Calbiochem (UK). The P1 peptide (NPKFLKNAGRDC-SRRSS; SEQ ID NO:2) and scrambled control peptide P1s (FNRADLKPRCGSSNKSR; SEQ ID NO:10), the peptide corresponding to the N-terminal end of TG2, AEELVLER-CDLELE (P2; SEQ ID NO:11) and the scrambled peptide EECRLAEELLEDVL (P2s; SEQ ID NO:12) were synthesized by Peptide Synthetics, Fareham UK. The GK21 peptide (GENPIYKSAVTTVVNPIYEGKRQIKIWFQNRRM-KWKK; SEQ ID NO:13) and its scrambled control peptide (GTAKINEPYSVTVPYGEKNKVRQIKIWFQNRRMK-WKK; SEQ ID NO:14) fused to the antennapedia third helix sequence (Parsons et al., 2002) were synthesized by Peptide Protein Research, UK.

Generation of the Wild Type TG2 and TG2 Mutants

Wild type (wt) human (Gentile et al., 1991) and C277S mutant (Lee et al., 1993) TG2 were amplified by PCR using primers TG2-F/TG2-R and cloned into the KpnI/NcoI sites of pcDNA3.1. The wt TG2 plasmid was then used to generate a set of TG2 mutants. These were constructed by either PCR in the case of Δ1-15 TG2, or by using the QUIKCHANGE® II site-directed mutagenesis kit (Stratagene, UK) for point mutations. Primers are shown in Table 1. The identity and proper arrangement of the TG2 mutants was verified by restriction analysis and nucleotide sequencing.

TABEL 1

Primers used in this study

| Name | TG2 Construct | Primer Sequence |
|---|---|---|
| TG2-F | TG2 | 5' GGTACCATGGCCGAGGAGCTG GTC 3' (SEQ ID NO: 15) |
| FN-F | D94A, D97A | 5' GGACAGCCACCGTGGTAGCCC AGCAAGCCTGCACCCTCTCGC 3' (SEQ ID NO: 16) |
| HS1-F | K600A, R601A, | 5' GGGGAGCCCAAGCAGGCGGCC GCGCTGGTGGCTGAGGTGTC 3' (SEQ ID NO: 17) |
| HS2-F | K602A | 5' CAACCCCAAGTTCCTGGCGAA CGCCGGCGCTGACTGCTCCCG 3' (SEQ ID NO: 18) |
| Δ1-15-F | K205A, R209A Δ1-15 TG2 | 5' GGACGGTACCATGACCAATGG CCGAGACCACCAC 3' (SEQ ID NO: 19) |
| TG2-R | | 5' GCGGCCGCTTAGGCGGGGCCAA TGATGAC 3' (SEQ ID NO: 20) |
| FN-R | TG2 | 5' GCGAGAGGGTGCAGGCTTGCTG GGCTACCACGGTGGCTGTCC 3' (SEQ ID NO: 21) |
| HS1-R | D94A, D97A | 5' GACACCTCAGCCACCAGCGCGG CCGCCTGCTTGGGCTCCCC 3' (SEQ ID NO: 22) |
| HS2-R | K600A, R601A, | 5' CGGGAGCAGTCAGCGCCGGCGT TCGCCAGGAACTTGGGGTTG 3' (SEQ ID NO: 23) |
| Δ 1-15-R | K602A K205A, R209A Δ 1-15 TG2 | 5' GGACGCGGAAGCTTAGGCGGGG CCAATGATGAC 3' (SEQ ID NO: 24) |

Transient Transfection and Expression of Wild Type TG2 and TG2 Mutants in Human HEK293T/17 Cells and Mouse NIH/3 T3 Cells HEK293T/17 cells and NIH/3T3 cells which express negligible or very low levels of endogenous TG2 were transiently transfected with wild type TG2 and the TG2 mutants. HEK293T/17 cells were transfected by the calcium phosphate procedure, whilst NIH/3T3 cells were transfected by electroporation (Lonza NUCLEOFECTOR™, kit R). Transfected cells were grown for 48 h at 37° C. in a 5% $CO_2$ humidified atmosphere to allow expression prior to analysis.

Syndecan 4 Silencing by siRNA Transfection

The HP GenomeWide siRNA sequences targeting human syndecan-4 (SI00046816) and the non-silencing (NS) control siRNA were obtained from Qiagen (UK). The target sequences are non-homologues for any other syndecan types or cell surface receptors. The transfection was performed according to the manufacturer's protocol. Briefly $3 \times 10^5$ cells/well HOB cells were seeded into 6-well plates for 24 h to reach 50-80% confluency. 150 ng of siRNAs were used for each transfection by using HIPERFECT® transfection reagents. Following 30 h siRNA transfection, the cells were used for cell adhesion assay (Wang et al., 2011).

Western Blotting

Cell lysates containing 50 µg of protein were dissolved in 2× Laemmli buffer (Sigma-Aldrich Ltd, Dorset, UK) and separated by SDS-PAGE. Western blotting was performed using specific primary antibodies as described above. Primary antibodies were detected using the appropriate secondary antibody conjugated to horse radish peroxidase. Detection was by chemiluminescence (Amersham ECL™ Western Blotting System, GE Healthcare, UK).

TABLE 2

Antibodies used in this study

| Antigen | Host species | Clone | Company |
|---|---|---|---|
| TG2 | Mouse | Monoclonal | Thermo Fisher |
| p-FAK397 | Mouse | Monoclonal | Millipore |
| Total FAK | Rabbit | Polyclonal | Santa Cruz |
| p-ERK1/2 | Rabbit | Polyclonal | Santa Cruz |
| Total ERK1/2 | Rabbit | Polyclonal | Santa Cruz |
| Syndecan-4 | Rabbit | Polyclonal | Invitrogen |
| Syndecan-2 | Rabbit | Polyclonal | Invitrogen |
| β1 Integrin | Rabbit | Polyclonal | Santa Cruz |
| α-Tubulin | Mouse | Monoclonal | Sigma-Aldrich |

Biotinylation of Cell Surface Proteins

Cell surface proteins were labelled by biotinylation as described previously (Wang et al., 2010). Briefly, cell monolayers were rinsed three times with ice-cold PBS pH 8.0 and labelled with 0.8 mM sulfo-NHS-LC-biotin dissolved in PBS pH 8.0 at 4° C. for 20 min. Cells were then washed with 50 mM Tris-HCl, pH 8.0 and lysed with 1% SDS at 4° C. in PBS pH8.0. Following denaturation at 95° C., cell lysates were clarified by centrifugation at 14,000×g at 20° C. and 200 µg of protein was incubated overnight at 4° C. with NEUTRAVIDIN® avidin protein-Agarose resin. After washing three times with PBS pH 8.0, the biotin-labelled proteins were dissolved in 2× Laemmli buffer separated by SDS-PAGE and subjected to Western blotting.

Detection of TG2 in Cell Culture Supernatant and in Extracellular Matrix (ECM)

Following transfection, cells were incubated for 24 h with 10% (v/v) serum, which was replaced with 1% (v/v) serum and TG2 expression was allowed to proceed for a further 48 h. Proteins from 1 ml of medium were precipitated by the addition of ice cold 20% (w/v) trichloroacetic acid (TCA) to a final concentration of 10% (w/v) Pelleted proteins were then washed once with ice cold 10% (w/v) TCA, ethanol-acetone (1:1) and acetone, and resuspended in 2× Laemmli buffer (Sigma-Aldrich, UK) and analysed by SDS-PAGE and Western blot analysis using monoclonal anti-TG2 antibody (Cub7402). The remaining cells were detached with 2 mM EDTA in PBS, pH 7.4 and the ECM was extracted with 0.1% (w/v) deoxycholate in PBS, pH 7.4. The residual deoxycholate-insoluble ECM proteins were dissolved in 2× Laemmli buffer for further analysis by SDS-PAGE and Western blotting using Cub7402.

Measurement of TG2 Binding to FN by ELISA

Microtitre 96 well plates were coated with 50 µl of 5 µg/ml FN in 50 mM Tris-HCl, pH 7.4 at 4° C. overnight. The wells were blocked for 30 min with 5% (w/v) fat-free milk in PBS, pH 7.4 and washed twice with PBS-TWEEN® detergent, pH 7.4 and once with PBS, pH 7.4. Aliquots (100

μl) of cell lysate containing 60 μg protein were added to the FN-coated wells and incubated for 1 h at 37° C. After washing three times with PBS, pH 7.4, wells were blocked with 100 μl 3% BSA in PBS, pH 7.4 (blocking buffer) for 30 min at room temperature and then incubated with 100 μl Cub7402 (1:1000 dilution in blocking buffer) for 2 h at 37° C. After washing three times with PBS, pH 7.4, the wells were incubated with 100 μl rabbit anti-mouse IgG-HRP conjugated antibody (1:1000 dilution in blocking buffer) for 2 h at 37° C. HRP was detected by the addition of 100 μl of o-phenylenediamine substrate solution (SigmaFast SIGMA-FAST™ OPD, Sigma). Colour development was terminated by the addition of 50 μl of 2.5M $H_2SO_4$ and absorbance at 490 nm was measured. The amount of TG2/mutant TG2 binding to the FN was normalised between samples by using the densitometry values from Western blotting for the TG protein found in each of the cell lysates used. α-Tubulin was used to normalise for any differences in protein loading.

Inhibition of Purified TG2 Binding to FN by TG2-Derived Peptides 96-well Microtitre 96-well plates were coated overnight with either full length FN (5 μg/ml), its 45 kDa (54 μg/ml) or 70 kDa (45 μg/ml) fragments, in 50 mM Tris-HCl, pH 7.4 as previously described (Verderio et al., 2003b). Wells were blocked with 3% BSA (w/v) in TBS pH 7.6. After three washes with PBS pH7.4, competitive peptides diluted in PBS, 2 mM EDTA, pH 7.4 were added to the wells at concentrations from 10 μM-1 mM and incubated for 1 h at room temperature. Wells were washed three times with PBS pH7.4 and purified human recombinant TG2 was added at a final concentration of 2 μg/ml in the presence of the different concentrations of P2 or P2s peptides and incubated for 1 h at room temperature. After three washes with PBS pH7.4 bound TG2 was measured via ELISA as introduced above. To detect the binding ability of TG2 when in either the fully closed or open conformation gpITG previously reduced by incubation with DTT was incubated with 1 mM GTP or GTPyS or 0.5 mM of TG2 inhibitor R281 or R283 (in the presence of 10 mM Ca2+) in 50 mM Tris-HCl, pH 7.4 for 30 min at room temperature. The treated TG2 was then detected by the ELISA assay as described above.

Binding of TG2 to Heparin SEPHAROSE®

HEK cells, transiently transfected with wild-type and mutant TG2 were washed twice with ice cold PBS, pH 7.4 and lysed by the addition of 150 μl of 20 mM Tris-HCl pH 7.4, 10 mM EGTA, 2 mM EDTA, 1 mM NaF and 1 mM $Na_3VO_4$. After clarification by centrifugation, lysates were mixed with 450 μl of 50 mM Tris-HCl, 1 mM EDTA, 1 mM DTT, pH 7.5 and applied to a 5 ml Heparin SEPHAROSE® column (GE Healthcare) equilibrated in 50 mM Tris-HCl, 1 mM EDTA, 1 mM DTT pH 7.5 (buffer) at a flow rate of 1 ml/min. For the analysis of GTP-bound TG2 (closed conformation), lysates were pre-incubated for 1 h at room temperature with 0.5 mM GTP in 50 mM Tris-HCl, 2 mM $MgCl_2$, 1 mM EDTA, 1 mM DTT pH 7.5. For the analysis of inhibitor-reacted TG2 (open conformation), lysates were incubated with 0.5 mM of irreversible inhibitor R281 (Griffin et al., 2008) and 10 mM $CaCl_2$. The column was washed with 25 ml of buffer and protein was eluted with a linear gradient of increasing NaCl concentration (0-1M) in buffer. Fractions were assayed for TG2 activity and analysed for the presence of TG2 antigen by SDS-PAGE and Western blotting using CUB7402.

Measurement of TG Activity in Cell Lysates and Heparin SEPHAROSE® Fractions

TG activity in column fractions was measured by biotin X-cadaverine incorporation into N,N'-dimethylcasein as described previously (Jones et al., 1997). After coating the wells with 100 μl of 10 mg/ml N,N'-dimethylcasein in 50 mM Tris-Cl, pH 8.0, plates were washed with TBS-0.05% TWEEN® detergent 20 (v/v), pH 7.6 and TBS, pH 7.6, and 50 μl of column flow-through as well as each eluted fraction was added into the coated wells. Additionally 50 μl of 100 mM Tris-Cl pH 8.0, 0.25 mM biotin X-cadaverine, 10 mM DTT, 20 mM $CaCl_2$ (or 5 mM EDTA as control) was added into each well. The reaction was allowed to proceed for 1 hour at 37° C. The plate was then washed once with TBS-0.05% TWEEN® detergent 20 (v/v), pH 7.6 and TBS, pH 7.6 before being blocked with 100 μl of 3% (w/v) BSA in TBS, pH 7.6) for 30 minutes at 37° C. After another wash, biotin X-cadaverine incorporation into N,N'-dimethylcasein was detected by incubation for 1 hour at 37° C. with 100 μl extravidin-peroxidase (Sigma-Aldrich, UK) diluted 1:2000 in 3% (w/v) BSA in TBS, pH 7.6. After another set of washes, TG2 activity was measured using SIGMAFAST™ OPD, tablets dissolved in 20 ml of distilled H20. The colour was developed by adding 2.5M H2SO4 and the absorbance at 490 nm measured using a microplate reader ELx808TM.

For cell lysates the incorporation of biotin-X-cadaverine into fibronectin as described by Jones et. al., 1997 was used. Briefly, wells of 96-well plate were coated with 5 μg/ml of fibronectin in a 50 mM Tris-Cl, pH 7.4 and incubated overnight at 4° C. After washing with 50 mM Tris-Cl, pH 7.4, wells were blocked with 3% (w/v) BSA in 50 mM Tris-Cl pH 7.4 for 30 minutes at 37° C. Enzyme reactions contained 50 ug of cell lysate protein in 50 mM Tris-Cl pH 7.4 buffer containing 5 mM $CaCl_2$ (or 5 mM EDTA as control), 10 mM DTT, 0.132 mM biotin X-cadaverine each done in triplicate. Reactions were allowed to proceed for 2 h at 37° C. Plates were the processed as described above.

Cell Adhesion Assay

The cell adhesion assay was carried out as previously described (Wang et al., 2010). Briefly, 96-well plastic tissue culture plates were coated with 5 μg/ml FN in 50 mM Tris-HCl, pH 7.4 at 4° C. overnight, after washing three times with 100 μl of 50 mM Tris-HCl, pH7.4, gpITG (20 μg/ml) in 2 mM EDTA in PBS, pH 7.4 was added to the wells for 1 h at 37° C. and the wells were washed three times with 50 mM Tris-HCl, pH7.4. Serum-starved (for 16 h) HOB cells with different treatments as introduced below in serum-free medium were detached by trypsinization and then treated with trypsin inhibitor. Cells were washed three times with serum free medium and seeded onto either FN or TG-FN matrix for 20-40 min. Peptides P1 or scrambled P1 (P1s), were added at concentrations between 100 μg/ml and 300 μg/ml. To determine the RGD-independent cell adhesion, assays were performed by incubating cells with either RGD or RAD peptide (100 μg/ml) in the presence of the P1 or P1s peptides for 20 min prior to seeding of the cells. Attached cells were washed once with PBS, pH 7.4 and then fixed with 3.7% paraformaldehyde, further permeabilised with 0.1% (v/v) Triton® X-100 detergent in PBS, and co-stained with May-Grunwald and Giemsa stains as described previously (Jones et al., 1997). Images of stained cells from non-overlapping fields of view were photographed at 20× magnification and analyzed using the imaging analysis program Scion Image (National Institute of Health). Cell attachment and spreading were quantified, and the number of cells per image was assessed as described previously (Telci et al., 2008). Cell attachment on FN without peptide was considered as the control value for all the experiments unless stated otherwise. The mean number of attached cells form three wells was calculated and that of the control was considered as 100%. The mean number of attached cells (cell attachment) for each sample was then expressed as the percentage of cell attachment on FN. The mean percentage of attached cells that are spread (cell spreading) for each sample was determined separately, and the mean percentage of spread cells on FN control was expressed as 100%. The mean percentage of spread cells for each sample was then normalised against that of FN control Cell attachment on FN without the RGD peptide was considered as the control value for most of the experiments unless stated otherwise The mean number of attached cells from three wells was calculated and that of the control was considered as 100%. The mean number of attached cells (cell attachment) for each sample was then expressed as the percentage of cell attachment on FN. The mean percentage of attached cells that are spread (cell spreading) for each sample was determined separately, and the mean percentage of spread cells on the FN control was expressed as 100%. The mean percentage of spread cells for each sample was then normalised against that of FN control Cell pre-treatments included: PKCα inhibitor Go6976 (5 µM) or GK21 peptide (8 µM) for 1 h in serum-free medium prior to cell detachment; heparinase (15 mU/ml) or chondroitinase (15 mU/ml) to cells in suspension in serum free medium for 1 h. For the detection of the signalling molecules via Western blotting, the cell adhesion assay was performed in 60 mm Petri dishes and cells were collected into cell lysis buffer (Santa Cruz, UK) as described previously and pre-cleared by centrifugation at 300×g for 10 min. Western blotting was performed with specific anti-p-397 FAK or p-ERK1/2 antibodies. Membranes were stripped (Telci et al., 2008) and total FAK and ERK1/2 detected using anti-FAK and anti-ERK1/2 antibodies as listed in Table 2, while α-tubulin was used as an equal loading standard (Wang et al., 2011).

Docking Studies

The crystal structures 1KV3 and 2Q3Z were downloaded as pdb files from the Protein Data Bank world-wide-web at resb.org and opened in the software CAChe WorkSystem Pro version 7.5.0.85 (Fujitsu Ltd). Hydrogens were added and waters and ions were deleted. Docking sites were defined by selecting all the amino acid residues within either 5 .ANG. or 8.ANG. of residues K202, K205, R209, R213 and R222. Both structures contained missing residues but these were far enough away from the defined docking sites such that their absence would not interfere with the docking studies. Using the same software, three ligand structures (a dimer, a pentamer and a hexamer) were defined by taking residues 2-3, 2-6 and 2-7 respectively from the glycosaminoglycan structure 1HPN.pdb. Using the ProjectLeader module and the ActiveSite docking component of the same software, the three ligands were each docked three times into the defined docking sites of both proteins using the flexible ligand and flexible active site side chain options. Other parameters and options included: Use Amber van der Waals; population size 50; maximum generations 3000; crossover Rate 0.8; mutation Rate 0.2; elitism number 5; local search rate 0.06; maximum iterations local search 300.

Data Analysis

Results shown are the mean±SD. The differences between data were calculated by Student's t test and presented as significant when the $p<0.05$.

Results

Identification of Putative Heparin-Binding Motifs in TG2

Examination of the primary amino acid sequence of TG2 for the linear consensus HS binding motifs XBBXBX (SEQ ID NO:6) and XBBBXXBX (SEQ ID NO:7), where B is a basic amino acid whose side chain is exposed on the protein surface and X is a neutral or hydrophobic amino acid whose side chain is directed towards the protein interior (Cardin and Weintraub, 1989), revealed one such sequence $^{261}$LRRWKN$^{266}$ (SEQ ID NO:25) close to the active site of TG2. This sequence has already been suggested as a possible HS binding site for TG2 (Verderio et al., 2009). However, examination of the crystal structure of TG2 (1KV3) shows that $^{261}$LRRWKN$^{266}$ (SEQ ID NO:25) is part of an alpha helix, whereas the XBBXBX consensus (SEQ ID NO:6) must be in a beta-sheet in order for the basic residues to face the same direction. A common structural theme of linear HS binding motifs is that there are two basic residues approximately 20 Å apart to accommodate a pentasaccharide, facing in opposite directions on an alpha helix (Margalit et al., 1993). Since $^{261}$LRRWKN$^{266}$ (SEQ ID NO:25) is too short to satisfy this requirement either, it is unlikely to be able to bind HS and so was not investigated. It has been suggested that the three dimensional arrangement of basic amino acid residues is more important than linear clustering, such that many HS binding motifs can also be comprised of sequence-distant basic amino acid residues (Hileman et al., 1998).

Two alternative candidate motifs were identified following detailed further examination of the crystal structure of TG2, $^{590}$KIRILGEPKQKRK$^{602}$ (HS1) (SEQ ID NO:26) which is located at the tip of C-terminal beta barrel 2 and another comprised of $^{202}$KFLKNAGRDCSRRSSPVYVGR$^{222}$ (SEQ ID NO:27), with K387 (HS2), forming a shallow pocket lined with basic residues (FIG. 1A-C).

A Heparin-Derived Oligosaccharide Docks into a Characteristic Heparin Binding Pocket in TG2

The HS1 and HS2 regions were docked with heparin derived oligosaccharides. An iduronic acid-2-sulfate-glucosamine-2,6-disulfate disaccharide, which is the most common repeating unit of heparin, docked well with the HS2 region of the closed form of TG2 (1KV3). In addition, a pentasaccharide with the same repeating units bound with a comparable enthalpy (FIG. 1D). However, the same oligosaccharides failed to dock with the open conformation of TG2 (2Q3Z). (Table 3)

TABLE 3

The scores (kcal/mol) of di-, penta-, and hexasaccharide docked into, or within the nearest localisation of the novel heparin binding site pocket localised on TG2

|  | 1KV3 5A site | 1KV3 8A site | 2Q3Z 5A site | 2Q3Z 8A site |
| --- | --- | --- | --- | --- |
| IDS-SGN | −548 | −602 | −574 | −627 |
| 2_6 | −836 | −710 | +1407 | −349 |
| 2_7 | −790 | −679 | +3706 | +9460 |

Modelling was undertaken using the Cache WorkSystem Proversion 7.5.0.85 (Fujitsu Ltd) software, the crystal structures of TG2 when adopted to a closed (1KV3) and extended (2Q3Z) conformations were docked with IDS-SGN (disaccharide), 2-6 (pentasaccharide) and 2-7 (hexasaccharide) and further verified for the binding efficiency into the HS2 binding pocket. The more negative the score, the higher binding efficiency.

Expression of TG2 FN and HSPG Mutants in Mammalian Cell Systems

Mutant TG2 enzymes for both the binding of FN (D94A, D97A), the N-terminal deletion (Δ1-15) and HS mutants HS1 (K600A, R601A, K602A) and HS2 (K205A, R209A) were generated by mutagenesis of plasmid pcDNA3.1-TG2 using the QUIKCHANGE® II site-directed mutagenesis kit (Stratagene) as detailed in the methods. Mutants were confirmed by nucleotide sequencing and transfected into HEK293T/17 cells and NIH 3T3 cells) and to assess expression. All mutants were expressed in both cell types (FIGS. 2A and 2D) and showed bands of the expected molecular weight as confirmed by Western blotting (FIGS. 2A and 2D) although at slightly different levels, with the Δ1-15 TG2 mutant showing the least expression and activity (FIGS. 2B-2F). Comparable transamidation activities were found with all mutants when normalised to TG2 protein (FIGS. 2C and 2F) apart from the Δ1-15 TG2 mutant which was around 50% lower than the wt enzyme in HEK cells but still present, suggesting no evidence of gross misfolding.

The High Affinity Heparin Binding Site of TG2 is Located in the Catalytic Core Domain TG2 binds to heparin SEPHAROSE® with high affinity, a property that has been exploited for its purification. The binding strength of TG2 and mutants HS1 and HS2, expressed in HEK293T/17 cells, to heparin SEPHAROSE® was determined by elution with an increasing salt gradient (FIG. 3). TG2 was eluted over a very broad peak ranging from 100 mM NaCl to 500 mM NaCl with optimum elution at 330 mM NaCl. To exclude the possibility that the observed low affinity binding was due to denatured TG2, the transglutaminase activity of eluted fractions was determined and this showed that specific activity did not differ significantly between the high and low affinity binding fractions (FIG. 11).

Mutant HS1 bound heparin identically to TG2, with low and high affinity, whereas mutant HS2 lost the capability to bind with high affinity to heparin, with a large percentage of the mutant showing no binding to the heparin column and the remainder showing low affinity binding and eluting at a NaCl concentration of 60 mM (FIG. 3), suggesting that residues K205 and R209 contribute to the high affinity binding to heparin. Since both mutants HS1 and HS2 resulted in the same net charge reduction, this alteration in HS2 binding was not simply due to electrostatic interaction. Comparable studies with the D94A, D97A FN mutant showed this mutant had a comparable elution profile to the wt enzyme however the Δ1-15 TG2 mutant showed only a low affinity binding to the heparin column with the major peaks eluting at around 250 mM NaCl.

High Affinity Heparin Binding is Dependent on TG2 Conformation

Since TG2 can adopt two extremes of conformation in the presence or absence of GTP, the effect of GTP binding on the association of TG2 to heparin was also investigated (FIG. 3). In the presence of GTP, which results in a compact globular conformation, all of the TG2 bound with high affinity to heparin with the major peak eluting at about 330 mM NaCl. In contrast, after reaction with the irreversible peptidic inhibitor R281 (Griffin et al., 2008) or mutation of the active site $Cys^{277}$ to Ser, which restricts the conformation to an extended form, the TG2 bound to heparin with lower affinity with the major peak eluting at 250 mM NaCl. Since the GTP-bound globular form of TG2 bound to heparin with high affinity whilst the extended R281-bound form still retained an affinity greater than that of the HS2 mutant, this suggests that the loss of high affinity binding of HS2 is not solely due to an altered conformation. Therefore, residues K205 and R209 in TG2 are very likely to be directly involved in high affinity heparin binding.

Cell Adhesion Studies with the HS2 Peptide NPKFLKNAGRDCSRRSS (P1; SEQ ID NO:2)

We next asked whether the peptide $^{200}$NPKFLKNAGRDCSRRSS$^{216}$ (P1; SEQ ID NO:2), which forms the major part of the loop that forms the proposed binding site of TG2 for HS, can mimic TG2 for the binding to cell surface Syndecan-4 and as such can either substitute for or abolish the TG2-mediated compensation of the RGD-mediated loss of cell adhesion. This peptide was chosen for its potential to fold correctly and the hydrophobic C-terminal sequence PVYVGR (SEQ ID NO:28), which had the potential to adversely affect solubility, was excluded. In our earlier studies using both human osteoblasts (HOB) and mouse embryonic fibroblast (MEF) cells, it was shown that extracellular TG2 bound to matrix FN could compensate for the loss of integrin-mediated cell adhesion in the presence of RGD peptides in a process requiring cell surface syndecan-4, but not its transamidase activity (Scarpellini et al., 2009). Since direct interaction of TG2 with syndecan-4 is essential for this process, the HSPG binding properties of TG2 are therefore critical. The peptide NPKFLKNAGRDCSRRSS (P1; SEQ ID NO:2) was therefore tested for its ability to compensate RGD-induced loss of cell adhesion on FN in human osteoblasts. Using the peptide at a concentration between 0.01-200 μg/ml it can be seen that compensation of loss of adhesion started as low as 5-10 μg/ml with maximum compensation achieved between 50-100 ug/ml (FIGS. 4A and 4B). We next investigated whether the P1 peptide when used at a concentration of 100 ug/ml could compete for the binding of syndecan-4 and abrogate the compensatory effects of TG2-FN, when the cells were plated onto the TG-FN matrix in the presence of the RGD peptide. The scrambled analogue FNRADLKPRCGSSNKSR (P1s; SEQ ID NO:10) was used as a control in these experiments. It can be seen from FIG. 4C that peptide NPKFLKNAGRDCSRRSS (SEQ ID NO:2) only has a small, but not significant dose-dependent negative effect on the attachment and spreading of HOB cells on TG-FN in the presence of the RGD peptide, whereas the scrambled peptide (P1s) control had almost no effect. This suggests that even though the peptide may compete for TG2 for the syndecan-4 binding site its ability to mimic TG2 in compensating RGD-induced loss of cell adhesion means no large changes in cell adhesion are likely to be observed. Neither of these peptides adversely affected the binding of cells to FN alone in any significant manner when used at similar concentrations of 100-300 μg/ml, although a small but significant enhancement of adhesion was found for P1 peptide when compared to the P1 s peptide (FIG. 4C).

P1 Peptide Acts Via Binding and Activation of Syndecan 4-Mediated Cell Signalling To test the importance of cell surface HS in the binding of P1 peptide, HOB cells were pre-treated with heparinase or chondroitinase prior to the cell adhesion assay. When cells were treated with heparinase, but not chondroitinase, it was found that the compensatory effect of the P1 peptide on the RGD-induced loss of cell adhesion was abolished (FIG. 4D). To confirm that the cell surface HS chains that the P1 peptide is binding to are from cell surface Syndecan-4 molecules, HOB cells were treated with syndecan-4 siRNA and scrambled control siRNA as previously documented (Wang et al., 2011). As previously found (Wang et al., 2011) treatment of cells with syndecan-4 siRNA led to a around 50% reduction in protein expression (FIG. 12) without affecting either Syndecan-2 or β1 integrin, another two major players in the TG-FN complex-mediated signalling pathway (Wang et al., 2010), with a comparable reduction in the compensatory effect for the P1 peptide on the RGD-induced loss of cell adhesion (FIG. 4E). The scrambled siRNA had no significant effect on either expression or cell adhesion, further confirming the essential role of Syndecan-4 in the P1 peptide-related cell adhesion process.

Since we have demonstrated that TG2 acts via direct binding of Syndecan-4 leading to activation of PKCα, our next step was to demonstrate the activation of PKCα in the signalling effects mediated by the P1 peptide. Using the PKCα inhibitor Go6976 and the GK21 peptide (which competes with the PKCα binding site on β1 integrin), it was shown (FIGS. 5A and 5B) that both of these different inhibitors of PKCα activation led to inhibition of the compensatory effect of the P1 peptide on the RGD-induced loss of cell adhesion, thus strongly suggesting that the P1 peptide is acting in a comparable signalling manner to that of TG2 in its compensatory effect. To confirm our observations that the P1 peptide is inducing intracellular signalling pathways comparable to the TG-FN matrix we also looked at the activation of FAK by phosphorylation at Tyrosine 397 (FIGS. 6A and 6B) and phosphorylation of ERK1/2 (FIGS. 6C and 6D). In each case, in the presence of RGD and P1 peptide the compensation of the RGD-induced loss of adhesion was paralleled by the phosphorylation of p-FAK397 and p-ERK1/2 which was not found with the scrambled P1 peptide (P1s) and was comparable to that found with the TG2-FN matrix in the presence of RGD.

The N-Terminus of TG2 is Involved in FN Binding

The Δ1-15 and D94A, D97A TG2 mutants were assessed for their ability to bind to FN in a solid phase binding assay utilising purified FN and lysates from HEK293T/17 cells transfected with the different mutants. The D94A, D97A mutant described previously (Hang et al., 2005) demonstrated approximately 50% binding compared to wild type TG2, whereas the Δ1-15 deletion mutant previously described (Hang et al., 2005) had approximately 40% of the binding capacity of the wild type (FIG. 7A). A competitive peptide was synthesised corresponding to the N-terminal deletion site of TG2 $^2$AEELVLERCDLELE$^{15}$ (P2; SEQ ID NO:11) (TG2 undergoes N terminal post-translational modification of the N-terminal methionine) and then tested for its ability to inhibit wild type TG2 binding to FN and the smaller FN fragments of 45 and 70 Kda in a solid binding assay. The P2 peptide resulted in a moderate but significant inhibition of binding to FN and its smaller fragments at higher concentrations of the peptide (FIG. 7B) suggesting that the N-terminal residues 1-15 of TG2 may be important for FN binding, in addition to the published D94A, D97A. No effect was observed with the scrambled P2s peptide (FIG. 7C). However, the limited inhibition seen with this peptide suggests that the FN binding site around the N-terminal site of TG2 may be more complex and that a larger structural unit than that described previously (Hang et al., 2005) may be involved in FN binding.

FN and HS Binding are Required for ECM Localisation

Given earlier data suggesting that cell surface heparan sulfates may be important in the translocation of TG2 at the cell surface (Scarpellini et al., 2009), we investigated the ability of the FN and HS mutants to be secreted to the cell surface and/or deposited into the ECM. Using transfected NIH/3T3 fibroblasts, the cellular localisation of the D94A, D97A FN mutant, the Δ1-15 mutant and the HS1 and HS2 TG2 mutants were tested for their presence at the cell surface using the cell surface biotinylation assay combined with Western blotting. For detecting the presence of these mutant TG2s in the ECM, transfected NIH/3T3 cells, which actively deposit ECM, were first removed with EDTA and then the ECM was washed with deoxycholate buffer to remove cell debris. The remaining matrix was then analysed by Western blotting for the presence of matrix bound wild-type and mutant enzymes. Using this assay, TG2 Δ1-15 was not detected on the cell surface of the NIH3T3 cells (FIG. 8A) whereas the HS2 mutant was detected but in reduced amounts compared to the wild-typeTG2. In contrast the levels of the FN mutant D94A, D97A and the HS1 mutant were found at greater levels on the cell surface than that shown for wild-type TG2 (FIG. 8A). A comparable picture was observed for the presence of the enzymes in the ECM of NIH 3T3 cells apart for the HS2 mutant which was not detectable within the matrix (FIG. 8B). When the spent culture from the cells was assayed for the presence of the Δ1-15 mutant and the HS2 mutant, both enzymes were detectable, with the majority present in high MW polymers unable to enter the resolving gel (FIG. 8C).

Cellular Localisation of TG2 in CHO Wt and CHO-HS-M Cells

To confirm the importance of cell surface heparan sulfates in the cell surface and matrix distribution of TG2, the HS deficient CHO-K1 derivative pgsD-677 were compared to wt CHO-K1 cells with respect to their distribution of TG2 at the cell surface, in the ECM and in the culture medium. FIGS. 9A and 9B clearly demonstrate that the amount of TG2 found at the cell surface and in the matrix in the CHO mutant cells is considerably reduced when compared to the wt cells. Moreover, TG2 present in the medium (FIG. 9C) could not be found in either cell type although an immunoreactive high Mr band unable to enter the resolving gel was found in the wt cells as previously found in the mutant HS2 cells.

Discussion

In this Example, we sought to define more clearly the role of FN and HS in the translocation of TG2 to the cell surface and in its subsequent deposition into the ECM. These particular binding partners are important since together with TG2 they play an important role in a novel cell adhesion mechanism whereby TG2 acts as a scaffold protein bridging the interaction between FN and cell surface HS. The mechanism is independent of transamidation activity and does not require integrin binding but requires the direct binding of TG2 to the HS chains of Syndecan-4. This interaction results in activation of PKCα, leading to an increase in FAK phosphorylation and focal adhesion assembly (Wang et al., 2010).

Our first step was to identify the major HS binding site on TG2 that facilitates its interaction with Syndecan-4 and which can potentially regulate and direct its different functions at the cell surface (Verderio et al., 2009). This was undertaken using a combination of amino acid sequence analysis for known HSPG-binding motifs and analysis of the available crystal structures of TG2 for potential binding pockets. Using this methodology, two potential binding sites were eventually identified (HS1 and HS2) which were subjected to site directed mutagenesis of key surface-exposed basic residues. Binding studies were undertaken on the wt TG2 and mutant TG2 proteins using a heparin affinity chromatography column which showed that the HS2 site, comprising residues $^{202}$KFLKNAGRDCSRRSSPVYVGR$^{222}$ [SEQ ID NO: 27], was required for high affinity binding to heparin, unlike the HS1 site. This binding site does not possess a characteristic sequence like other HSPG-binding sites described in the literature, but comprises a shallow pocket lined with basic amino acid residues that are orientated to interact favourably with the functional groups of sugar phosphates. TG2 can adopt two extremes of conformation: a compact conformation when guanine nucleotides are bound and an extended conformation when guanine nucleotides have been displaced by calcium binding. This extended form is the catalytically active transglutaminase and these conformational changes have been confirmed in solution by physical methods (Casadio et al., 1999; Mariani et al., 2000) and also after x-ray crystallographic analysis of GDP-bound (Liu et al., 2002) and activated forms (Pinkas et al., 2007). Surprisingly, although our docking studies predicted a good interaction between the HS-binding site of the compact form of TG2 and heparin oligosaccharides, the extended conformation did not produce any favourable interactions. The HS-binding site is significantly altered between the two known conformations and suggests that binding affinities for TG2 and heparin might be conformation-dependent. Using heparin affinity chromatography, we confirmed that GTP-bound TG2 (compact conformation) binds strongly to heparin (eluted at 330 mM NaCl), whereas R281-reacted TG2 (extended conformation) binds weaker (eluted at 250 mM NaCl). Interestingly the C277S mutant that is known to be in the extended conformation bound to heparin with a similar affinity to that of R281-reacted TG2. It is therefore likely that under normal physiological conditions the degree of specificity of TG2 for HS may be conformation dependent.

Mutation of two surface exposed basic residues (K202 and R205) in the HS2 site did not affect TG2 activity, or FN binding, suggesting that these mutations do not affect the folding or structure of the core domain. However, this mutant only bound very weakly to heparin, with one large pool of mutant eluting from the heparin SEPHAROSE® column at 60 mM NaCl and another active pool of enzyme failing to bind at all. Both of these pools of eluted enzyme showed full TG activity (FIG. 11), suggesting that failure to bind strongly to heparin was not due to misfolding or gross conformational changes. Hence the affinity of the K205, R209 mutant for heparin is significantly lower than that of either GTP-bound or R281-reacted wild-type TG2 and it is likely that no binding would occur at physiological ionic strength. The HS2 mutant was found in low amounts on the cell surface and was absent from the matrix, although it could be detected in the spent culture supernatant. This supports the idea (Scarpellini et al., 2009) that HSPG-binding is crucial for TG2 localisation at the cell surface and in addition for its deposition into the matrix. Since the HS2 mutant retained its ability to bind to FN, cell-mediated matrix deposition of TG2 cannot be mediated by FN binding alone. In order to confirm the importance of HS in the regulation of TG2 distribution at the cell surface, CHO cells which are unable to synthesise HS but are still able to maintain the presence of the core proteins of the proteoglycans in the cell membrane (Lidholt et al., 1992) were used. Distribution of TG2 at the cell surface and in the matrix of CHO mutant cells and in wt CHO cells paralleled what was seen with the HS2 TG2 mutant, with reduced levels of TG2 found at the cell surface and very little enzyme present in the matrix.

A multiple alignment of TG peptide sequences, including TG2 from different species and human TG isoforms (FIG. 9D) shows that the high affinity heparin binding domain is conserved amongst TG2 enzymes, but is absent from other isoforms. Residues corresponding to human TG2 positions 202, 205, 213 and 222 are conserved as basic residues amongst all the TG2 sequences analysed, whereas there are substitutions corresponding to position 209 (R→Q) in guinea pig TG2 and positions 209 (R→L) and 387 (K→Q) in chicken TG2. The physiological significance of these substitutions is, as yet, unknown.

It has been reported that the FN binding site of TG2 involves a region in the N-terminal domain of TG2, corresponding to residues [88]WTATVVDQQDCTLSLQLTT[106] [SEQ ID NO: 5] (Hang et al., 2005). In addition, other reports suggest that the amino terminus of the TG2 is also important for FN binding (Gaudry et al., 1999a; Jeong et al., 1995). To investigate the effects of these mutations on TG2 localisation, we made mutations in both these regions. Both mutants showed reduced FN binding, although in a comparable assay the N-terminal domain mutant appeared to bind to FN with slightly less affinity but our data confirmed that both of these regions are important. Interestingly, in contrast to the D94A, D97A mutant which bound to heparin SEPHAROSE® in a similar way to the wild type TG2, the Δ1-15 TG2 mutant only bound with a reduced affinity similar to that of the C277S mutant and R281-reacted TG2. This may be due to a conformational change in TG2 (possibly to an open form) induced by N-terminal deletion or possibly suggests that heparin binding can be influenced by the N-terminal region. In addition, whereas the D94A, D97A mutant showed the same level of cell surface and matrix localisation as the wild type, the Δ1-15 TG2 mutant could not be observed on the cell surface or in the matrix, initially suggesting that the lack of strong HS binding as opposed to loss of FN binding was responsible. However, both in the CHO mutant cells and in the cells transfected with the HS2 TG2 mutant a small amount TG2 is found at the cell surface, suggesting TG2 may be binding to some other component in addition to HS, which is probably FN since TG2 was absent at the cell surface of the Δ1-15 TG2 mutant in which both FN binding and HS binding was reduced.

It is still not fully understood what mechanism TG2 uses for its externalisation. Reference to the literature suggests that TG2 conformation may be important in this process. For example, C277S is thought to lock TG2 in an open conformation under physiological conditions and prevents deposition into the matrix although it is still found at the cell surface (Gaudry et al., 1999a). K173L, which does not bind GTP is not externalised, although the native conformation of this mutant has not yet been determined (Johnson and Terkeltaub, 2005). In contrast, the S171E mutant (which abolishes GTP binding) which is locked in the open conformation, was found on the cell surface.

Mutation Y274A, which is thought to prevent the transition between open and closed conformations, also prevents secretion (Johnson and Terkeltaub, 2005). Using this information and the data obtained for binding of the TG2 mutants to heparin one might envisage a mechanism whereby TG2 is first externalised in its closed GTP-bound conformation. It is then retained at the cell surface by its immediate high affinity binding to HS at physiological ionic strength. However, once exposed to $Ca^{2+}$, it adopts an open conformation and the affinity for HS is significantly reduced, whereas its affinity for FN is not altered (FIG. 13) and it can leave the cell surface bound to FN, in a transamidation-active form (FIG. 10). Importantly binding to FN is also capable of modulating its transamidating activity (Lemosy et al., 1992) such that under normal conditions uncontrolled crosslinking does not occur. Under certain conditions TG2 may also be deposited into the matrix by the process of HS shedding which is known to occur during wound healing when greater amounts of active TG2 may be required (Couchman et al., 2010). Subsequent oxidation or nitrosylation of the matrix bound enzyme then further modulates its transamidating activity (Stamnaes et al., 2010) such that the enzyme may then act as a novel FN bound cell adhesion protein (Akimov et al., 2000; Verderio et al., 2003b) which is independent of its transamidating activity.

Having identified the major heparan sulfate binding site on TG2, we next demonstrated that the peptide representing the proposed binding pocket on TG2 for HS (P1; SEQ ID NO:2) could act in a similar way to TG2 in mediating RGD-independent cell adhesion. This was undertaken by looking at the ability of the HS2 derived peptide at different concentrations to compensate RGD-induced loss of cell adhesion when human osteoblasts are plated onto FN (Wang et al., 2011). Even at concentrations as low as 5-10 ug/ml compensation of cell adhesion was noted indicating the potency of this interaction. Importantly this compensatory effect could be abrogated by pretreatment of cells with heparinase but not chondroitinase indicating it to be HS mediated. Moreover treatment of cells with Syndecan-4 siRNA led to a similar inhibition to heparinase on the peptides compensatory effects indicating like TG2 the P1 peptide is binding to cell surface HS of Syndecan-4.

Further confirmation that this HS2 derived peptide is capable of mimicking the HS binding site on TG2 was obtained by analysis of the downstream signalling events during its compensatory effect on cell adhesion in the presence of RGD peptides. Like the TG2-FN complex, binding of the peptide to Syndecan4 stimulated activation of PKCα, which was demonstrated using the pharmacological inhibitor Go6976 and by the GK21 peptide that blocks PKCα from binding to one of its targets β1 integrin in the cell signalling process. Downstream of PKCα activation we also demonstrate that in common with TG2, binding to Syndecan-4 results in activation of FAK by phosphorylation of Tyr 397 which led to the subsequent activation of ERK1/2 as evidenced by the use of Western blotting. In conclusion we have identified the HS binding site on TG2 thus confirming the importance and requirement of these important cell surface molecules in the extracellular translocation and function of TG2. Importantly we show how a mimic peptide of the HS binding site on TG2 can stimulate RGD-independent cell adhesion by a mechanism involving binding to cell surface HS and activation of PKCα. Finally, we propose a novel mechanism of how cell surface HS and FN, the high affinity binding partners of TG2, are important in regulating TG2 translocation and function in the extracellular matrix.

REFERENCES

Achyuthan, K. E., and C. S. Greenberg. 1987. Identification of a guanosine triphosphate-binding site on guinea pig liver transglutaminase. Role of GTP and calcium ions in modulating activity. *J Biol Chem.* 262:1901-6.

Akimov, S. S., D. Krylov, L. F. Fleischman, and A. M. Belkin. 2000. Tissue transglutaminase is an integrin-binding adhesion coreceptor for fibronectin. *Journal of Cell Biology.* 148:825-838.

Bergamini, C. M., M. Signorini, and L. Poltronieri. 1987. Inhibition of Erythrocyte Transglutaminase by Gtp. *Biochimica Et Biophysica Acta.* 916:149-151.

Bruce, S. E., and T. J. Peters. 1983. The subcellular localization of transglutaminase in normal liver and in glucagon-treated and partial hepatectomized rats. *Biosci Rep.* 3:1085-90.

Cardin, A. D., and H. J. R. Weintraub. 1989, Molecular Modeling of Protein-Glycosaminoglycan Interactions. *Arteriosclerosis.* 9:21-32.

Casadio, R., E. Polverini, P. Mariani, F. Spinozzi, F. Carsughi, A. Fontana, P. P. de Laureto, G. Matteucci, and C. M. Bergamini. 1999. The structural basis for the regulation of tissue transglutaminase by calcium ions. *European Journal of Biochemistry.* 262:672-679.

Couchman, J. R., T. Manon-Jensen, and Y. Itoh. 2010. Proteoglycans in health and disease: the multiple roles of syndecan shedding. *Febs Journal.* 277:3876-3889.

Gaudry, C. A., E. Verderio, D. Aeschlimann, A. Cox, C. Smith, and M. Griffin. 1999a. Cell surface localization of tissue transglutaminase is dependent on a fibronectin-binding site in its N-terminal beta-sandwich domain. *Journal of Biological Chemistry.* 274:30707-30714.

Gaudry, C. A., E. Verderio, R. A. Jones, C. Smith, and M. Griffin. 1999b. Tissue transglutaminase is an important player at the surface of human endothelial cells: Evidence for its externalization and its colocalization with the beta(1) integrin. *Experimental Cell Research.* 252:104-113.

Gentile, V., M. Saydak, E. A. Chiocca, O. Akande, P. J. Birckbichler, K. N. Lee, J. P. Stein, and P. J. A. Davies. 1991. Isolation and Characterization of Cdna Clones to Mouse Macrophage and Human Endothelial-Cell Tissue Transglutaminases. *Journal of Biological Chemistry.* 266: 478-483.

Griffin, M., R. Casadio, and C. M. Bergamini. 2002. Transglutaminases: Nature's biological glues. *Biochemical Journal.* 368:377-396.

Griffin, M., A. Mongeot, R. Collighan, R. E. Saint, R. A. Jones, I. G. C. Coutts, and D. L. Rathbone. 2008. Synthesis of potent water-soluble tissue transglutaminase inhibitors. *Bioorganic & Medicinal Chemistry Letters.* 18:5559-5562.

Hang, J., E. A. Zemskov, L. Lorand, and A. M. Belkin. 2005. Identification of a novel recognition sequence for fibronectin within the NH2-terminal beta-sandwich domain of tissue transglutaminase. *J Biol Chem.* 280: 23675-23683.

Hasegawa, G., M. Suwa, Y. Ichikawa, T. Ohtsuka, S. Kumagai, M. Kikuchi, Y. Sato, and Y. Saito. 2003. A novel function of tissue-type transglutaminase: protein disulphide isomerase. *Biochemical Journal.* 373:793-803.

Hileman, R. E., J. R. Fromm, J. M. Weiler, and R. J. Linhardt. 1998. Glycosaminoglycan-protein interactions: definition of consensus sites in glycosaminoglycan binding proteins. *Bioessays.* 20:156-167.

Iismaa, S. E., B. M. Mearns, L. Lorand, and R. M. Graham. 2009. Transglutaminases and disease: lessons from genetically engineered mouse models and inherited disorders. *Physiol Rev.* 89:991-1023.

Jeong, J. M., S. N. Murthy, J. T. Radek, and L. Lorand. 1995. The fibronectin-binding domain of transglutaminase. *J Biol Chem.* 270:5654-8.

Johnson, K. A., and R. A. Terkeltaub. 2005. External GTP-bound transglutaminase 2 is a molecular switch for chondrocyte hypertrophic differentiation and calcification. *J Biol Chem.* 280115004-12.

Jones, R. A., B. Nicholas, S. Mian, P. J. A. Davies, and M. Griffin. 1997. Reduced expression of tissue transglutaminase in a human endothelial cell line leads to changes in cell spreading, cell adhesion and reduced polymerisation of fibronectin. *Journal of Cell Science.* 110:2461-2472.

Kawashima, S. 1991. Inhibition of rat liver transglutaminase by nucleotides. *Experientia.* 47:709-12.

Krasnikov, B. F., R. R. Ratan, G. E. Gibson, S. Iismaa, and A. J. Cooper. 2005. Transglutaminase activity in non-synaptosomal mouse brain and liver mitochondria. *Journal of Neurochemistry.* 94:41-41.

Lai, T. S., T. F. Slaughter, C. M. Koropchak, Z. A. Haroon, and C. S. Greenberg. 1996. C-terminal deletion of human tissue transglutaminase enhances magnesium-dependent GTP/ATPase activity. *Journal of Biological Chemistry*. 271:31191-31195.

Lee, K. N., S. A. Arnold, P. J. Birckbichler, M. K. Patterson, Jr., B. M. Fraij, Y. Takeuchi, and H. A. Carter. 1993. Site-directed mutagenesis of human tissue transglutaminase: Cys-277 is essential for transglutaminase activity but not for GTPase activity. *Biochim Biophys Acta*. 1202:1-6.

Lee, K. N., P. J. Birckbichler, and M. K. Patterson, Jr. 1989. GTP hydrolysis by guinea pig liver transglutaminase. *Biochem Biophys Res Commun*. 162:1370-5.

Lemosy, E. K., H. P. Erickson, W. F. Beyer, J. T. Radek, J. M. Jeong, S. N. P. Murthy, and L. Lorand. 1992. Visualization of Purified Fibronectin-Transglutaminase Complexes. *Journal of Biological Chemistry*. 267:7880-7885.

Lidholt, K., J. L. Weinke, C. S. Kiser, F. N. Lugemwa, K. J. Bame, S. Cheifetz, J. Massague, U. Lindahl, and J. D. Esko. 1992. A Single Mutation Affects Both N-Acetylglucosaminyltransferase and Glucuronosyltransferase Activities in a Chinese-Hamster Ovary Cell Mutant Defective in Heparan-Sulfate Biosynthesis. *Proceedings of the National Academy of Sciences of the United States of America*. 89:2267-2271.

Liu, S. P., R. A. Cerione, and J. Clardy. 2002. Structural basis for the guanine nucleotide-binding activity of tissue transglutaminase and its regulation of transamidation activity. *Proceedings of the National Academy of Sciences of the United States of America*. 99:2743-2747.

Margalit, H., N. Fischer, and S. A. Bensasson. 1993. Comparative-Analysis of Structurally Defined Heparin-Binding Sequences Reveals a Distinct Spatial-Distribution of Basic Residues. *Journal of Biological Chemistry*. 268:19228-19231.

Mariani, P., F. Carsughi, F. Spinozzi, S. Romanzetti, G. Meier, R. Casadio, and C. M. Bergamini. 2000. Ligand-induced conformational changes in tissue transglutaminase: Monte Carlo analysis of small-angle scattering data. *Biophysical Journal*. 78:3240-3251.

Mastroberardino, P. G., M. G. Farrace, I. Viti, F, Pavone, G. M. Fimia, G. Melino, C. Rodolfo, and M. Piacentini. 2006. "Tissue" transglutaminase contributes to the formation of disulphide bridges in proteins of mitochondrial respiratory complexes. *Biochimica Et Biophysica Acta-Bioenergetics*. 1757:1357-1365.

Mishra, S., and L. J. Murphy. 2004. Tissue transglutaminase has intrinsic kinase activity—Identification of transglutaminase 2 as an insulin-like growth factor-binding protein-3 kinase. *Journal of Biological Chemistry*. 279:23863-23868.

Nakaoka, H., D. M. Perez, K. J. Baek, T. Das, A. Husain, K. Misono, M. J. Im, and R. M. Graham. 1994. G(H)—a Gtp-Binding Protein with Transglutaminase Activity and Receptor Signaling Function. *Science*. 264:1593-1596.

Parsons, M., M. D. Keppler, A. Kline, A. Messent, M. J. Humphries, R. Gilchrist, I. R. Hart, C. Quittau-Prevostel, W. E. Hughes, P. J. Parker, and T. Ng. 2002. Site-directed perturbation of protein kinase C-integrin interaction blocks carcinoma cell chemotaxis. *Molecular and Cellular Biology*. 22:5897-5911.

Piacentini, M., M. G. Farrace, L. Piredda, P. Matarrese, F. Ciccosanti, L. Falasca, C. Rodolfo, A. M. Giammarioli, E. Verderio, M. Griffin, and W. Malorni. 2002. Transglutaminase overexpression sensitizes neuronal cell lines to apoptosis by increasing mitochondrial membrane potential and cellular oxidative stress. *Journal of Neurochemistry*. 81:1061-1072.

Pinkas, D. M., P. Strop, A. T. Brunger, and C. Khosla. 2007. Transglutaminase 2 undergoes a large conformational change upon activation. *Plos Biology*. 5:2788-2796.

Pisano, J. J., J. S. Finlayson, and M. P. Peyton. 1968. [Cross-link in fibrin polymerized by factor 13: epsilon-(gamma-glutamyl)lysine]. *Science*. 160:892-3.

Scarpellini, A., R. Germack, H. Lortat-Jacob, T. Muramatsu, E. Billett, T. Johnson, and E. A. M. Verderio. 2009. Heparan Sulfate Proteoglycans Are Receptors for the Cell-surface Trafficking and Biological Activity of Transglutaminase-2. *Journal of Biological Chemistry*. 284:18411-18423.

Stamnaes, J., D. M. Pinkas, B. Fleckenstein, C. Khosla, and L. M. Sollid. 2010. Redox Regulation of Transglutaminase 2 Activity. *Journal of Biological Chemistry*. 285:25402-25409.

Takeuchi, Y., P. J. Birckbichler, M. K. Patterson, and K. N. Lee. 1992. Putative Nucleotide Binding-Sites of Guinea-Pig Liver Transglutaminase. *Febs Letters*. 307:177-180.

Telci, D., Z. Wang, X. Li, E. A. M. Verderio, M. J. Humphries, M. Baccarini, H. Basaga, and M. Griffin. 2008. Fibronectin-tissue transglutaminase matrix rescues RGD-impaired cell adhesion through syndecan-4 and beta(1) integrin co-signaling. *Journal of Biological Chemistry*. 283:20937-20947.

Upchurch, H. F., E. Conway, M. K. Patterson, P. J. Birckbichler, and M. D. Maxwell. 1987. Cellular Transglutaminase Has Affinity for Extracellular-Matrix. *In Vitro Cellular & Developmental Biology*. 23:795-800.

Upchurch, H. F., E. Conway, M. K. Patterson, and M. D. Maxwell. 1991. Localization of Cellular Transglutaminase on the Extracellular-Matrix after Wounding—Characteristics of the Matrix Bound Enzyme. *Journal of Cellular Physiology*. 149:375-382.

Verderio, E. A., D. Telci, A. Okoye, G. Melino, and M. Griffin. 2003a. A novel RGD-independent cel adhesion pathway mediated by fibronectin-bound tissue transglutaminase rescues cells from anoikis. *J Biol Chem*. 278:42604-14.

Verderio, E. A. M., A. Scarpellini, and T. S. Johnson. 2009. Novel interactions of TG2 with heparan sulfate proteoglycans: reflection on physiological implications. *Amino Acids*. 36:671-677.

Verderio, E. A. M., D. Telci, A. Okoye, G. Melino, and M. Griffin. 2003b. A novel RGD-independent cell adhesion pathway mediated by fibronectin-bound tissue transglutaminase rescues cells from anoikis. *Journal Of Biological Chemistry*. 278:42604-42614.

Wang, Z., R. J. Collighan, S. R. Gross, E. H. J. Danen, G. Orend, D. Telci, and M. Griffin. 2010. RGD-independent Cell Adhesion via a Tissue Transglutaminase-Fibronectin Matrix Promotes Fibronectin Fibril Deposition and Requires Syndecan-4/2 and alpha 5 beta 1 Integrin Co-signaling. *Journal of Biological Chemistry*. 285:40212-40229.

Wang, Z., D. Telci, and M. Griffin. 2011. Importance of syndecan-4 and syndecan-2 in osteoblast cell adhesion and survival mediated by a tissue transglutaminase-fibronectin complex. *Experimental Cell Research*. 317:367-381.

Yasueda, H., Y. Kumazawa, and M. Motoki. 1994. Purification and Characterization of a Tissue-Type Transglutaminase from Red-Sea Bream (Pagrus-Major). *Bioscience Biotechnology and Biochemistry*. 58:2041-2045.

EXAMPLE B

Methods

Cell adhesion and spreading assays were performed as described above in Example 1 method 'Cell adhesion assay'

Results

Smaller peptides, derived from P1 (NPKFLKNAGRDCSRRSS; SEQ ID NO: 2) were assessed for their ability to inhibit the attachment and spreading of HOB cells on FN and TG-FN in the presence and absence of RGD. The fragment peptides (NPKFLKNA [SEQ ID NO:4] and GRDCSRRSS [SEQ ID NO: 3]) were synthesised to determine the minimum functional peptide sequence required to produce the same effect as P1.

FIG. 14 shows that using the peptide NPKFLKNA (SEQ ID NO:4) at a concentration between 100 and 400 µg/ml it can be seen that the peptide was inhibitory to cell attachment and spreading at concentrations above 200 µg/ml, and it could not abrogate the compensatory effects of TG2-FN, when the cells were plated onto the TG-FN matrix in the presence of the RGD peptide.

Peptide GRDCSRRSS (SEQ ID NO: 3), however was able to inhibit the compensatory effects of TG-FN on attachment and spreading, in a dose-dependent manner (FIG. 15).

Together, this suggests that the heparan sulfate binding and signalling functions of TG2 reside mainly in the sequence GRDCSRRSS (SEQ ID NO: 3).

EXAMPLE C

Methods

In these experiments, an extended form of the exemplary "P1" peptide described above was used, in order to achieve better extension from the immobilised support. The "Extended P1" peptide comprises the full binding pocket of the heparin binding site 96-Well ELISA plates were coated with 1 µg/ml of bovine serum albumin (BSA) conjugated peptide ("Extended P1": NPKFLKNAGRDCSRRSSPVYVGRc; SEQ ID NO:29) conjugated through its C-terminal cysteine via Beta-maleimidopropionic acid N-hydroxysuccinimide ester (MPS). Peptides were dissolved in $NaHCO_3/Na_2CO_3$ coating buffer, pH 9.6 and plates coated at 4° C. for overnight. Wells coated with 1 µg/ml BSA $NaHCO_3/Na_2CO_3$ coating buffer or 5 µg/ml FN in 50 mM Tris-HCl, pH 7.4 were used as the control coating materials. Human osteoblasts (HOB) cells in suspension was treated with 100 µg/ml RAD (GRADS; SEQ ID NO:9) or RGD (GRGDTP; SEQ ID NO:8) peptide for 20 min, the cells ($3 \times 10^4$/well) were seeded into the wells, previously washed with 50 mM Tris-HCl, pH 7.4, and allowed to settle for 30 min. Attached cells were washed once with PBS, pH 7.4, and then fixed with 3.7% paraformaldehyde, further permeabilized with 0.1% (v/v) Triton® X-100 detergent in PBS, and co-stained with May-Grunwald and Giemsa stains as described previously.

Results

The data show that the soluble RGD peptide at the concentration of 100 µg/ml (as the control group) blocked around 50% of cell attachment on the FN matrix, compared to the RAD control peptide treated cells on the FN matrix, while there were no cells attached on the BSA coated wells in the presence of the control RAD peptide.

In contrast when cells were seeded onto the BSA-conjugated extended P1 peptide, ~20% RAD-treated cells were found to be attached but in the presence of the soluble RGD peptide cell attachment was restored to around 94% when cells were seeded into the wells coated with BSA-conjugated extended P1 peptide.

These data confirm that the P1 peptide or its extended form when immobilised onto a biomaterial surface that is normally unfavourable to cell adhesion will support colonisation of that surface in the presence or absence of a soluble or immobilised RGD peptide

The invention claimed is:

1. An isolated polypeptide consisting of:
   (a) the amino acid sequence according to SEQ ID NO: 1, or a functional fragment thereof comprising the amino acid sequence of SEQ ID NO: 2; or
   (b) an antibody capable of binding the polypeptide of SEQ ID NO:1, or an antigen-binding fragment thereof.

2. A polypeptide according to claim 1, wherein the polypeptide consists of an amino acid sequence of SEQ ID NO:1, or the functional fragment thereof.

3. A polypeptide according to claim 1, wherein the polypeptide is fewer than 20 amino acids in length.

4. A polypeptide according to claim 1, consisting of the amino acid sequence of SEQ ID NO: 2.

5. A polypeptide according to claim 1, wherein the polypeptide consists of an antibody capable of binding to the polypeptide of SEQ ID NO:1, or an antigen-binding fragment thereof.

6. A polypeptide according to claim 5 wherein the antigen-binding fragment thereof is selected from the group consisting of Fv fragments, Fab-like fragments, single variable domains and domain antibodies.

7. An isolated nucleic acid molecule encoding a polypeptide according to claim 1.

8. A medical implant material comprising a polypeptide according to claim 1.

9. A medical device comprising a medical implant material according to claim 8.

10. A pharmacological composition comprising a polypeptide according to claim 1.

* * * * *

SEQUENCE LISTING

```
<160> NUMBER OF SEQ ID NOS: 52

<210> SEQ ID NO 1
<211> LENGTH: 26
<212> TYPE: PRT
<213> ORGANISM: Homo sapiens

<400> SEQUENCE: 1

Leu Asp Val Asn Pro Lys Phe Leu Lys Asn Ala Gly Arg Asp Cys Ser
1               5                   10                  15

Arg Arg Ser Ser Pro Val Tyr Val Gly Arg
            20                  25

<210> SEQ ID NO 2
<211> LENGTH: 17
<212> TYPE: PRT
<213> ORGANISM: Homo sapiens

<400> SEQUENCE: 2

Asn Pro Lys Phe Leu Lys Asn Ala Gly Arg Asp Cys Ser Arg Arg Ser
1               5                   10                  15

Ser

<210> SEQ ID NO 3
<211> LENGTH: 9
```

-continued

```
<212> TYPE: PRT
<213> ORGANISM: Homo sapiens

<400> SEQUENCE: 3

Gly Arg Asp Cys Ser Arg Arg Ser Ser
1               5

<210> SEQ ID NO 4
<211> LENGTH: 8
<212> TYPE: PRT
<213> ORGANISM: Homo sapiens

<400> SEQUENCE: 4

Asn Pro Lys Phe Leu Lys Asn Ala
1               5

<210> SEQ ID NO 5
<211> LENGTH: 19
<212> TYPE: PRT
<213> ORGANISM: Homo sapiens

<400> SEQUENCE: 5

Trp Thr Ala Thr Val Val Asp Gln Gln Asp Cys Thr Leu Ser Leu Gln
1               5                   10                  15

Leu Thr Thr

<210> SEQ ID NO 6
<211> LENGTH: 6
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be a neutral or hydrophobic amino acid
      whose side chain is directed towards the protein interior
<220> FEATURE:
<221> NAME/KEY: misc_feature
<222> LOCATION: (2)..(3)
<223> OTHER INFORMATION: Asx can be a basic amino acid whose side chain
      is exposed on the protein surface
<220> FEATURE:
<221> NAME/KEY: misc_feature
<222> LOCATION: (4)..(4)
<223> OTHER INFORMATION: Xaa can be a neutral or hydrophobic amino acid
      whose side chain is directed towards the protein interior
<220> FEATURE:
<221> NAME/KEY: misc_feature
<222> LOCATION: (5)..(5)
<223> OTHER INFORMATION: Asx can be a basic amino acid whose side chain
      is exposed on the protein surface
<220> FEATURE:
<221> NAME/KEY: misc_feature
<222> LOCATION: (6)..(6)
<223> OTHER INFORMATION: Xaa can be a neutral or hydrophobic amino acid
      whose side chain is directed towards the protein interior

<400> SEQUENCE: 6

Xaa Asx Asx Xaa Asx Xaa
1               5

<210> SEQ ID NO 7
<211> LENGTH: 8
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be a neutral or hydrophobic amino acid
      whose side chain is directed towards the protein interior
<220> FEATURE:
```

```
<221> NAME/KEY: misc_feature
<222> LOCATION: (2)..(4)
<223> OTHER INFORMATION: Asx can be a basic amino acid whose side chain
      is exposed on the protein surface
<220> FEATURE:
<221> NAME/KEY: misc_feature
<222> LOCATION: (5)..(6)
<223> OTHER INFORMATION: Xaa can be a neutral or hydrophobic amino acid
      whose side chain is directed towards the protein interior
<220> FEATURE:
<221> NAME/KEY: misc_feature
<222> LOCATION: (7)..(7)
<223> OTHER INFORMATION: Asx can be a basic amino acid whose side chain
      is exposed on the protein surface
<220> FEATURE:
<221> NAME/KEY: misc_feature
<222> LOCATION: (8)..(8)
<223> OTHER INFORMATION: Xaa can be a neutral or hydrophobic amino acid
      whose side chain is directed towards the protein interior

<400> SEQUENCE: 7

Xaa Asx Asx Asx Xaa Xaa Asx Xaa
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 8

Gly Arg Gly Asp Thr Pro
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 9

Gly Arg Ala Asp Ser Pro
1               5

<210> SEQ ID NO 10
<211> LENGTH: 17
<212> TYPE: PRT
<213> ORGANISM: Artificial Sequence
<220> FEATURE:
<223> OTHER INFORMATION: Scrambled Control Peptide

<400> SEQUENCE: 10

Phe Asn Arg Ala Asp Leu Lys Pro Arg Cys Gly Ser Ser Asn Lys Ser
1               5                   10                  15

Arg

<210> SEQ ID NO 11
<211> LENGTH: 14
<212> TYPE: PRT
<213> ORGANISM: Homo sapiens

<400> SEQUENCE: 11

Ala Glu Glu Leu Val Leu Glu Arg Cys Asp Leu Glu Leu Glu
1               5                   10

<210> SEQ ID NO 12
```

```
<211> LENGTH: 14
<212> TYPE: PRT
<213> ORGANISM: Artificial Sequence
<220> FEATURE:
<223> OTHER INFORMATION: Scrambed Control Peptide

<400> SEQUENCE: 12

Glu Glu Cys Arg Leu Ala Glu Glu Leu Leu Glu Asp Val Leu
1               5                   10

<210> SEQ ID NO 13
<211> LENGTH: 37
<212> TYPE: PRT
<213> ORGANISM: Homo sapiens

<400> SEQUENCE: 13

Gly Glu Asn Pro Ile Tyr Lys Ser Ala Val Thr Thr Val Val Asn Pro
1               5                   10                  15

Ile Tyr Glu Gly Lys Arg Gln Ile Lys Ile Trp Phe Gln Asn Arg Arg
            20                  25                  30

Met Lys Trp Lys Lys
        35

<210> SEQ ID NO 14
<211> LENGTH: 37
<212> TYPE: PRT
<213> ORGANISM: Artificial Sequence
<220> FEATURE:
<223> OTHER INFORMATION: Scrambled Control Peptide

<400> SEQUENCE: 14

Gly Thr Ala Lys Ile Asn Glu Pro Tyr Ser Val Thr Val Pro Tyr Gly
1               5                   10                  15

Glu Lys Asn Lys Val Arg Gln Ile Lys Ile Trp Phe Gln Asn Arg Arg
            20                  25                  30

Met Lys Trp Lys Lys
        35

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
ggtaccatgg ccgaggagct ggtc                                          24

<210> SEQ ID NO 16
<211> LENGTH: 42
<212> TYPE: DNA
<213> ORGANISM: Artificial Sequence
<220> FEATURE:
<223> OTHER INFORMATION: Primer

<400> SEQUENCE: 16
ggacagccac cgtggtagcc cagcaagcct gcaccctctc gc                      42

<210> SEQ ID NO 17
<211> LENGTH: 41
<212> TYPE: DNA
<213> ORGANISM: Artificial Sequence
<220> FEATURE:
<223> OTHER INFORMATION: Primer
```

<400> SEQUENCE: 17 gggagccca agcaggcggc cgcgctggtg gctgaggtgt c                 41

<210> SEQ ID NO 18
<211> LENGTH: 42
<212> TYPE: DNA
<213> ORGANISM: Artificial Sequence
<220> FEATURE:
<223> OTHER INFORMATION: Primer

<400> SEQUENCE: 18
caaccccaag ttcctggcga acgccggcgc tgactgctcc cg              42

<210> SEQ ID NO 19
<211> LENGTH: 34
<212> TYPE: DNA
<213> ORGANISM: Artificial Sequence
<220> FEATURE:
<223> OTHER INFORMATION: Primer

<400> SEQUENCE: 19
ggacggtacc atgaccaatg gccgagacca ccac                       34

<210> SEQ ID NO 20
<211> LENGTH: 29
<212> TYPE: DNA
<213> ORGANISM: Artificial Sequence
<220> FEATURE:
<223> OTHER INFORMATION: Primer

<400> SEQUENCE: 20
gcggccgctt aggcggggcc aatgatgac                             29

<210> SEQ ID NO 21
<211> LENGTH: 42
<212> TYPE: DNA
<213> ORGANISM: Artificial Sequence
<220> FEATURE:
<223> OTHER INFORMATION: Primer

<400> SEQUENCE: 21
gcgagagggt gcaggcttgc tgggctacca cggtggctgt cc              42

<210> SEQ ID NO 22
<211> LENGTH: 41
<212> TYPE: DNA
<213> ORGANISM: Artificial Sequence
<220> FEATURE:
<223> OTHER INFORMATION: Primer

<400> SEQUENCE: 22
gacacctcag ccaccagcgc ggccgcctgc ttgggctccc c               41

<210> SEQ ID NO 23
<211> LENGTH: 42
<212> TYPE: DNA
<213> ORGANISM: Artificial Sequence
<220> FEATURE:
<223> OTHER INFORMATION: Primer

<400> SEQUENCE: 23
cgggagcagt cagcgccggc gttcgccagg aacttggggt tg              42

<210> SEQ ID NO 24
<211> LENGTH: 33

```
<212> TYPE: DNA
<213> ORGANISM: Artificial Sequence
<220> FEATURE:
<223> OTHER INFORMATION: Pimer

<400> SEQUENCE: 24
ggacgcggaa gcttaggcgg ggccaatgat gac                                    33

<210> SEQ ID NO 25
<211> LENGTH: 6
<212> TYPE: PRT
<213> ORGANISM: Homo sapiens

<400> SEQUENCE: 25

Leu Arg Arg Trp Lys Asn
1               5

<210> SEQ ID NO 26
<211> LENGTH: 13
<212> TYPE: PRT
<213> ORGANISM: Homo sapiens

<400> SEQUENCE: 26

Lys Ile Arg Ile Leu Gly Glu Pro Lys Gln Lys Arg Lys
1               5                   10

<210> SEQ ID NO 27
<211> LENGTH: 21
<212> TYPE: PRT
<213> ORGANISM: Homo sapiens

<400> SEQUENCE: 27

Lys Phe Leu Lys Asn Ala Gly Arg Asp Cys Ser Arg Arg Ser Ser Pro
1               5                   10                  15

Val Tyr Val Gly Arg
            20

<210> SEQ ID NO 28
<211> LENGTH: 6
<212> TYPE: PRT
<213> ORGANISM: Homo sapiens

<400> SEQUENCE: 28

Pro Val Tyr Val Gly Arg
1               5

<210> SEQ ID NO 29
<211> LENGTH: 23
<212> TYPE: PRT
<213> ORGANISM: Artificial Sequence
<220> FEATURE:
<223> OTHER INFORMATION: Conjugated peptide

<400> SEQUENCE: 29

Asn Pro Lys Phe Leu Lys Asn Ala Gly Arg Asp Cys Ser Arg Arg Ser
1               5                   10                  15

Ser Pro Val Tyr Val Gly Arg
            20

<210> SEQ ID NO 30
<211> LENGTH: 42
<212> TYPE: PRT
<213> ORGANISM: Homo sapiens

<400> SEQUENCE: 30
```

```
Asp Ile Cys Leu Ile Leu Leu Asp Val Asn Pro Lys Phe Leu Lys Asn
1               5                   10                  15

Ala Gly Arg Asp Cys Ser Arg Ser Ser Pro Val Tyr Val Gly Arg
            20                  25                  30

Val Val Ser Gly Met Val Asn Cys Asn Asp
            35                  40
```

<210> SEQ ID NO 31
<211> LENGTH: 42
<212> TYPE: PRT
<213> ORGANISM: Bovine

<400> SEQUENCE: 31

```
Asp Ile Cys Leu Met Leu Leu Asp Val Asn Pro Lys Phe Leu Arg Asn
1               5                   10                  15

Ala Gly Arg Asp Cys Ser Arg Ser Ser Pro Val Tyr Val Gly Arg
            20                  25                  30

Val Val Ser Gly Met Val Asn Cys Asn Asp
            35                  40
```

<210> SEQ ID NO 32
<211> LENGTH: 42
<212> TYPE: PRT
<213> ORGANISM: Cavia porcellus

<400> SEQUENCE: 32

```
Asp Ile Cys Leu Met Leu Leu Asp Thr Asn Pro Lys Phe Leu Lys Asn
1               5                   10                  15

Ala Gly Gln Asp Cys Ser Arg Ser Arg Pro Val Tyr Val Gly Arg
            20                  25                  30

Val Val Ser Ala Met Val Asn Cys Asn Asp
            35                  40
```

<210> SEQ ID NO 33
<211> LENGTH: 42
<212> TYPE: PRT
<213> ORGANISM: Mus musculus

<400> SEQUENCE: 33

```
Asp Thr Cys Leu Met Leu Leu Asp Met Asn Pro Lys Phe Leu Lys Asn
1               5                   10                  15

Arg Ser Arg Asp Cys Ser Arg Ser Ser Pro Ile Tyr Val Gly Arg
            20                  25                  30

Val Val Ser Ala Met Val Asn Cys Asn Asp
            35                  40
```

<210> SEQ ID NO 34
<211> LENGTH: 42
<212> TYPE: PRT
<213> ORGANISM: Rattus rattus

<400> SEQUENCE: 34

```
Asp Ala Cys Leu Met Leu Leu Asp Val Asn Pro Lys Phe Leu Lys Asp
1               5                   10                  15

Arg Ser Arg Asp Cys Ser Arg Ser Ser Pro Ile Tyr Val Gly Arg
            20                  25                  30

Val Val Ser Gly Met Val Asn Cys Asn Asp
            35                  40
```

```
<210> SEQ ID NO 35
<211> LENGTH: 42
<212> TYPE: PRT
<213> ORGANISM: Gallus gallus

<400> SEQUENCE: 35

Ala Ile Cys Leu Glu Met Leu Asp Ile Asn Pro Lys Phe Leu Arg Asp
1               5                   10                  15

Gln Asn Leu Asp Cys Ser Arg Arg Asn Asp Pro Val Tyr Ile Gly Arg
            20                  25                  30

Val Val Ser Ala Met Val Asn Cys Asn Asp
        35                  40

<210> SEQ ID NO 36
<211> LENGTH: 35
<212> TYPE: PRT
<213> ORGANISM: Homo sapiens

<400> SEQUENCE: 36

Asp Ala Cys Leu Tyr Ile Leu Asp Arg Arg Gly Met Pro Tyr Gly Gly
1               5                   10                  15

Arg Gly Asp Pro Val Asn Val Ser Arg Val Ile Ser Ala Met Val Asn
            20                  25                  30

Ser Leu Asp
        35

<210> SEQ ID NO 37
<211> LENGTH: 42
<212> TYPE: PRT
<213> ORGANISM: Homo sapiens

<400> SEQUENCE: 37

Ser Ile Cys Leu Ser Ile Leu Asp Arg Ser Leu Asn Phe Arg Arg Asp
1               5                   10                  15

Ala Ala Thr Asp Val Ala Ser Arg Asn Asp Pro Lys Tyr Val Gly Arg
            20                  25                  30

Val Leu Ser Ala Met Ile Asn Ser Asn Asp
        35                  40

<210> SEQ ID NO 38
<211> LENGTH: 35
<212> TYPE: PRT
<213> ORGANISM: Homo sapiens

<400> SEQUENCE: 38

Asp Cys Cys Ile Ser Leu Leu Thr Glu Ser Ser Leu Lys Pro Thr Asp
1               5                   10                  15

Arg Arg Asp Pro Val Leu Val Cys Arg Ala Met Cys Ala Met Met Ser
            20                  25                  30

Phe Glu Lys
        35

<210> SEQ ID NO 39
<211> LENGTH: 42
<212> TYPE: PRT
<213> ORGANISM: Homo sapiens

<400> SEQUENCE: 39

Asp Ile Cys Leu Lys Leu Leu Asp Lys Ser Leu His Phe Gln Thr Asp
1               5                   10                  15

Pro Ala Thr Asp Cys Ala Leu Arg Gly Ser Pro Val Tyr Val Ser Arg
```

```
                    20                  25                  30

Val Val Cys Ala Met Ile Asn Ser Asn Asp
            35                  40

<210> SEQ ID NO 40
<211> LENGTH: 35
<212> TYPE: PRT
<213> ORGANISM: Homo sapiens

<400> SEQUENCE: 40

Asp Thr Cys Leu Tyr Val Met Asp Arg Ala Gln Met Asp Leu Ser Gly
1               5                   10                  15

Arg Gly Asn Pro Ile Lys Val Arg Val Gly Ser Ala Met Val Asn
            20                  25                  30

Ala Lys Asp
        35

<210> SEQ ID NO 41
<211> LENGTH: 34
<212> TYPE: PRT
<213> ORGANISM: Homo sapiens

<400> SEQUENCE: 41

Asp Leu Ser Leu Arg Leu Leu Ser Lys Asp Lys Gln Val Glu Lys Trp
1               5                   10                  15

Ser Gln Pro Val His Val Ala Arg Val Leu Gly Ala Leu Leu His Phe
            20                  25                  30

Leu Lys

<210> SEQ ID NO 42
<211> LENGTH: 11
<212> TYPE: PRT
<213> ORGANISM: Homo sapiens

<400> SEQUENCE: 42

Gly Asp Leu Ser Thr Lys Tyr Asp Ala Pro Phe
1               5                   10

<210> SEQ ID NO 43
<211> LENGTH: 11
<212> TYPE: PRT
<213> ORGANISM: Cavia porcellus

<400> SEQUENCE: 43

Gly His Leu Asn Val Lys Tyr Asp Ala Pro Phe
1               5                   10

<210> SEQ ID NO 44
<211> LENGTH: 11
<212> TYPE: PRT
<213> ORGANISM: Mus musculus

<400> SEQUENCE: 44

Gly Asp Leu Ser Thr Lys Tyr Asp Ala Pro Phe
1               5                   10

<210> SEQ ID NO 45
<211> LENGTH: 11
<212> TYPE: PRT
<213> ORGANISM: Rattus rattus

<400> SEQUENCE: 45
```

Gly Asp Leu Ser Thr Lys Tyr Asp Ala Ser Phe
1               5                   10

<210> SEQ ID NO 46
<211> LENGTH: 11
<212> TYPE: PRT
<213> ORGANISM: Gallus gallus

<400> SEQUENCE: 46

Gly Asp Leu Gln Val Gln Tyr Asp Ile Pro Phe
1               5                   10

<210> SEQ ID NO 47
<211> LENGTH: 11
<212> TYPE: PRT
<213> ORGANISM: Homo sapiens

<400> SEQUENCE: 47

Gly Leu Val Tyr Met Lys Tyr Asp Thr Pro Phe
1               5                   10

<210> SEQ ID NO 48
<211> LENGTH: 11
<212> TYPE: PRT
<213> ORGANISM: Homo sapiens

<400> SEQUENCE: 48

Gly Asp Val Gln Leu Asn Phe Asp Met Pro Phe
1               5                   10

<210> SEQ ID NO 49
<211> LENGTH: 11
<212> TYPE: PRT
<213> ORGANISM: Homo sapiens

<400> SEQUENCE: 49

Gly Asp Ile Phe Ile Val Tyr Asp Thr Arg Phe
1               5                   10

<210> SEQ ID NO 50
<211> LENGTH: 11
<212> TYPE: PRT
<213> ORGANISM: Homo sapiens

<400> SEQUENCE: 50

Gly Glu Val Asp Leu Asn Tyr Asp Thr Pro Phe
1               5                   10

<210> SEQ ID NO 51
<211> LENGTH: 11
<212> TYPE: PRT
<213> ORGANISM: Homo sapiens

<400> SEQUENCE: 51

Gly His Val Cys Phe Gln Phe Asp Ala Pro Phe
1               5                   10

<210> SEQ ID NO 52
<211> LENGTH: 11

```
<212> TYPE: PRT
<213> ORGANISM: Homo sapiens

<400> SEQUENCE: 52

Gly Thr Leu Gly Leu Thr Pro Ala Val Ser Asp
1               5                   10
```